US008815838B2

(12) United States Patent
Griffith et al.

(10) Patent No.: US 8,815,838 B2
(45) Date of Patent: Aug. 26, 2014

(54) AEROSOL FLUOROQUINOLONE FORMULATIONS FOR IMPROVED PHARMACOKINETICS

(76) Inventors: David C. Griffith, San Marcos, CA (US); Michael N. Dudley, San Diego, CA (US); Mark W. Surber, San Diego, CA (US); Keith A. Bostian, Atherton, CA (US); Olga Rodny, Mountain View, CA (US)

(*) Notice: Subject to any disclaimer, the term of this patent is extended or adjusted under 35 U.S.C. 154(b) by 542 days.

(21) Appl. No.: 12/574,680

(22) Filed: Oct. 6, 2009

(65) Prior Publication Data

US 2010/0087416 A1    Apr. 8, 2010

Related U.S. Application Data

(60) Provisional application No. 61/103,501, filed on Oct. 7, 2008.

(51) Int. Cl.
| | |
|---|---|
| A61K 31/397 | (2006.01) |
| A61K 31/535 | (2006.01) |
| A61P 11/06 | (2006.01) |
| A61K 31/47 | (2006.01) |
| A61K 47/02 | (2006.01) |
| A61K 31/4375 | (2006.01) |
| A61K 31/538 | (2006.01) |
| A61K 9/00 | (2006.01) |

(52) U.S. Cl.
CPC .............. *A61K 9/0078* (2013.01); *A61K 31/47* (2013.01); *A61K 47/02* (2013.01); *A61K 31/4375* (2013.01); *A61K 31/538* (2013.01)
USPC ...................... 514/210.15; 514/230.2; 424/45

(58) Field of Classification Search
USPC .............................. 514/210.15, 230.2; 424/45
See application file for complete search history.

(56) References Cited

U.S. PATENT DOCUMENTS

| | | | |
|---|---|---|---|
| 2,587,215 A | 2/1952 | Priestly | |
| 2,868,691 A | 1/1959 | Porush et al. | |
| 3,014,844 A | 12/1961 | Thiel et al. | |
| 3,456,644 A | 7/1969 | Thiel | |
| 3,456,645 A | 7/1969 | Brock | |
| 3,456,646 A | 7/1969 | Phillips et al. | |
| 3,507,277 A | 4/1970 | Altounyan et al. | |
| 3,565,070 A | 2/1971 | Hanson et al. | |

(Continued)

FOREIGN PATENT DOCUMENTS

| | | |
|---|---|---|
| CN | 1312076 | 9/2002 |
| EP | 0 211 595 A2 | 2/1987 |

(Continued)

OTHER PUBLICATIONS

Abusriwil et al. "The interaction of host and pathogen factors in chronic obstructive pulmonary disease exacerbations and their role in tissue damage", Proc. Am. Thorac. Soc. (2007) 4(8):611-617.

(Continued)

*Primary Examiner* — Savitha Rao

(57) ABSTRACT

The present invention relates to the field of antimicrobial agents. In particular, the present invention relates to the use of aerosolized fluoroquinolones formulated with divalent or trivalent cations and having improved pulmonary availability for the treatment and management of bacterial infections of the lung and upper respiratory tract.

80 Claims, 21 Drawing Sheets

(56) References Cited

U.S. PATENT DOCUMENTS

| | | |
|---|---|---|
| 3,598,294 A | 8/1971 | Hedrick et al. |
| 3,635,219 A | 1/1972 | Altounyan et al. |
| 3,636,949 A | 1/1972 | Kropp |
| 3,669,113 A | 6/1972 | Altounyan et al. |
| 3,732,864 A | 5/1973 | Thompson et al. |
| 3,789,843 A | 2/1974 | Armstrong et al. |
| 3,807,400 A | 4/1974 | Cocozza |
| 3,826,255 A | 7/1974 | Havstad et al. |
| 3,906,950 A | 9/1975 | Cocozza |
| 3,948,264 A | 4/1976 | Wilke et al. |
| 3,971,377 A | 7/1976 | Damani |
| 3,991,761 A | 11/1976 | Cocozza |
| 4,013,075 A | 3/1977 | Cocozza |
| 4,046,146 A | 9/1977 | Rosskamp et al. |
| 4,147,166 A | 4/1979 | Hansen |
| 4,253,468 A | 3/1981 | Lehmbeck |
| 4,263,907 A | 4/1981 | Lindsey |
| 4,268,460 A | 5/1981 | Boiarski |
| 4,353,365 A | 10/1982 | Hallworth et al. |
| 4,470,412 A | 9/1984 | Nowacki et al. |
| 4,510,929 A | 4/1985 | Bordoni et al. |
| 4,534,345 A | 8/1985 | Wetterlin |
| 4,624,251 A | 11/1986 | Miller |
| 4,648,393 A | 3/1987 | Landis et al. |
| 4,649,911 A | 3/1987 | Knight et al. |
| 4,664,107 A | 5/1987 | Wass |
| 4,667,668 A | 5/1987 | Wetterlin |
| 4,688,218 A | 8/1987 | Blineau et al. |
| 4,730,000 A | 3/1988 | Chu |
| 4,790,305 A | 12/1988 | Zoltan et al. |
| 4,805,811 A | 2/1989 | Wetterlin |
| 4,807,814 A | 2/1989 | Douche et al. |
| 4,809,692 A | 3/1989 | Nowacki et al. |
| 4,811,731 A | 3/1989 | Newell et al. |
| 4,832,015 A | 5/1989 | Nowacki et al. |
| 4,844,902 A | 7/1989 | Grohe |
| 4,857,311 A | 8/1989 | Domb et al. |
| 4,889,144 A | 12/1989 | Tateno et al. |
| 4,907,538 A | 3/1990 | Helmle et al. |
| 4,926,852 A | 5/1990 | Zoltan et al. |
| 4,955,371 A | 9/1990 | Zamba et al. |
| 4,985,557 A | 1/1991 | Hayakawa et al. |
| 5,012,803 A | 5/1991 | Foley et al. |
| 5,012,804 A | 5/1991 | Foley et al. |
| 5,024,467 A | 6/1991 | Truchet |
| 5,027,806 A | 7/1991 | Zoltan et al. |
| 5,033,463 A | 7/1991 | Cocozza |
| 5,040,527 A | 8/1991 | Larson et al. |
| 5,053,407 A | 10/1991 | Hayakawa et al. |
| 5,060,643 A | 10/1991 | Rich et al. |
| 5,113,855 A | 5/1992 | Newhouse |
| 5,119,806 A | 6/1992 | Palson et al. |
| 5,142,046 A | 8/1992 | Hayakawa et al. |
| 5,164,740 A | 11/1992 | Ivri |
| 5,217,004 A | 6/1993 | Blasnik et al. |
| 5,284,133 A | 2/1994 | Burns et al. |
| 5,304,559 A | 4/1994 | Rozier |
| 5,334,589 A | 8/1994 | Al-Razzak et al. |
| 5,347,998 A | 9/1994 | Hodson et al. |
| 5,364,838 A | 11/1994 | Rubsamen |
| 5,385,140 A | 1/1995 | Smith |
| 5,388,572 A | 2/1995 | Mulhauser et al. |
| 5,404,871 A | 4/1995 | Goodman et al. |
| 5,427,089 A | 6/1995 | Kraemer |
| 5,437,270 A | 8/1995 | Braithwaite |
| 5,478,578 A | 12/1995 | Arnold et al. |
| 5,508,269 A | 4/1996 | Smith et al. |
| 5,549,102 A | 8/1996 | Lintl et al. |
| 5,563,155 A | 10/1996 | Domagala et al. |
| 5,586,550 A | 12/1996 | Ivri et al. |
| 5,642,730 A | 7/1997 | Baran |
| 5,645,049 A | 7/1997 | Foley et al. |
| 5,694,920 A | 12/1997 | Abrams et al. |
| 5,709,202 A | 1/1998 | Loyd et al. |
| 5,740,794 A | 4/1998 | Smith et al. |
| 5,756,506 A | 5/1998 | Copeland et al. |
| 5,758,637 A | 6/1998 | Ivri et al. |
| 5,775,320 A | 7/1998 | Patton et al. |
| 5,785,049 A | 7/1998 | Smith et al. |
| 5,816,240 A | 10/1998 | Komesaroff |
| 5,820,873 A | 10/1998 | Choi et al. |
| 5,823,179 A | 10/1998 | Grychowski et al. |
| 5,829,434 A | 11/1998 | Ambrosio et al. |
| 5,840,279 A | 11/1998 | Narodylo et al. |
| 5,906,202 A | 5/1999 | Schuster et al. |
| 5,918,594 A | 7/1999 | Asking et al. |
| 5,934,272 A | 8/1999 | Lloyd et al. |
| 5,960,792 A | 10/1999 | Lloyd et al. |
| 5,971,951 A | 10/1999 | Ruskewicz |
| 5,988,160 A | 11/1999 | Foley et al. |
| 6,003,512 A | 12/1999 | Gerde |
| 6,006,747 A | 12/1999 | Eisele et al. |
| 6,026,807 A | 2/2000 | Puderbaugh et al. |
| 6,026,809 A | 2/2000 | Abrams et al. |
| 6,029,662 A | 2/2000 | Marcom |
| 6,070,575 A | 6/2000 | Gonda et al. |
| 6,083,922 A | 7/2000 | Montgomery |
| 6,161,536 A | 12/2000 | Redmon et al. |
| 6,192,876 B1 | 2/2001 | Denyer et al. |
| 6,196,219 B1 | 3/2001 | Hess et al. |
| 6,223,746 B1 | 5/2001 | Jewett et al. |
| 6,230,706 B1 | 5/2001 | Gonda et al. |
| 6,264,922 B1 | 7/2001 | Wood et al. |
| 6,288,080 B1 | 9/2001 | Barsuhn et al. |
| 6,294,178 B1 | 9/2001 | Weinstein et al. |
| 6,333,044 B1 | 12/2001 | Santus et al. |
| 6,333,045 B1 | 12/2001 | Yasueda et al. |
| 6,338,443 B1 | 1/2002 | Piper |
| 6,349,719 B2 | 2/2002 | Gonda |
| 6,350,199 B1 | 2/2002 | Williams et al. |
| 6,367,470 B1 | 4/2002 | Denyer et al. |
| 6,406,880 B1 | 6/2002 | Thornton |
| 6,427,682 B1 | 8/2002 | Klimowicz et al. |
| 6,435,177 B1 | 8/2002 | Schmidt et al. |
| 6,468,967 B1 | 10/2002 | Oleson, Jr. et al. |
| 6,492,328 B2 | 12/2002 | Lehrer et al. |
| 6,503,953 B2 | 1/2003 | Vyden |
| 6,518,239 B1 | 2/2003 | Kuo et al. |
| 6,523,536 B2 | 2/2003 | Fugelsang et al. |
| 6,543,442 B2 | 4/2003 | Gonda et al. |
| 6,544,555 B2 | 4/2003 | Rudnic et al. |
| 6,557,549 B2 | 5/2003 | Schmidt et al. |
| 6,561,186 B2 | 5/2003 | Casper et al. |
| 6,576,224 B1 | 6/2003 | Osbakken et al. |
| 6,579,854 B1 | 6/2003 | Mitchell et al. |
| 6,584,971 B1 | 7/2003 | Denyer et al. |
| 6,585,958 B1 | 7/2003 | Keller et al. |
| 6,586,008 B1 | 7/2003 | Batycky et al. |
| 6,601,581 B1 | 8/2003 | Babaev |
| 6,605,609 B2 | 8/2003 | Barbachyn et al. |
| 6,608,078 B2 | 8/2003 | De Souza et al. |
| 6,612,303 B1 | 9/2003 | Grychowski et al. |
| 6,626,173 B2 | 9/2003 | Genova et al. |
| 6,644,304 B2 | 11/2003 | Grychowski et al. |
| 6,663,890 B2 | 12/2003 | Rudnic et al. |
| 6,663,891 B2 | 12/2003 | Rudnic et al. |
| 6,664,239 B2 | 12/2003 | Mitchell et al. |
| 6,667,042 B2 | 12/2003 | Rudnic et al. |
| 6,667,057 B2 | 12/2003 | Rudnic et al. |
| 6,669,948 B2 | 12/2003 | Rudnic et al. |
| 6,672,304 B1 | 1/2004 | Casper et al. |
| 6,681,768 B2 | 1/2004 | Haaije de Boer et al. |
| 6,689,769 B2 | 2/2004 | Gordeev et al. |
| 6,716,819 B2 | 4/2004 | Welsh et al. |
| 6,723,341 B2 | 4/2004 | Rudnic et al. |
| 6,730,320 B2 | 5/2004 | Rudnic et al. |
| 6,756,369 B2 | 6/2004 | Mitchell et al. |
| 6,806,256 B2 | 10/2004 | Ulrich et al. |
| 6,835,372 B2 | 12/2004 | Kuo et al. |
| 6,838,552 B1 | 1/2005 | Mitchell et al. |
| 6,869,965 B2 | 3/2005 | Gordeev et al. |
| 6,878,713 B2 | 4/2005 | De Souza et al. |
| 6,884,784 B1 | 4/2005 | Mitchell et al. |
| 6,890,526 B2 | 5/2005 | Stratton et al. |

(56) References Cited

U.S. PATENT DOCUMENTS

| | | |
|---|---|---|
| 6,962,151 B1 | 11/2005 | Knoch et al. |
| 6,987,094 B2 | 1/2006 | Malvolti et al. |
| 7,148,404 B2 | 12/2006 | Hogenhaug et al. |
| 7,838,532 B2 | 11/2010 | Surber et al. |
| 2001/0049366 A1 | 12/2001 | Singh et al. |
| 2002/0061281 A1 | 5/2002 | Osbakken et al. |
| 2002/0086867 A1 | 7/2002 | Dubois et al. |
| 2002/0142050 A1 | 10/2002 | Straub et al. |
| 2002/0197212 A1 | 12/2002 | Osbakken et al. |
| 2003/0012814 A1 | 1/2003 | Rudnic et al. |
| 2003/0028025 A1 | 2/2003 | Raghavan |
| 2003/0032600 A1 | 2/2003 | Ulrich et al. |
| 2003/0078517 A1 | 4/2003 | Kensey |
| 2003/0138403 A1 | 7/2003 | Drustrup |
| 2003/0171340 A1 | 9/2003 | Isbister |
| 2003/0186894 A1 | 10/2003 | Kuo et al. |
| 2004/0009126 A1 | 1/2004 | Pilkiewicz et al. |
| 2004/0009989 A1 | 1/2004 | Niddam-Hildesheim et al. |
| 2004/0014750 A1 | 1/2004 | Michaelis et al. |
| 2004/0045546 A1 | 3/2004 | Hirsh et al. |
| 2004/0152701 A1 | 8/2004 | Reddy et al. |
| 2005/0036951 A1 | 2/2005 | Henderson |
| 2005/0106151 A1 | 5/2005 | Shapiro |
| 2005/0139211 A1 | 6/2005 | Alston et al. |
| 2005/0147567 A1 | 7/2005 | Kuo et al. |
| 2005/0235987 A1 | 10/2005 | Smaldone et al. |
| 2005/0260099 A1 | 11/2005 | Xia et al. |
| 2005/0288302 A1 | 12/2005 | Niddam-Hildesheim et al. |
| 2006/0003944 A1 | 1/2006 | Glinka et al. |
| 2006/0025355 A1 | 2/2006 | Duddu et al. |
| 2006/0223751 A1 | 10/2006 | Mygind et al. |
| 2006/0258677 A1 | 11/2006 | Amir et al. |
| 2006/0276416 A1* | 12/2006 | Sinclair et al. .................. 514/27 |
| 2006/0276463 A1 | 12/2006 | Sharma et al. |
| 2006/0276473 A1 | 12/2006 | Bostion et al. |
| 2006/0276483 A1 | 12/2006 | Surber et al. |
| 2006/0286574 A1 | 12/2006 | Romesberg et al. |
| 2007/0003753 A1 | 1/2007 | Asgari |
| 2007/0071686 A1 | 3/2007 | Lintz et al. |
| 2007/0155715 A1 | 7/2007 | van Duzer et al. |
| 2007/0197548 A1 | 8/2007 | Murthy |
| 2009/0025713 A1 | 1/2009 | Keller et al. |
| 2010/0087386 A1 | 4/2010 | Dudley et al. |
| 2010/0204470 A1 | 8/2010 | Wieser et al. |

FOREIGN PATENT DOCUMENTS

| | | |
|---|---|---|
| EP | 0 347 779 | 12/1989 |
| EP | 0 455 463 A1 | 11/1991 |
| EP | 0 467 172 A1 | 1/1992 |
| EP | 0 470 667 A1 | 2/1992 |
| EP | 0 855 183 A2 | 7/1998 |
| EP | 1 092 430 A1 | 4/2001 |
| EP | 1 223 915 B1 | 12/2005 |
| GB | 901107 A | 7/1962 |
| SU | 628930 | 10/1978 |
| WO | WO 87/05213 | 9/1987 |
| WO | WO 90/07351 | 7/1990 |
| WO | WO 90/13327 | 11/1990 |
| WO | WO 92/09322 | 6/1992 |
| WO | WO 93/12831 | 7/1993 |
| WO | WO 93/24165 | 12/1993 |
| WO | WO 95/11666 | 5/1995 |
| WO | WO 96/23485 | 8/1996 |
| WO | WO 97/03649 | 2/1997 |
| WO | WO 98/03217 | 1/1998 |
| WO | WO 99/59566 | 11/1999 |
| WO | WO 99/62495 | 12/1999 |
| WO | WO 00/18388 A1 | 4/2000 |
| WO | WO 01/02024 | 1/2001 |
| WO | WO 02/18345 | 3/2002 |
| WO | WO 02/072102 | 9/2002 |
| WO | WO 03/035030 A1 | 5/2003 |
| WO | WO 03/066064 A2 | 8/2003 |
| WO | WO 03/075889 A1 | 9/2003 |
| WO | WO 2004/019912 | 3/2004 |
| WO | WO 2005/037256 A2 | 4/2005 |
| WO | WO 2005/089738 | 9/2005 |
| WO | WO 2006/011051 A1 | 2/2006 |
| WO | WO 2006/033713 | 3/2006 |
| WO | WO 2006/078925 A2 | 7/2006 |
| WO | WO 2006/125132 A2 | 11/2006 |
| WO | WO 2007/085057 | 8/2007 |
| WO | WO 2007/090123 | 8/2007 |
| WO | WO 2007/090646 | 8/2007 |
| WO | WO 2007/095156 | 8/2007 |
| WO | WO 2007/095187 | 8/2007 |
| WO | WO 2008/025560 A1 | 3/2008 |
| WO | WO 2009/140587 | 11/2009 |
| WO | WO 2010/042549 | 4/2010 |
| WO | WO 2010/042553 | 4/2010 |
| WO | WO 2010/124141 | 10/2010 |
| WO | WO 2011/022075 | 2/2011 |
| WO | WO 2011/029059 | 3/2011 |

OTHER PUBLICATIONS

Aggarwal et al., "Predictors of mortality and resource utilization in cirrhotic patients admitted to the medical ICU", Chest (2001) 119(5):1489-1497.

Ambrose, Paul G.et al., "Pharmacokinetics-Pharmacodynamics of Antimicrobial Therapy: It's Not Just for Mice Anymore", Antimicrobial Resistance (2007) 44:79-86.

Amsden, "Anti-inflmmatory effects of macrolides—an underappreciated benefit in the treatment of community-acquired respiratory tract infections and chronic inflammatory pulmonary conditions?", Journal of Antimicrobial Chemotherapy (2005) 55:10-21.

Anonymous, Mpex Candidate, MP-376, Granted US Orphan Drug Status for the Treatment of Cystic Fibrosis, Medical News Today, www.medicalnewstoday.com (retrieved online Dec. 11, 2009), Mar. 5, 2008, XP002560239.

Araujo et al., "Effect of moxifloxacin on secretion of cytokines by human monocytes stimulated with lipopolysaccharide", Clin. Microbiol. Infect. (2002) 8:26-30.

Araujo et al., "Gemifloxacin inhibits cytokine secretion by lipopolysaccharide stimulated human monocytes at the post-transcriptional level", Clin. Microbiol. Infect. (2004) 10:213-219.

Arzte, Zeitung De, www.aerztezeitung.de/extras/druckansicht/?sid=347342&pid=351267 (retrieved online Dec. 11, 2009), Mar. 14, 2005, XP002560241. (Machine Translation Provided).

Atkins et al., "The Design and Development of Inhalation Drug Delivery Systems", Pharmaceutical Inhalation Aerosol Technology, Marcel Dekker, Inc., New York, NY (1992) 6: p. 155-185.

Baker et al., "A Prodrug Approach Toward the Development of Water Soluble Fluoroquinolones and Structure-Activity Relationships of Quinoline-3-Carboxylic Acids" J. Med. Chem. (2004) 47:4693-4709.

Banerjee et al., "The treatment of respiratory pseudomonas infection in cystic fibrosis: what drug and which way?" Drugs (2000) 60(5):1053-64. (Abstract Only).

Barry et al., "Novel agents in the management of *Mycobacterium tuberculosis* disease" Current medicinal chemistry (Netherlands) (2007) 14(18):2000-8. (Abstract Only).

Battram et al., "In vitro and in vivo pharmacological characterization of 5-[®-2-(5,6-diethyl-indan-2-ylamino)-1-hydroxy-ethyl]-8-hydroxy-1H-quinolin-2-one (indacaterol), a novel inhaled beta(2) adrenoceptor agonist with a 24-h duration of action", J Pharmacol Exp Ther. (2006) 317(2):762-70. (Abstract Only).

Beasley et al., "Adverse reactions to the non-drug constituents of nebuliser solutions", Br. J. clin. Pharmac., (1988) 25: p. 283-287.

Benko et al., "Pharmacokinetics and pharmacodynamics of levofloxacin in critically ill patients with ventilator-associated pneumonia" International journal of antimicrobial agents (Netherlands) (2007) 30(2):162-8. (Abstract Only).

Berg, "Combination products are spotlighted at Drug/Device Summit" The BBI Newsletter (2005). (Abstract Only).

Blaser et al., "Influence of Medium and Method on the in Vitro Susceptibility of Pseudomonas Aeruginos and Other Bacteria to

(56) References Cited

OTHER PUBLICATIONS

Ciprofloxacin and Enoxacin, Antimicrobial Agents and Chemotherapy", American Society for Microbiology (1986) 29(5):927-929.
Blau et al., "Moxifloxacin but not Ciprofloxacin or Azithromycin Selectively Inhibits IL-8, IL-6, ERK1/2, JNK, and NF-kB Activation in a Cystic Fibrosis Epithelial Cell Line", Am. J. Physiol. Lung Cell Mol. Physiol. (2007) 292:L343-L352.
Blitz et al., "Aerosolized Magnesium Sulfate for Acute Asthma: A Systematic Review", Chest the Cardiopulmonary and Critical Care Journal, (2005) 128: p. 337-344.
Brouillard et al., "Antibiotic selection and resistance issues with fluoroquinolones and doxycycline against bioterrorism agents" Pharmacotherapy (United States) (2006) 26(1):3-14. (Abstract Only).
Bryskier, "*Bacillus anthracis* and antibacterial agents" Clinical microbiology and infection—the official publication of the European Society of Clinical Microbiology and Infectious Diseases (France) (2002) 8(8):467-78. (Abstract Only).
Calbo et al., "Systemic expression of cytokine production in patients with severe pneumococcal pneumonia: effects of treatment with a beta-lactam versus a fluoroquinolone, antimicrobial agents and chemotherapy", American Society for Microbiology (2008) 52(7):2395-2402.
Carratala et al., "Clinical experience in the management of community-acquired pneumonia: lessons from the use of fluoroquinolones" Clinical microbiology and infection—the official publication of the European Society of Clinical Microbiology and Infectious Diseases (France) (2006) 12(3):2-11. (Abstract Only).
Cazzola, et al., "Delivering antibacterials to the lungs: considerations for optimizing outcomes", Am. J. Respir. Med. (2002) 1(4):261-272.
Celli et al., "The body-mass index, airflow obstruction, dyspnea, and exercise capacity index in chronic obstructive pulmonary disease", N Engl J Med. (2004) 350(10):1005-1012.
Chang et al., Properties of the Drug Molecule in Nasal Systemic Drug Delivery, 1989, pp. 49-51, Chapter 3, Marcel Dekker, Inc.
Chhabra et al. "Evaluation of three scales of dyspnea in chronic obstructive pulmonary disease" Ann Thorac Med (2009) 4:128-132.
Chien et al., "Properties of the Drug Molecule in Nasal Systemic Drug Delivery", (1989) pp. 63-68, Chapter 3, Marcel Dekker, Inc.
Chodosh S., "Clinical significance of the infection-free interval in the management of acute bacterial exacerbations of chronic bronchitis", Chest (2005) 127(6):2231-2236.
Choi et al., "Effect of moxifloxacin on production of proinflammatory cytokines from human peripheral blood mononuclear cells", Antimicrobial Agents and Chemotherapy (2003) 47(12):3704-3707.
Cigana et al., "Azithromycin selectively reduces tumor necrosis factor alpha levels in cystic fibrosis airway epithelial cells", Antimicrob. Agents Chemother. (2007) 51(3):975-981.
Conrad, "Mpex 204 Phase 2", Stanford School of Medicine (retrieved online Dec. 11, 2009), Sep. 3, 2008, pp. 1-7 (PCT ISR/WO provided a partial reference, and the full reference is no longer available.).
Conte et al., "intrapulmonary pharmacodynamics of high-dose levofloxacin in subjects with chronic bronchitis or chronic obstructive pulmonary disease", International Journal of Antimicrobial Agents, Elsevier Science, Amsterdam, NL (2007) 30(5):422-427.
Cooney et al., "Absolute bioavailability and absorption characteristics of aerosolized tobramycin in adults with cystic fibrosis", J. Clinical Pharmacol. (1994) 34(3):255-259.
Dalhoff et al., "Immunomodulatory effects of quinolones", The Lancet Infectious Diseases (2003) 3:359-71.
Dalhoff, "Immunomodulatory activities of fluoroquinolones", Infection (2005) 33(Suppl 2):55-70.
Den Hollander, et al., "Synergism between tobramycin and ceftazidime against a resistant *Pseudomonas aeruginosa* strain, tested in an in vitro pharmacokinetic model", Antimicrob. Agents Chemother. (1997) 41(1):95-100.
DeRyke et al., "Pharmacodynamic target attainment of six beta-lactams and two fluoroquinolones against *Pseudomonas aeruginosa, Acinetobacter baumannii, Escherichia coli,* and Klebsiella species collected from United States intensive care units in 2004" Pharmacotherapy (United States) (2007) 27(3):333-42. (Abstract Only).
Diakov et al., "The chemotherapeutic efficacy of ciprofloxacin and lomefloxacin in the inhalation method of infecting white mice with tularemia., Khimioterapevticheskaia effektivnost' tsiprofloksatsina i lomefloksatsina pri ingaliatsionnom sposobe zarazheniia tuliaremiei belykh myshei" Antibiotiki i khimioterapii a = Antibiotics and chemoterapy sic / Ministerstvo meditsinskoi i mikrobiologicheskoi promyshlennosti SSSR (Russia) (2000) 45(6):17-20. (Abstract Only).
Donnarumma et al., "Anti-inflammatory effects of moxifloxacin and human beta-defensin 2 association in human lung epithelial cell line (A549) stimulated with lipopolysaccharide", Peptides (2007) 28:2286-2292.
Doring et al., "Antibiotic therapy against *Pseudomonas aeruginosa* in cystic fibrosis: a European consensus" [comment in Eur Respir J. 2000 16(4):585-7], Euro Respir J. (2000) 16(4):749-67. (Abstract Only).
Drevensek et al., "Influence of Copper(II) and Magnesium(II) ions on the Ciprofloxacin Binding to DNA", J.Inorg. Biochem. (2003) 96:407-415.
Drevensek et al., "X-Ray Crystallographic, NMR and Antimicrobial Activity Studies of Magnesium Complexes of Fluoroquinolones—Racemic Ofloxacin and its S-form, Levofloxacin" J. lnorg. Biochem. (2006) 100:1755-1763.
Drusano et al., "Pharmacodynamics of a Fluoroquinolone Antimicrobial Agent in a Neutropenic Rat Model of Pseudomonas Sepsis" Antimicrob. Agents & Chemother. (1993) 37(3):483-490.
Elizur et al., "Airway inflammation in cystic fibrosis," Chest (2008) 133:489-495.
File, "A New Dosing Paradigm: High-Dose, Short-Course Fluoroquinolone Therapy for Community-Acquired Pneumonia" Clinical Cornerstone (2003) 3:S21-S28.
Flume et al., "Cystic Fibrosis Pulmonary Guidelines: Chronic Medications for Maintenance of Lung Health," Am J Respir Crit Care Med (2007) 176:957-969.
Fuchs et al., "Effect of aerosolized recombinant human DNase on exacerbations of respiratory symptoms and on pulmonary function in patients with cystic fibrosis", The Pulmozyme Study Group, N Engl J Med. (1994) 331(10):637-642.
Garrity et al., "Bergey's Manual of Systematic Bacteriology," Editor-in-chief: Garrity, George M. Boone, David R.; Castenholz, Richard W. (Eds.) Originally published by Williams & Wilkins, 1984, 2nd ed. (2001).
Gavilanes et al., "Azithromycin fails to reduce increased expression of neutrophil-related cytokines in primary-cultured epithelial cells from cystic fibrosis mice", J. Cyst. Fibros. (2009) 10(1016):1-8.
Gennaro, "Remington: Practice of The Science and Pharmacy", 19.sup.th ed., Williams & Williams, (1995).
Gibaldi et al., "Pharmacokinetics", 2nd Edition, Marcel Dekker: New York (1982).
Goh et al., "Current Status of Topical Nasal Antimicrobial Agents" The Laryngoscope (2000) 110:875-880.
Griese et al., "Amphotericin B and Pulmonary Surfactant", European Journal of Medical Research, , I. Holzapfel Publishers (1998) 3:383-386.
Griffith et al., "Pharmacodynamics of levofloxacin against *Pseudomonas aeruginosa* with reduced susceptibility due to different efflux pumps: do elevated MICs always predict reduced in vivo efficacy?" Antimicrob Agents Chemother. (2006) 50(5):1628-32.
Griffith et al., "Efficacy of fluoroquinolones against *Leptospira interrogans* in a hamster model" Antimicrobial agents and chemotherapy (United States) (2007) 51(7):2615-7. (Abstract only).
Griffith et al., In-vitro antibacterial activity of aerosol MP 376 in mouse models of pulmonary infection, Pediatr. Pulmonol. (2007) 42(S30):304.
Griffith et al., "Pharmacokinetics and Safety of MP-376 (Levofloxacin Solution for Inhalation) in Normal Healthy Volunteers and Cystic Fibrosis Patients", Pediatr. Pulmonol., (2007) 42(S30):303.

(56) References Cited

OTHER PUBLICATIONS

Guina et al., "Quantitative proteomic analysis indicates increased synthesis of a quinolone by *Pseudomonas aeruginosa* isolates from cystic fibrosis airways", PNAS, Mar. 4, 2003, vol. 100, No. 5, p. 2771-2776.

Handbook of Pharmaceutical Excipients, published jointly by the American Pharmaceutical Association and The Pharmaceutical Society of Great Britain (The Pharmaceutical Press, 1986).

Hart et al., "Cross-over assessment of serum bactericidal activity of moxifloxacin and levofloxacin versus penicillin-susceptible and penicillin-resistant *Streptococcus pneumoniae* in healthy volunteers", Diagnostic microbiology and infectious disease (United States) (2007) 58(3):375-8. (Abstract Only).

Hashimoto et al., "Grepafloxacin Inhibits Tumor Necrosis Factor-alpha-induced Interleukin-8 Expression in Human Airway Epithelial Cells", Life Sci (2000) 66(5):PL 77-82.

Hecht et al., "In vitro activities of 15 antimicrobial agents against 110 toxigenic clostridium difficile clinical isolates collected from 1983 to 2004" Antimicrobial agents and chemotherapy (United States) (2007) 51(8):2716-9. (Abstract Only).

Heine et al., "Comparison of 2 antibiotics that inhibit protein synthesis for the treatment of infection with *Yersinia pestis* delivered by aerosol in a mouse model of pneumonic plague", Journal of Infectious Diseases (United States) (2007) 196(5):782-7. (Abstract Only).

Hodson, "Antibiotic Treatment: Aerosol Therapy", Chest (1988) 94:156S-160S.

Hoffmann, et al., "Novel mouse model of chronic pseudomonas aeruginosa lung infection mimicking cystic fibrosis", Infect. Immun. (2005) 73(4):2504-2514.

Honeybourne, "Antibiotic penetration in the respiratory tract and implications for the selection of antimicrobial therapy" Curr Opin Pulm Med. (1997) 3(2):170-4. (Abstract Only).

Horiguchi et al., "Usefulness of sparfloxacin against *Chlamydia pneumoniae* infection in patients with bronchial asthma" Journal of international medical research (England) Nov.-Dec. 2005 33(6):668-76. (Abstract Only).

Hrkach et al., "Synthesis of poly(l-lactic acid-co-L-lysine) graft copolymers", Macromolecules (1995) 28: 4736-4739.

Huang et al., "Oxidation of fluoroquinolone antibacterials and structurally related amines with manganese oxide" National Meeting—American Chemical Society Division of Environmental Chemistry (2003) 43(2)(5):1257-1260.

Hung et al., "Evaluation of two commercial jet nebulisers and three compressors for the nebulisation of antibiotics", Archives of Disease in Childhood (1994) 71(4):335-338.

Hutschala et al., "In vivo measurement of levofloxacin penetration into lung tissue: CPB versus OPCAB" European Journal of Anaesthesiology (2005) 49(12) 5107-11.

Jacquot et al., "Airway epithelial cell inflammatory signalling in cystic fibrosis," The International Journal of Biochemistry & Cell Biology (2008) 40:1703-15.

Jarraud et al., "Legionnaires disease (Legionellose)" Presse medicale (Paris, France—1983) (France) (2007) 36(2 Pt 2):279-87. (Abstract Only).

Jensen et al., "The efficacy and safety of ciprofloxacin and ofloxacin in chronic *Pseudomonas aeruginosa* infection in cystic fibrosis", J Antimicrob Chemother. (1987) 20(4):585-94.

Jones et al., "Quantifying of severity of exacerbations in chronic obstructive pulmonary disease: adaptations to the definition to allow quantification", Proc Am Thorac Soc. (2007) 4(8):597-601.

Jumbe et al., "Application of a mathematical model to prevent in vivo amplification of antibiotic-resistant bacterial populations during therapy", J Clin Invest. (2003) 112(2):275-85.

Khan et al., "Effect of trovafloxacin on production of cytokines by human monocytes", Antimicrobial Agents and Chemotherapy (1998) 42(7):1713-7.

Khan et al., "Protection against lipopolysaccharide-induced death by fluoroquinolones," Antimicrobial Agents and Chemotherapy, (2000) 44(11): 3169-73.

King et al., "Effect of oxygen limitation on the in vitro activity of levofloxacin and other antibiotics administered by the aerosol route against *Pseudomonas aeruginosa* from cystic fibrosis patients", Diagn Microbiol Infect Dis. Feb. 2010;66(2):181-6. Epub Oct. 13, 2009.

Kitazawa et al., "Biphasic regulation of levofloxacin on lipopolysaccharide-induced IL-1B production", Life Sciences, (2007) 80:1572-1577.

Kobayashi et al., "Antibacterial activity of tosufloxacin against major organisms detected from patients with respiratory infections" Japanese journal of antibiotics (Japan) (2007) 60(2):98-106. (Abstract Only).

Kohyama et al., "Fourteen-member macrolides inhibit interleukin-8 release by human eosinophils from atopic donors", Antimicrobial Agents and Chemotherapy (1999) 43(4):907-911.

Kraynack et al., "Improving care at cystic fibrosis centers through quality improvement", Semin Respir Crit Care Med. (2009) 30(5):547-558.

Kuhn, "Formulation of aerosolized therapeutics", Chest, The Cardiopulmonary and Critical Care Journal (2001) 120(3):94S-98S. (Abstract Only).

Kurosaka et al., "DX-619, a novel des-F(6)-quinolone: pharmacodynamics (PD) activity and thereapeutic efficacy in animal infection models", Interscience Conference on Antimicrobial Agents and Chemotherapy (2003) 43$^{rd}$:Chicago.

LaPlante et al., "Fluoroquinolone resistance in *Streptococcus pneumoniae*: area under the concentration-time curve/MIC ratio and resistance development with gatifloxacin, gemifloxacin, levofloxacin, and moxifloxacin" Antimicrobial agents and chemotherapy (United States) (2007) 51(4):1315-20. (Abstract Only).

Le Conte et al., "Lung Distribution and Pharmacokinetics of Aerosolized Tobramycin", American Review of Respiratory Disease, (1993) vol. 147, p. 1279-1282.

Lee et al., "Levofloxacin pharmacokinetics in adult cystic fibrosis", Chest (2007) 131(3):796-802.

Legssyer et al., "Azithromycin reduces spontaneous and induced inflammation in F508 cystic fibrosis mice", Respiratory Research (2006) 7(134):1-13.

Leiva et al., "Effects of telithromycin in in vitro and in vivo models of lipopolysaccharide-induced airway inflammation", Chest (2008) 134:20-29.

Leonard et al., "Topical Antibiotic Therapy for Recalcitrant Sinusitis" The Laryngoscope (1999) 109(4): 668-670.

Lode et al., "Levofloxacin versus clarithromycin in copd exacerbation: focus on exacerbation-free interval", Eur Respir J. (2004) 24(6):947-953.

Louie et al., "Impact of resistance selection and mutant growth fitness on the relative efficacies of streptomycin and levofloxacin for plague therapy", Antimicrob Agents Chemother. (2007) 51(8):2661-2667. Epub May 21, 2007. (Abstract Only).

Martinez et al., "Appropriate outpatient treatment of acute bacterial exacerbations of chronic bronchitis", American Journal of Medicine, Elsevier Science, Amsterdam, NL (2005) 118(7A): 39S-44S.

Matthys, "Inhalation delivery of asthma drugs" Lung. (1990) 168:645-52. (Abstract Only).

Meguro et al., "Development and validation of an improved, COPD-specific version of the St George's Respiratory Questionnaire" Chest (2007) 132(2):456-463.

Miller et al., "Standardisation of spirometry", American Thoracic Society/European Respiratory Society (ATS/ERS) Spirometry Standards, Eur Respir J (2005) 26(2):319-338.

Mohammed et al., "Intravenous and nebulised magnesium sulphate for acute asthma: systematic review and meta-analysis", Emergency Medicine Journal (2007) 24: p. 823-830.

Moss, "Administration of aerosolized antibiotics in cystic fibrosis patients" Chest (2001) 120(3):107S-113S. (Abstract Only).

Murphy et al., "*Pseudomonas aeruginosa* in chronic obstructive pulmonary disease", Am J Respir Crit Care Med. (2008) 177(8):853-60. Epub Jan. 17, 2008.

Nakanishi et al., "A case of cystic fibrosis in a Japanese student" Nihon Kyobu Shikkan Gakkai zasshi (Japan) (1995) 33(7):771-4. (Abstract Only).

(56) References Cited

OTHER PUBLICATIONS

Neu, "The Effects of Cations Upon the Activity of Quinolone Agents", Quinolones Bulletin, Reports on Gyrase Inhibitors (1985).
Neu et al., "In Vitro Activity of S-Ofloxacin", Antimicrobial Agents and Chemotherapy, American Society for Microbiology (1989) 33 (7):1105-1107.
Newman, "Aerosols and the Lung:Clinical and Experimental Aspects", Butterworth & Co. Ltd., London, England (1984) 197-224.
Nouira et al., "Once daily oral ofloxacin in chronic obstructive pulmonary disease exacerbation requiring mechanical ventilation: a randomised placebo-controlled trial", Lancet (North American Edition) (2001) 358(9298): 2020-2025.
O-Lee et al, "Fluoroquinolone-induced arthralgia and myalgia in the treatment of sinusitis", Am. J. Rhinol. (2005) 19(4):395-399.
Ono et al., "Effect of grepafloxacin on cytokine production in vitro", Journal of Antimicrobial Chemotherapy, (2000) 46:91-94.
Ortho-McNeil Pharmaceutical, Inc., OMP Division, Text of Proposed Labeling for Levaquin® (2004) 1-52.
Ortho-McNeil Pharmaceutical, Inc., Package Insert for Levaquin®, (2006) 15 pages.
Palmer et al., "Membrane-bound nitrate reductase is required for anaerobic growth in cystic fibrosis sputum", J Bacteriol. (2007) 189(12):4449-55. Epub Mar. 30, 2007.
Pellegrino et al., "Interpretative strategies for lung function tests", Eur Respir J. (2005) 26(5):948-968.
Perez et al., "CFTR inhibition mimics the cystic fibrosis inflammatory profile", Am J. Physiol. Lung Cell Mol Physiol, (2007) 292(2):L383-395. Epub Aug. 18, 2006.
"Physician's Desk Reference", 52.sup.nd ed., Medical Economics, Montvale, N.J. (1998).
Preston et al., "Pharmacodynamics of levofloxacin: a new paradigm for early clinical trials," JAMA. (1998) 279(2):125-129.
Querol-Ribelles et al., "Discrepancy between antibiotics administered in acute exacerbations of chronic bronchitis and susceptibility of isolated pathogens in respiratory samples: multicentre study in the primary care setting" International journal of antimicrobial agents (Netherlands) (2006) 28(5):472-6. (Abstract Only).
Ratcliffe et al., "Effects of Magnesium on the Activity of 4-Quinolone Antibacterial Agents", Journal of Pharmacy and Pharmacology, 1983, p. 61, vol. 35, Supplement Dec. 1983, The Pharmaceutical Society of Great Britain.
Reato et al., "Immunomodulating effect on antimicrobial agents on cytokine production by human polymorphonuclear neutrophils", International Journal of Antimicrobial Agents (2004) 23:150-154.
Rennard, "COPD: overview of definitions, epidemiology, and factors influencing its development", Chest (1998) 113 (Suppl 4):235-41s).
Romano et al., "[The use of ofloxacin in cystic fibrosis patients.] Uso dell'ofloxacin nei pazienti con fibrosi cistica", Minerva Pediatr. (1992) 44(3):79-86. (Abstract Only).
Rosell et al., 2005. Microbiologic determinants of exacerbation in chronic obstructive pulmonary disease. Arch Intern Med 165: 891-897.
Rosenfeld et al., "Defining a pulmonary exacerbation in cystic fibrosis", J Pediatr. (2001) 139(3):359-365.
Ross et al., Physicochemical properties of the fluoroquinolone antimicrobials V. effect of fluoroquinolone structure and pH on the complexation of various fluoroquinolones with magnesium and calcium ions, International Journal of Pharmaceutics (1993) 93:121-129.
Sabet et al., "Efficacy of Aerosol MP-376, a levofloxacin inhalation solution, in models of mouse lung infection due to *Pseudomonas aeruginosa*, Antimicrobial Agents and Chemotherapy", (2009) 53(9):3923-3928.
Sabet et al., "In-Vivo Antibacterial Activity of Aerosol MP-376 in Mouse Models of Pulmonary Infection", Pediatr. Pulmonol., (2007) 42(S30):304.
Sagel et al., "Sputum biomarkers of inflammation in cystic fibrosis lung disease", Proc. Am. Thorac. Soc. (2007) 4:406-417.
Sato, et al., "Antimicrobial activity of DU-6859, a new potent fluoroquinolone, against clinical isolates", Antimicrob Agents Chemother. (1992) 36(7):1491-1498.
Scheinberg et al., "Nebulized Antibiotics for the Treatment of Acute Exacerbations of Chronic Rhinosinusitis", Ear, Nose & Throat J. (2002) 81:648-652.
Seemungal et al., "Long-term erythromycin therapy is associated with decreased chronic obstructive pulmonary disease exacerbations", Am J Respir Crit Care Med (2008) 178:1139-1147.
Shalit et al., "Immunomodulatory and protective effects of moxifloxacin against candida albicans-induced bronchopneumonia in mice injected with cyclophosphamide", Antimicrobial Agents and Chemotherapy (2002) 46(8):2442-2449.
Shalit et al., "Anti-inflammatory effects of moxifloxacin on IL-8, IL-1B and TNF-a secretion and NFkB and MAP-kinase activation in human monocytes stimulated with *Aspergillus fumigatus*", Journal of Antimicrobial Chemotherapy (2006) 57:230-235.
Shinkai et al., "Clarithromycin has an immunomodulatory effect on ERK-mediated inflammation induced by *Pseudomonas aeruginosa* flagellin", Journal of Antimicrobial Chemotherapy (2007) 59:1096-1101.
Shinkai et al., "Macrolide antibiotics as immunomodulatory medications: Proposed mechanisms of action, Pharmacology & Therapeutics" (2008) 117:393-405.
Skauge et al., "Interaction Between Ciprofloxacin and DNA Mediated by Mg2+-ions", Inorganica Chimica Acta (2002) 339: 239-247.
Smith et al., "Chemistry and Mechanisms of Action of the Quinolone Antibacterials", The Quinolones, Academic Press Limited, Harcourt Brace Janovich, Publishers (1988) pp. 23-82.
Soler et al., "Airway inflammation and bronchial microbial patterns in patients with stable chronic obstructive pulmonary disease", Eur Respir J (1999) 14:1015-1022.
Stephenson, "Applications of x-ray powder diffraction in the pharmaceutical industry", The Rigaku Journal (2005) 22(1):2-15.
Stockley et al., "Relationship of sputum color to nature and outpatient management of acute exacerbations of COPD", Chest (2000) 117: 1638-1645.
Strieter, "Interleukin-8: a very important chemokine of the human airway epithelium", Am J Physiol Lung Cell Mol Physiol, (2002) 283:L688-689.
Suman et al., "Comparison of nasal deposition and clearance of aerosol generated by a nebulizer and an aqueous spray pump" Pharma Res. (1999) 16:1648-1652.
Suman et al., "Validity of in vitro tests on aqueous spray pumps as surrogates for nasal deposition", Pharmaceutical Research (2002) 19(1):1-6.
Suzuki et al., "Histopathological Study of the Effects of a Single Intratracheal Instillation of Surface Active Agents on Lung in Rats", The Journal of Toxicological Sciences (2000) 25(1):49-55.
Takeyama et al., "The 6-Fluoro-8-Methoxy Quinolone Gatifloxacin Down-Regulates Interleukin-8 Production in Prostate Cell Line PC-3", Antimicrobial Agents and Chemotherapy (2007) 51(1):162-168.
Takizawa et al., "Erythromycin Modulates IL-8 expression in normal and inflamed human bronchial epithelial cells", Am. J. Respir. Crit. Care Med. (1997) 156:266-271.
Traczewski et al., "In Vitro Activity of Doripenem Against *P. aeruginosa* and *Burkholderia cepacia* Isolates from Both Cystic Fibrosis and Non-cystic Fibrosis Patients," Antimicrob. Agents Chemother., (2006) 50:819-21.
Tsai et al., "Azitromycin blocks neutrophil recruitment in pseudomonas endobronchial infection", Am. J. respir Crit. Care Med. (2004) 170, pp. 1331-1339.
Tsapis et al., "Direct lung delivery of para-aminosalicylic acid by aerosol particles" Tuberculosis (Edinburgh, Scotland) (England) (2003) 83(6):379-85. (Abstract Only).
Turel et al., "Biological activity of some magnesium(II) complexes of quinolones", (2000) 7(2):101-104.
Vaughan et al., "Use of nebulized antibiotics for acute infections in chronic sinusitis", Otolaryngology—Head & Neck Surgery (2002) 127:558-68.
Vaughan, "Nebulization of antibiotics in management of sinusitis", Curr. Infect. Dis. Reports. (2004) 6:187-190.

(56) References Cited

OTHER PUBLICATIONS

Villeneuve et al., "Nebulized Magnesium Sulfate in the Management of Acute Exacerbations of Asthma", The Annals of Pharmacotherapy (2006) 40:1118.
Wada et al., "Immunomodulatory effect of gatifloxacin on mouse peritoneal macrophages in vitro and in models of endotoxin-induced rat conjunctivitis and rabbit bacterial keratitis", Opthalmic Res. (2008) 40:54-60.
Wahl et al. "New Medical Management Techniques for Acute Exacerbations of Chronic Rhinosinusitis", Curr Opin Otolaryngol Head Neck Surg. (2003) 11:27-32.
Wang et al. "Synthesis and crystal structure of a new copper (II) complex containing fluoroquinolone", Inter'l Symposium on Solid State Chemistry in China; Frontiers of Solid State Chemistry, World Scientific (2002) 327-332.
Weber et al., "Nebulizer Delivery of Tobramycin to the Lower Respiratory Tract", Pediatric Pulmonology, Wiley-Liss, Inc. (1994) 17: p. 331-339.
Weber et al. "Effect of nebulizer type and antibiotic concentration on device performance", Pediatric Pulmonology (1997) 23(4):249-260.
Weiss et al., "Anti-inflammatory effects of moxifloxacin on activated human monocytic cells: inhibition of NF-kB and mitogen-activated protein kinase activation and of synthesis of proinflammatory cytokines," Antimicrobial Agents and Chemotherapy, (2004) 48(6):1974-1982.
Werber et al., "Moxifloxacin inhibits cytokine-induced MAP kinase and NF-KB activation as well as nitric oxide synthesis in a human respiratory epithelial cell line", Journal of Antimicrobial Chemotherapy (2005) 55:293-300.
Wilkinson et al., "Airway bacterial load and $FEV_1$ decline in patients with chronic obstructive pulmonary disease", Am J Respir Crit Care Med (2003) 167:1090-1095.
Wilkinson et al., "Effect of interactions between lower airway bacterial and rhinoviral infection in exacerbations of COPD", Chest (2006) 129: 317-324.
Williams, "Fluoroquinolones for respiratory infections: too valuable to overuse", Chest (2001) 120:1771-1775.
Yamamoto et al., "Treatment of respiratory and urinary tract infections in elderly inmates at a nursing home by selective antimicrobial agents based on the sensitivity of the isolated bacteria" Nippon Ronen Igakkai zasshi. Japanese journal of geriatrics (Japan) (2007) 44(3):359-66. (Abstract Only).
Zach, M., "Discussion", Chest (1988) 94:160S-162S.
Zhang et al., "Besifloxacin, a novel fluoroquinolone antimicrobial agent, exhibits potent inhibition of pro-inflammatory cytokines in human THP-1 monocytes", Journal of Antimicrobial Chemotherapy (2008) 61:111-116.
Zhao et al., "Description and Clinical Treatment of an Early Outbreak of Severe Acute Respiratory Syndrome (SARS) in Guangzhou, PR China" Journal of Medical Microbio. (2003) 52(8):715-720.
Zheng et al., "Pulmonary delivery of a dopamine D-1 agonist, ABT-431, in dogs and humans" Int J Pharm. (1999) 191(2):131-40. (Abstract Only).
Zimmermann et al., "Anti-inflammatory effects of antibacterials on human bronchial epithelial cells," Respiratory Research (2009) 10(89):1-8.

International Preliminary Report on Patentability dated Nov. 29, 2007 for International Patent Application No. PCT/US2006/019351, filed May 18, 2006.
International Search Report and Written Opinion dated Oct. 20, 2006 for International Patent Application No. PCT/US2006/019351, filed May 18, 2006.
International Preliminary Report on Patentability dated Aug. 28, 2008 for International Patent Application No. PCT/US2007/003649, filed Feb. 12, 2007.
International Search Report and Written Opinion dated Oct. 25, 2007 for International Patent Application No. PCT/US2007/003649, filed Feb. 12, 2007.
International Preliminary Report on Patentability dated Aug. 31, 2010, for International Patent Application No. PCT/US2009/059740, filed Oct. 6, 2009.
International Search Report and Written Opinion dated Jan. 21, 2010, for International Patent Application No. PCT/US2009/059740, filed Oct. 6, 2009.
International Search Report and Written Opinion dated Dec. 17, 2009, for International Patent Application No. PCT/US2009/059744, filed Oct. 6, 2009.
International Preliminary Report on Patentability dated Apr. 12, 2011, for International Patent Application No. PCT/US2009/059744, filed Oct. 6, 2009.
International Search Report and Written Opinion dated Jul. 30, 2010, for International Patent Application No. PCT/US2010/032128, filed Apr. 22, 2010.
International Search Report and Written Opinion dated Dec. 7, 2010, for International Patent Application No. PCT/US2010/047903, filed Sep. 3, 2010.
International Search Report and Written Opinion dated Oct. 20, 2010, for International Patent Application No. PCT/US2010/002307, filed Aug. 19, 2010.
IPOS Search Report, Written Opinion and Invitation to Response to Written Opinion, dated Aug. 12, 2010 for Singapore Patent Application No. 200717702-5.
"Cystic Fibrosis," Medline Plus Medical Encyclopedia—accessed at www.nlm.nih.gov/medlineplus/ency/article/000107.htm on Jul. 11, 2008.
"Dynamic, absolute, kinematic viscosity" accessed online at www.engineeringtoolbox.com/dynamic-absolute-kinematicviscosity-d_412.html on Apr. 11, 2011.
Seddon, "Pseudopolymorph: a polemic", Crystal Growth & Design (2004) 4(6):1087, web release date Oct. 19, 2004.
"Surface Tension," The Engineering Toolbox—accessed at www.engineeringtoolbox.com/surface-tensiond_962.html on Jun. 21, 2011.
Vippagunta et al., "Crystalline Solids", Adv Drug Deliv Rev. (2001) 48(1):3-26.
Phase II , Multi-Center, Randomized, Double-Blind, Placebo-Controlled, Study to Evaluate the Safety, Tolerability and Efficacy of Three Dosage mens of M Solution for Inhalation 28 Days to Stable May 13, 2008, XP5503181 Retrieved from the Internet: URL:http://clinicaltrials,gov!archive/NCT00677365/2008_05 _ 13 [retrieved on Jul. 4, 2012].

* cited by examiner

FIG. 1

Comparison of Lung Levels after 10 mg/kg Aerosol Doses of Levofloxacin in Saline and Levofloxacin Formulated with Divalent Cations

*: p < 0.05 vs. untreated;  #: p<0.05 vs aztreonam;  ^: p = 0.056 vs. tobramycin

AEROSOL FLUOROQUINOLONE FORMULATIONS FOR IMPROVED PHARMACOKINETICS

RELATED APPLICATIONS

This application claims the benefit of U.S. Provisional Application No. 61/103,501 filed Oct. 7, 2008, which is hereby expressly incorporated by reference in its entirety.

FIELD OF THE INVENTION

The present invention relates to the field of antimicrobial agents. In particular, the present invention relates to the use of aerosolized fluoroquinolones formulated with divalent or trivalent cations with improved pulmonary availability for the treatment and management of bacterial infections of the lung and upper respiratory tract.

BACKGROUND

Gram-negative bacteria are intrinsically more resistant to antibiotics than gram-positive bacteria due to the presence of a second outer membrane, which provides an efficient barrier to both hydrophilic and hydrophobic compounds. Consequently, there are few classes of antibiotics available to treat Gram-negative infections. Indeed, only several representatives of beta-lactams, aminoglycosides and fluoroquinolones have in vitro anti-bacterial activity against *Pseudomonas aeruginosa* and have been shown to have clinical utility, not surprisingly, development of resistance to such antibiotics is well-documented.

Respiratory diseases afflict millions of people across the world leading to suffering, economic loss and premature death, including infections of acute, subacute and chronic duration of the nasal cavity or four sinuses (each which have left and right halves, the frontal, the maxillary the ethmoid and the sphenoid), or the larynx, trachea or lung (bronchi, bronchioles, alveoli).

Pulmonary infections caused by gram-negative bacteria represent a particular challenge. Causative agents are usually found in sputum, pulmonary epithelial lining fluid, alveolar macrophages and bronchial mucosa. Acute exacerbations of pulmonary infection, periodically observed in patients with cystic fibrosis, COPD, chronic bronchitis, bronchiectasis, acute and chronic pneumonias, and many other pulmonary infections. Prevention of these exacerbations as well as their treatment is often difficult especially when highly resistant pathogens such as *Pseudomonas aeruginosa* and *Burkholderia cepacia* complex are involved. For most treatment protocols, high doses are required to maintain effective concentrations at the site of infection. In the case of aminoglycosides, nephrotoxicity and ototoxicity are also directly related to prolonged elevations of serum antibiotic concentrations. In an attempt to achieve an optimal outcome for the patient, clinicians routinely use a combination of two or more antibiotics such as ceftazidime and tobramycin, which are administered at high doses for 2 weeks, with the aim of achieving antibiotic synergy (J. G. den Hollander, et al., "Synergism between tobramycin and ceftazidime against a resistant *Pseudomonas aeruginosa* strain, tested in an in vitro pharmacokinetic model" Antimicrob. Agents Chemother. (1997), 41, 95-100). For example, successful treatments require that ceftazidime be administered either every 8 hours or by continuous infusion to maximize the time that the serum concentration is above the minimum inhibitory concentration (M. Cazzola, et al., "Delivering antibacterials to the lungs: Considerations for optimizing outcomes" Am. J. Respir. Med. (2002), 1, 261-272).

Aerosol administration of antibiotics directly to the site of infection, ensuring high local concentrations coupled with low systemic exposure represent an attractive alternative for the treatment of pulmonary infections. Aerosolized tobramycin is used for treatment of pseudomonal bacterial infections in patients with cystic fibrosis. The rationale behind this technique is to administer the drug directly to the site of infection and thereby alleviate the need to produce high serum concentrations by the standard intravenous method. An advantage of aerosol administration is that many patients can self-administer the antibiotic, and this treatment method may negate the need for lengthy hospitalization (M. E. Hodson "Antibiotic treatment: Aerosol therapy", Chest (1988), 94, 156S-160S; and M. S. Zach "Antibiotic aerosol treatment" Chest (1988), 94, 160S-162S). However, tobramycin is currently the only FDA-approved aerosol antibiotic in the United States. And while it continues to play an important role in the management of recurrent infections in cystic fibrosis patients, its clinical utility is inadvertently being diminished due to development of resistance. In addition, the impact of total high concentrations achieved after aerosol administration is being somewhat diminished due to high binding of tobramycin to the components of cystic fibrosis sputum. Thus, there is a need for improved aerosolized antibiotics.

SUMMARY

The present invention relates to the use of aerosolized fluoroquinolones formulated with divalent or trivalent cations having improved pulmonary availability for the treatment and management of bacterial infections of the lung and upper respiratory tract. Some methods include treating a pulmonary infection including administering to a subject in need thereof, an effective amount of an aerosol solution of levofloxacin or ofloxacin in combination with a divalent or trivalent cation with improved pulmonary availability and exposure to levofloxacin or ofloxacin.

Methods for treating a pulmonary infection are provided. Some such methods include administering to a human having a pulmonary infection an aerosol of a solution comprising levofloxacin or ofloxacin and a divalent or trivalent cation to achieve a maximum lung sputum concentration ($C_{max}$) of at least 1200 mg/L and a lung sputum area under the curve (AUC) of at least 1500 h·mg/L. In more embodiments, methods for treating a chronic lung infection are provided. Some such methods can include administering to a subject having a chronic lung infection an aerosol of a solution comprising levofloxacin or ofloxacin and a divalent or trivalent cation. In more embodiments, pharmaceutical compositions are provided. Some such compositions can include an aqueous solution consisting essentially of from 80 mg/ml to 120 mg/ml levofloxacin or ofloxacin and from 160 mM to 220 mM of a divalent or trivalent cation, wherein the solution has a pH from 5 to 7 and an osmolality from 300 mOsmol/kg to 500 mOsmol/kg.

Some embodiments include methods for treating a pulmonary infection that include administering to a human having said pulmonary infection an aerosol of a solution that includes levofloxacin or ofloxacin and a divalent or trivalent cation to achieve a maximum lung sputum concentration ($C_{max}$) of at least about 1200 mg/L and a lung sputum area under the curve (AUC) of at least about 1500 h·mg/L.

Some embodiments include methods of treating a chronic lung infection that include administering to a subject having a chronic lung infection an aerosol of a solution that includes levofloxacin or ofloxacin and a divalent or trivalent cation.

Some embodiments include pharmaceutical compositions that include an aqueous solution consisting essentially of from about 80 mg/ml to about 120 mg/ml levofloxacin or ofloxacin and from about 160 mM to about 240 mM of a divalent or trivalent cation, wherein the solution has a pH from about 5 to about 7 and an osmolality from about 300 mOsmol/kg to about 500 mOsmol/kg.

BRIEF DESCRIPTION OF THE DRAWINGS

FIG. 1 shows a graph of plasma levofloxacin concentration in rats after intravenous administration, aerosol administration of levofloxacin (LVX) formulated in saline, or aerosol administration of levofloxacin formulated with $MgCl_2$.

FIG. 2 shows a graph of recovery of levofloxacin from lung homogenate in rats after a single 10 mg/kg dose of aerosol levofloxacin formulated with saline, $Ca^{+2}$, $Mg^{+2}$ or $Zn^{2+}$.

FIG. 14 shows a graph of mean sputum levofloxacin levels in cystic fibrosis patients following a single nebulized dose of levofloxacin formulated in saline compared to formulation in a solution of magnesium chloride. Both formulations were nebulized using a Pari eFlow nebulizer using vibrating mesh technology with the same mesh head design and pore size. The nebulizer loaded dose of levofloxacin in saline was 87 mg and the nebulizer loaded dose of levofloxacin was 180 mg for the formulation using magnesium chloride. Data were normalized to an 87 mg dose by multiplying the observed sputum levofloxacin concentrations obtained with the magnesium chloride formulation by 87/180 (0.48).

DETAILED DESCRIPTION

Figure 3:
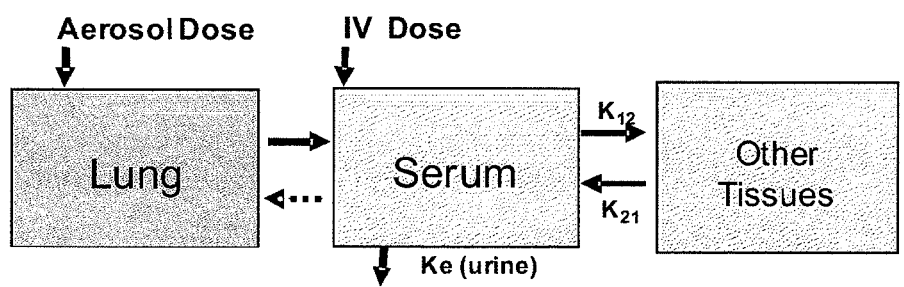
FIG. 3 shows a schematic of a pharmacokinetic model for deconvolution of serum levofloxacin concentrations following aerosol administration of a drug.

The present invention relates to the field of antimicrobial agents. In particular, the present invention relates to the use of aerosolized fluoroquinolones formulated with divalent or trivalent cations having improved pulmonary availability and thus better bactericidal activity for the treatment and management of bacterial infections of the lung and upper respiratory tract.

Many of the problems associated with antimicrobial-resistant pathogens could be alleviated if the concentration of the antimicrobial could be safely increased at the site of infection. For example, pulmonary infections may be treated by administration of the antimicrobial agent, at high concentrations directly to the site of infection without incurring large systemic concentrations of the antimicrobial. Accordingly, some embodiments disclosed herein are improved methods for delivering drug compositions to treat pulmonary bacterial infections. More specifically, described herein are formulations of fluoroquinolones with divalent or trivalent cations that achieve a desirable pharmacokinetic profile of the fluoroquinolone in humans beneficial for increasing efficacy and reducing the emergence of drug resistance.

Accordingly, some embodiments described herein include methods and compositions that include fluoroquinolones where absorption from lung tissue or the upper airway into systemic circulation after aerosol is retarded. In some such embodiments, fluoroquinolones are complexed with divalent cations in a manner that does not significantly diminish their antimicrobial activity. Such complexes may be for the treatment, maintenance or prevention of infection. In addition, such complexes can show higher concentrations of drug at the sites of infection (e.g., the upper and/or lower respiratory system), and higher efficacy, compared to a fluoroquinolone not combined with divalent or trivalent cations.

Some embodiments of the present invention relate to methods for treating a pulmonary infection, and compositions of levofloxacin or ofloxacin formulated with a divalent or trivalent cation. It has been discovered that particular methods and compositions described herein achieve an improved availability of levofloxacin or ofloxacin in the lungs of subjects. An increased availability in the lungs of antimicrobial agents is useful in the treatment of pulmonary infections, and is particularly advantageous in the treatment of conditions such as cystic fibrosis and chronic obstructive pulmonary disorders, including for example, chronic bronchitis, bronchiectasis, and some asthmas.

Improved availability in the lung can be indicated using a variety of pharmodynamic-pharmacokinetic parameters relating to factors such as increased concentration of a drug in the lung and/or length of time a drug is retained in the lung. Such factors can include lung sputum area under curve (AUC), and maximum lung sputum concentration ($C_{max}$).

Typically, administering aerosolized antimicrobial agents to the lungs can provide high concentrations in the lungs without incurring high systemic concentrations. However, the methods and compositions provided herein achieve unexpectedly increased availability in the lungs.

Generally, the compositions provided herein can comprise solutions of levofloxacin or ofloxacin formulated with a divalent or trivalent cation, such as $Mg^{2+}$. In some embodiments, the compositions can lack a particular excipient, such as lactose. The compositions may be administered using devices such as nebulizers or a microspray aerosol device inserted directly into the trachea of animals, and can be used to treat a wide variety of bacteria. In addition, methods and compositions provided herein can include additional active agents useful in the treatment of pulmonary infections, and disorders associated with pulmonary infections, such as cystic fibrosis, and chronic obstructive pulmonary disease, including chronic bronchitis and some asthmas.

Definitions

The term "administration" or "administering" refers to a method of giving a dosage of an antimicrobial pharmaceutical composition to a vertebrate. The preferred method of administration can vary depending on various factors, e.g., the components of the pharmaceutical composition, the site of the potential or actual bacterial infection, the microbe involved, and the severity of an actual microbial infection.

A "carrier" or "excipient" is a compound or material used to facilitate administration of the compound, for example, to increase the solubility of the compound. Solid carriers include, e.g., starch, lactose, dicalcium phosphate, sucrose, and kaolin. Liquid carriers include, e.g., sterile water, saline, buffers, non-ionic surfactants, and edible oils such as oil, peanut and sesame oils. In addition, various adjuvants such as are commonly used in the art may be included. These and other such compounds are described in the literature, e.g., in the Merck Index, Merck & Company, Rahway, N.J. Considerations for the inclusion of various components in pharmaceutical compositions are described, e.g., in Gilman et al. (Eds.) (1990); Goodman and Gilman's: The Pharmacological Basis of Therapeutics, 8th Ed., Pergamon Press, incorporated by reference herein in its entirety.

A "diagnostic" as used herein is a compound, method, system, or device that assists in the identification and characterization of a health or disease state. The diagnostic can be used in standard assays as is known in the art.

The term "mammal" is used in its usual biological sense. Thus, it specifically includes humans, cattle, horses, dogs, and cats, but also includes many other species.

The term "microbial infection" refers to the undesired proliferation or presence of invasion of pathogenic microbes in a host organism. This includes the excessive growth of microbes that are normally present in or on the body of a mammal or other organism. More generally, a microbial infection can be any situation in which the presence of a microbial population(s) is damaging to a host mammal. Thus, a microbial infection exists when excessive numbers of a microbial population are present in or on a mammal's body, or when the effects of the presence of a microbial population(s) is damaging the cells or other tissue of a mammal.

The term "pharmaceutically acceptable carrier" or "pharmaceutically acceptable excipient" includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the active ingredient, its use in the therapeutic compositions is contemplated. Supplementary active ingredients can also be incorporated into the compositions.

The term "pharmaceutically acceptable salt" refers to salts that retain the biological effectiveness and properties of the compounds of this invention and, which are not biologically or otherwise undesirable. In many cases, the compounds of this invention are capable of forming acid and/or base salts by virtue of the presence of amino and/or carboxyl groups or groups similar thereto. Pharmaceutically acceptable acid addition salts can be formed with inorganic acids and organic acids. Inorganic acids from which salts can be derived include, for example, hydrochloric acid, hydrobromic acid, sulfuric acid, nitric acid, phosphoric acid, and the like. Organic acids from which salts can be derived include, for example, acetic acid, propionic acid, naphtoic acid, oleic acid, palmitic acid, pamoic (emboic) acid, stearic acid, glycolic acid, pyruvic acid, oxalic acid, maleic acid, malonic acid, succinic acid, fumaric acid, tartaric acid, citric acid, ascorbic acid, glucoheptonic acid, glucuronic acid, lactic acid, lactobioic acid, tartaric acid, benzoic acid, cinnamic acid, mandelic acid, methanesulfonic acid, ethanesulfonic acid, p-toluenesulfonic acid, salicylic acid, and the like. Pharmaceutically acceptable base addition salts can be formed with inorganic and organic bases. Inorganic bases from which salts can be derived include, for example, sodium, potassium, lithium, ammonium, calcium, magnesium, iron, zinc, copper, manganese, aluminum, and the like; particularly preferred are the ammonium, potassium, sodium, calcium and magnesium salts. Organic bases from which salts can be derived include, for example, primary, secondary, and tertiary amines, substituted amines including naturally occurring substituted amines, cyclic amines, basic ion exchange resins, and the like, specifically such as isopropylamine, trimethylamine, diethylamine, triethylamine, tripropylamine, histidine, arginine, lysine, benethamine, N-methyl-glucamine, and ethanolamine. Other acids include dodecylsufuric acid, naphthalene-1,5-disulfonic acid, naphthalene-2-sulfonic acid, and saccharin.

"Solvate" refers to the compound formed by the interaction of a solvent and fluoroquinolone antimicrobial, a metabolite, or salt thereof. Suitable solvates are pharmaceutically acceptable solvates including hydrates.

In the context of the response of a microbe, such as a bacterium, to an antimicrobial agent, the term "susceptibility" refers to the sensitivity of the microbe for the presence of the antimicrobial agent. So, to increase the susceptibility means that the microbe will be inhibited by a lower concentration of the antimicrobial agent in the medium surrounding the microbial cells. This is equivalent to saying that the microbe is more sensitive to the antimicrobial agent. In most cases the minimum inhibitory concentration (MIC) of that antimicrobial agent will have been reduced. The $MIC_{90}$ can include the concentration to inhibit growth in 90% of organisms.

By "therapeutically effective amount" or "pharmaceutically effective amount" is meant a fluoroquinolone antimicrobial agent, as disclosed for this invention, which has a therapeutic effect. The doses of fluoroquinolone antimicrobial agent which are useful in treatment are therapeutically effective amounts. Thus, as used herein, a therapeutically effective amount means those amounts of fluoroquinolone antimicrobial agent which produce the desired therapeutic effect as judged by clinical trial results and/or model animal infection studies. In particular embodiments, the fluoroquinolone antimicrobial agent are administered in a pre-determined dose, and thus a therapeutically effective amount would be an amount of the dose administered. This amount and the amount of the fluoroquinolone antimicrobial agent can be routinely determined by one of skill in the art, and will vary, depending on several factors, such as the particular microbial strain involved. This amount can further depend upon the patient's height, weight, sex, age and medical history. For prophylactic treatments, a therapeutically effective amount is that amount which would be effective to prevent a microbial infection.

A "therapeutic effect" relieves, to some extent, one or more of the symptoms of the infection, and includes curing an infection. "Curing" means that the symptoms of active infection are eliminated, including the total or substantial elimination of excessive members of viable microbe of those involved in the infection to a point at or below the threshold of detection by traditional measurements. However, certain long-term or permanent effects of the acute or chronic infection may exist even after a cure is obtained (such as extensive tissue damage). As used herein, a "therapeutic effect" is defined as a statistically significant reduction in bacterial load in a host, emergence of resistance, pulmonary function, or improvement in infection symptoms or functional status as measured by human clinical results or animal studies.

"Treat," "treatment," or "treating," as used herein refers to administering a pharmaceutical composition for prophylactic and/or therapeutic purposes. The term "prophylactic treatment" refers to treating a patient who is not yet infected, but who is susceptible to, or otherwise at risk of, a particular infection such that there is a reduced onset of infection. The term "therapeutic treatment" refers to administering treatment to a patient already suffering from an infection that may be acute or chronic. Treatment may eliminate the pathogen, or it may reduce the pathogen load in the tissues that results in improvements measured by patients symptoms or measures of lung function. Thus, in preferred embodiments, treating is the administration to a mammal (either for therapeutic or prophylactic purposes) of therapeutically effective amounts of a fluoroquinolone antimicrobial agent.

Pharmacokinetics (PK) is concerned with the time course of antimicrobial concentration in the body. Pharmacodynamics (PD) is concerned with the relationship between pharmacokinetics and the antimicrobial efficacy in vivo. PK/PD parameters correlate antimicrobial exposure with antimicrobial activity. The rate of killing by antimicrobial is dependent on antimicrobial mode of action and is determined by either the length of time necessary to kill (time-dependent) or the effect of increasing concentrations alone (concentration-dependent) or integrated over time as an area under the concentration-time curve (AUC). To predict the therapeutic efficacy of antimicrobials with diverse mechanisms of action different PK/PD parameters may be used. PK/PD parameters may be used to determine the availability of antimicrobial compositions, for example, availability of a antimicrobial agent in a composition in the pulmonary system, and/or bioavailability of a antimicrobial agent in a composition in plasma/serum.

"AUC/MIC ratio" is one example of a PK/PD parameter. AUC is defined as the area under the plasma/serum or site-of-infection concentration-time curve of an antimicrobial agent in vivo (in animal or human). For example, the site of infection and/or the site where concentration is measured can include portions of the pulmonary system, such as bronchial fluid and/or sputum. Accordingly, AUC may be a serum AUC, or a pulmonary AUC based on concentrations in serum and pulmonary tissues (sputum, epithelial lining fluid, or homogenates of whole tissue). $AUC_{(0-t)}$ can include the area under curve for time zero to a specific time 't.' $AUC_{(0-inf)}$ can include the area under curve from time zero to infinity. AUC/MIC ratio is determined by dividing the 24-hour-AUC for an individual antimicrobial by the MIC for the same antimicrobial determined in vitro. Activity of antimicrobials with the dose-dependent killing (such as fluoroquinolones) is well predicted by the magnitude of the AUC/MIC ratio. The AUC:MIC ratio can also prevent selection of drug-resistant bacteria.

"$C_{max}$:MIC" ratio is another PK:PD parameter. It describes the maximum drug concentration in plasma or tissue relative to the MIC. Fluoroquinolones and aminoglycosides are examples where $C_{max}$:MIC may predict in vivo bacterial killing where resistance can be suppressed.

"Time above MIC" (T>MIC) is another PK/PD parameter. It is expressed a percentage of a dosage interval in which the plasma or site-of-infection level exceeds the MIC. Activity of antimicrobials with the time-dependent killing (such as beta-lactams or monobactam antibiotics) is well predicted by the magnitude of the T>MIC ratio.

The term "dosing interval" refers to the time between administrations of the two sequential doses of a pharmaceutical's during multiple dosing regimens. For example, in the case of orally administered ciprofloxacin, which is administered twice daily (traditional regimen of 400 mg b.i.d) and orally administered levofloxacin, which is administered once a day (500 mg or 750 mg q.d.), the dosing intervals are 12 hours and 24 hours, respectively.

As used herein, the "peak period" of a pharmaceutical's in vivo concentration is defined as that time of the pharmaceutical dosing interval when the pharmaceutical concentration is not less than 50% of its maximum plasma or site-of-infection concentration. In some embodiments, "peak period" is used to describe an interval of antimicrobial dosing.

The estimated "respirable delivered dose" is the dose or amount of drug delivered to the lung of a patient using a nebulizer or other aerosol delivery device. The RDD is estimated from the inspiratory phase of a breath simulation device programmed to the European Standard pattern of 15 breaths per minute, with an inspiration to expiration ratio of 1:1, and measurement of particles emitted from a nebulizer with a size of about 5 microns or less.

Improved Availability

The antibiotic rate of killing is dependent upon antibiotic mode of action and is determined by either the length of time necessary for the antibiotic to kill (time-dependent) or the effect of increasing the antibiotic concentration (concentration-dependent). Fluoroquinolones are characterized by concentration-dependent, time-kill activity where a therapeutic effect requires a high local peak concentration above the MICs of the infecting pathogen.

Fluoroquinolone efficacy in humans, animals and in vitro models of infection is linked to AUC:MIC ratio and $C_{max}$:MIC ratio. A number of in vitro studies have been conducted to determine if high concentrations of levofloxacin with an extremely short half-lives (as predicted from a rat and human PK model) in a target tissues resulted in bacterial killing superior to that seen under conditions with more prolonged residence times. In these studies, levofloxacin concentrations that were 0.018-fold-1024-fold the MIC were evaluated in a standard kill-curve and an in vitro hollow fiber assay. In both of these assays, high concentrations of levofloxacin were rapidly bactericidal and reached their maximum levels of killing in 10-20 minutes. This level of killing was sustained whether levofloxacin was maintained at that level or given a half-life of 10 minutes. In addition, no resistance was observed. Accordingly, high doses and rapid delivery of specially formulated levofloxacin is rapidly bactericidal for susceptible organisms and resistant organisms.

In one embodiment, the concentration of levofloxacin at the site of infection is increased by delivering levofloxacin in combination with divalent or trivalent cations directly to the lung using inhalation therapy, thereby decreasing the amount of time levofloxacin is in the "mutant selection window" (MSW). Such a therapeutic approach achieves broader coverage of pathogens (including levofloxacin resistant strains), prevents further resistance development, and results in shorter courses of levofloxacin therapy.

Some embodiments include compositions of levofloxacin or ofloxacin having an improved pulmonary availability, wherein an increased pulmonary AUC is indicative of the improved pulmonary availability of the levofloxacin or ofloxacin. In some embodiments, the increase can be at least about 10%, 20, 30, 40%, 50%, 75%, 100%, 150%, 200%, 250%, 300%, and 500%. An increase can be relative to, for example, a composition lacking a divalent or trivalent cation, and/or a composition having certain excipients (e.g., lactose), and/or a composition delivered to the lung at a certain rate, and/or a certain respirable delivered dose. In some embodiments, methods are provided that include achieving an improved pulmonary availability indicated by a lung AUC greater than about 400 h·mg/L, about 500 h·mg/L, about 600 h·mg/L, about 700 h·mg/L, about 800 h·mg/L, about 900 h·mg/L, about 1000 h·mg/L, about 1100 h·mg/L, about 1200 h·mg/L, about 1300 h·mg/L, about 1400 h·mg/L, about 1500 h·mg/L, about 1600 h·mg/L, about 1700 h·mg/L, about 1800 h·mg/L, about 1900 h·mg/L, about 2000 h·mg/L, about 2100 h·mg/L, about 2200 h·mg/L, about 2300 h·mg/L, about 2400 h·mg/L, about 2500 h·mg/L, about 2600 h·mg/L, about 2700 h·mg/L, about 2800 h·mg/L, about 2900 h·mg/L, about 3000 h·mg/L, about 3100 h·mg/L, about 3200 h·mg/L, about 3300 h·mg/L, about 3400 h·mg/L, about 3500 h·mg/L, about 3600 h·mg/L, about 3700 h·mg/L, about 3800 h·mg/L, about 3900 h·mg/L, about 4000 h·mg/L, about 4100 h·mg/L, about 4200 h·mg/L, about 4300 h·mg/L, about 4400 h·mg/L, and about 4500 h·mg/L. The increase can be measured for example, in bronchial fluid, homogenates of whole lung tissue, or in sputum.

In more embodiments, an increased pulmonary $C_{max}$ can be indicative of an improved pulmonary availability for a formulation of levofloxacin or ofloxacin. In some such embodiments, the increase can be at least about 50%, 75%, 100%, and 150%. An increase can be relative to a composition, for example, lacking a divalent or trivalent cation, and/or a composition having certain excipients (e.g., lactose), and/or a composition delivered to the lung at a certain rate, and/or a certain respirable delivered dose. In some embodiments, methods are provided that include achieving an improved pulmonary availability indicated by a lung $C_{max}$ greater than about 300 mg/L, about 400 mg/L, about 500 mg/L, about 600 mg/L, about 700 mg/L, about 800 mg/L, about 900 mg/L, about 1000 mg/L, about 1100 mg/L, about 1200 mg/L, about 1300 mg/L, about 1400 mg/L, about 1500 mg/L, about 1600 mg/L, about 1700 mg/L, about 1800 mg/L, about 1900 mg/L, about 2000 mg/L, about 2100 mg/L, about 2200 mg/L, about 2300 mg/L, about 2400 mg/L, about 2500 mg/L, about 2600 mg/L, about 2700 mg/L, about 2800 mg/L, about 2900 mg/L, about 3000 mg/L, about 3100 mg/L, about 3200 mg/L, about 3300 mg/L, about 3400 mg/L, about 3500 mg/L, about 3600 mg/L, about 3700 mg/L, about 3800 mg/L, about 3900 mg/L, about 4000 mg/L, about 4100 mg/L, about 4200 mg/L, about 4300 mg/L, about 4400 mg/L, about 4500 mg/L, about 4600 mg/L, about 4700 mg/L, about 4800 mg/L, about 4900 mg/L, and 5000 mg/L. The increase can be measured for example, in bronchial secretions, epithelial lining fluid, lung homogenates, and in sputum.

In even more embodiments, a decrease in serum AUC or serum $C_{max}$ can be indicative of an increase in the pulmonary availability and prolonged exposure of a levofloxacin or ofloxacin using a formulation. In some such embodiments, the decrease can be at least about 1%, 5%, 10, 20%, or 50%. A decrease can be relative to a composition, for example, lacking a divalent or trivalent cation, and/or a composition having certain excipients (e.g., lactose), and/or a composition delivered to the lung at a certain rate as a solution or other composition. In some embodiments, a formulation of levofloxacin can be characterized by a AUC:$MIC_{90}$ greater than about 200, 300, 400, 500, 600, 700, 800, 900, and 1000. In some such embodiments, the AUC can be pulmonary AUC.

In some embodiments, the concentrations in lung tissue (sputum, ELF, tissue homogenates) can be characterized by the PK-PD indice $C_{max}$:$MIC_{90}$ greater than about 20, 40, 60, 80, 100, 120, 140, 160, 180, 200, 220, 240, 260, 280, 300, 320, 340, 340, 360, 380, 400, 420, 440, 460, 480, 500, 520, 540, 560, 580, and 600.

The increase or decrease in a parameter to measure improved availability of a formulation of levofloxacin or ofloxacin can be relative to a formulation of levofloxacin or ofloxacin lacking divalent or trivalent cations, relative to a formulation of levofloxacin or ofloxacin lacking lactose, and/or relative to a formulation of with a lower concentration of levofloxacin or ofloxacin.

Methods of Treatment or Prophylaxis

In some embodiments, a method is provided for treating a microbial infection in an animal, specifically including in a mammal, by treating an animal suffering from such an lung infection with a fluoroquinolone antimicrobial formulated with a divalent or trivalent cation and having improved pulmonary availability. In some embodiments, fluoroquinolone antimicrobials may be administered following aerosol formation and inhalation. Thus, this method of treatment is especially appropriate for the treatment of pulmonary infections involving microbial strains that are difficult to treat using an antimicrobial agent delivered orally or parenterally due to the need for high dose levels (which can cause undesirable side effects), or due to lack of any clinically effective antimicrobial agents. In one such embodiment, this method may be used to administer a fluoroquinolone antimicrobial directly to the site of infection. Such a method may reduce systemic exposure and maximizes the amount of antimicrobial agent to the site of microbial infection. This method is also appropriate for treating infections involving microbes that are susceptible to fluoroquinolone antimicrobials as a way of reducing the frequency of selection of resistant microbes. This method is also appropriate for treating infections involving microbes that are otherwise resistant to fluoroquinolone antimicrobials as a way of increasing the amount of antimicrobial at the site of microbial infection. A subject may be identified as infected with bacteria that are capable of developing resistance by diagnosing the subject as having symptoms that are characteristic of a bacterial infection with a bacteria species known to have resistant strains or a with a bacteria that is a member of group that are known to have resistant strains. Alternatively, the bacteria may be cultured and identified as a species known to have resistant strains or a bacteria that is a member of group that are known to have resistant strains.

In some embodiments, the aerosol fluoroquinolone antimicrobial agent formulated with divalent or trivalent cations is administered at a level sufficient to overcome the emergence resistance in bacteria or increase killing efficiency such that resistance does not have the opportunity to develop.

In some embodiments, the aerosol fluoroquinolone therapy may be administered as a treatment or prophylaxis in combination or alternating therapeutic sequence with other aerosol, oral or parenteral antibiotics. By non-limiting example this may include aerosol tobramycin and/or other aminoglycoside, aerosol aztreonam and/or other beta or monobactam, aerosol ciprofloxacin and/or other fluoroquinolones, aerosol azithromycin and/or other macrolides or ketolides, tetracycline and/or other tetracyclines, quinupristin and/or other streptogramins, linezolid and/or other oxazolidinones, vancomycin and/or other glycopeptides, and chloramphenicol and/or other phenicols, and colisitin and/or other polymyxins.

In addition, compositions and methods provided herein can include the aerosol fluoroquinolone therapy administered as a treatment or prophylaxis in combination or alternating therapeutic sequence with an additional active agent. As discussed above, some such additional agents can include antibiotics. More additional agents can include bronchodilators, anticholinergics, glucocorticoids, eicosanoid inhibitors, and combinations thereof. Examples of bronchodilators include salbutamol, levosalbuterol, terbutaline, fenoterol, terbutlaine, pirbuterol, procaterol, bitolterol, rimiterol, carbuterol, tulobuterol, reproterol, salmeterol, formoterol, arformoterol, bambuterol, clenbuterol, indacterol, theophylline, roflumilast, cilomilast. Examples of anticholinergics include ipratropium, and tiotropium. Examples of glucocorticoids include prednisone, fluticasone, budesonide, mometasone, ciclesonide, and beclomethasone. Examples of eicosanoids include montelukast, pranlukast, zafirlukast, zileuton, ramatroban, and seratrodast. More additional agents can include pulmozyme, hypertonic saline, agents that restore chloride channel function in CF, inhaled beta-agonists, inhaled antimuscarinic agents, inhaled corticosteroids, and inhaled or oral phosphodiesterase inhibitors. More additional agents can include CFTR modulators, for example, VX-770, atluren, VX-809. More additional agents can include agents to restore airway surface liquid, for example, denufosol, mannitol, GS-9411, and SPI-8811 More additional agents can include anti-inflammatory agents, for example, ibuprofen, sildenafil, and simavastatin.

Pharmaceutical Compositions

For purposes of the method described herein, a fluoroquinolone antimicrobial agent formulated with a divalent or trivalent cation having improved pulmonary availability may be administered using an inhaler. In some embodiments, a fluoroquinolone antimicrobial disclosed herein is produced as a pharmaceutical composition suitable for aerosol formation, good taste, storage stability, and patient safety and tolerability. In some embodiments, the isoform content of the manufactured fluoroquinolone may be optimized for tolerability, antimicrobial activity and stability.

Formulations can include a divalent or trivalent cation. The divalent or trivalent cation can include, for example, magnesium, calcium, zinc, copper, aluminum, and iron. In some embodiments, the solution comprises magnesium chloride, magnesium sulfate, zinc chloride, or copper chloride. In some embodiments, the divalent or trivalent cation concentration can be from about 25 mM to about 400 mM, from about 50 mM to about 400 mM, from about 100 mM to about 300 mM, from about 100 mM to about 250 mM, from about 125 mM to about 250 mM, from about 150 mM to about 250 mM, from about 175 mM to about 225 mM, from about 180 mM to about 220 mM, and from about 190 mM to about 210 mM. In some embodiments, the concentration is about 200 mM. In some embodiments, the magnesium chloride, magnesium sulfate, zinc chloride, or copper chloride can have a concentration from about 5% to about 25%, from about 10% to about 20%, and from about 15% to about 20%. In some embodiments, the ratio of fluoroquinolone to divalent or trivalent cation can be 1:1 to 2:1 or 1:1 to 1:2.

Non-limiting fluoroquinolones for use as described herein include levofloxacin, ofloxacin, ciprofloxacin, enoxacin, gatifloxacin, gemifloxacin, lomefloxacin, moxifloxacin, norfloxacin, pefloxacin, sparfloxacin, garenoxacin, sitafloxacin, and DX-619.

The formulation can have a fluoroquinolone concentration, for example, levofloxacin or ofloxacin, greater than about 50 mg/ml, about 60 mg/ml, about 70 mg/ml, about 80 mg/ml, about 90 mg/ml, about 100 mg/ml, about 110 mg/ml, about 120 mg/ml, about 130 mg/ml, about 140 mg/ml, about 150 mg/ml, about 160 mg/ml, about 170 mg/ml, about 180 mg/ml, about 190 mg/ml, and about 200 mg/ml. In some embodiments, the formulation can have a fluoroquinolone concentration, for example, levofloxacin or ofloxacin, from about 50 mg/ml to about 200 mg/ml, from about 75 mg/ml to about 150 mg/ml, from about 80 mg/ml to about 125 mg/ml, from about 80 mg/ml to about 120 mg/ml, from about 90 mg/ml to about 125 mg/ml, from about 90 mg/ml to about 120 mg/ml, and from about 90 mg/ml to about 110 mg/ml. In some embodiments, the concentration is about 100 mg/ml.

The formulation can have an osmolality from about 300 mOsmol/kg to about 500 mOsmol/kg, from about 325 mOsmol/kg to about 450 mOsmol/kg, from about 350 mOsmol/kg to about 425 mOsmol/kg, and from about 350 mOsmol/kg to about 400 mOsmol/kg. In some embodiments, the osmolality of the formulation is greater than about 300 mOsmol/kg, about 325 mOsmol/kg, about 350 mOsmol/kg, about 375 mOsmol/kg, about 400 mOsmol/kg, about 425 mOsmol/kg, about 450 mOsmol/kg, about 475 mOsmol/kg, and about 500 mOsmol/kg.

The formulation can have a pH from about 4.5 to about 8.5, from about 5.0 to about 8.0, from about 5.0 to about 7.0, from about 5.0 to about 6.5, from about 5.5 to about 6.5, and from 6.0 to about 6.5.

The formulation can comprise a conventional pharmaceutical carrier, excipient or the like (e.g., mannitol, lactose, starch, magnesium stearate, sodium saccharine, talcum, cellulose, sodium crosscarmellose, glucose, gelatin, sucrose, magnesium carbonate, and the like), or auxiliary substances such as wetting agents, emulsifying agents, solubilizing agents, pH buffering agents and the like (e.g., sodium acetate, sodium citrate, cyclodextrine derivatives, sorbitan monolaurate, triethanolamine acetate, triethanolamine oleate, and the like). In some embodiments, the formulation can lack a conventional pharmaceutical carrier, excipient or the like. Some embodiments include a formulation lacking lactose. Some embodiments comprise lactose at a concentration less than about 10%, 5%, 1%, or 0.1%. In some embodiments, the formulation can consist essentially of levofloxacin or ofloxacin and a divalent or trivalent cation.

In some embodiments, a formulation can comprise a levofloxacin concentration between about 75 mg/ml to about 150 mg/ml, a magnesium chloride concentration between about 150 mM to about 250 mM, a pH between about 5 to about 7; an osmolality of between about 300 mOsmol/kg to about 600 mOsmol/kg, and lacks lactose.

In some embodiments, a formulation comprises a levofloxacin concentration of about 100 mg/ml, a magnesium chloride concentration of about 200 mM, a pH of about 6.2, an osmolality of about 383 mOsmol/kg, and lacks lactose. In some embodiments, a formulation consists essentially of a levofloxacin concentration of about 90 mg/ml to about 110 mg/ml, a magnesium chloride concentration of about 180 mM to about 220 mM, a pH of about 5 to about 7, an osmolality of about 300 mOsmol/kg to 500 mOsmol/kg, and lacks lactose.

Administration

The fluoroquinolone antimicrobials formulated with divalent or trivalent cations and having improved pulmonary availability may be administered at a therapeutically effective dosage, e.g., a dosage sufficient to provide treatment for the disease states previously described. The amount of active compound administered will, of course, be dependent on the subject and disease state being treated, the severity of the affliction, the manner and schedule of administration and the judgment of the prescribing physician; for example, a likely dose range for aerosol administration of levofloxacin would be about 20 to 300 mg per day, the active agents being selected for longer or shorter pulmonary half-lives, respectively. In some embodiments, a likely dose range for aerosol administration of levofloxacin would be about 20 to 300 mg BID (twice daily).

Administration of the fluoroquinolone antimicrobial agents disclosed herein or the pharmaceutically acceptable salts thereof can be via any of the accepted modes of administration for agents that serve similar utilities including, but not limited to, aerosol inhalation. Methods, devices and compositions for delivery are described in U.S. Patent Application Publication No. 2006-0276483, incorporated by reference in its entirety.

Pharmaceutically acceptable compositions include solid, semi-solid, liquid and aerosol dosage forms, such as, for example, powders, liquids, suspensions, complexations, liposomes, particulates, or the like. Preferably, the compositions are provided in unit dosage forms suitable for single administration of a precise dose.

The fluoroquinolone antimicrobial agent can be administered either alone or in some alternatives, in combination with a conventional pharmaceutical carrier, excipient or the like (e.g., mannitol, lactose, starch, magnesium stearate, sodium saccharine, talcum, cellulose, sodium crosscarmellose, glucose, gelatin, sucrose, magnesium carbonate, and the like). If desired, the pharmaceutical composition can also contain minor amounts of nontoxic auxiliary substances such as wetting agents, emulsifying agents, solubilizing agents, pH buffering agents and the like (e.g., sodium acetate, sodium citrate, cyclodextrine derivatives, sorbitan monolaurate, triethanolamine acetate, triethanolamine oleate, and the like). Generally, depending on the intended mode of administration, the pharmaceutical formulation will contain about 0.005% to 95%, preferably about 0.5% to 50% by weight of a compound of the invention. Actual methods of preparing such dosage forms are known, or will be apparent, to those skilled in this art; for example, see Remington's Pharmaceutical Sciences, Mack Publishing Company, Easton, Pa.

In one preferred embodiment, the compositions will take the form of a unit dosage form such as vial containing a liquid, solid to be suspended, dry powder, lyophilate, or other composition and thus the composition may contain, along with the active ingredient, a diluent such as lactose, sucrose, dicalcium phosphate, or the like; a lubricant such as magnesium stearate or the like; and a binder such as starch, gum acacia, polyvinylpyrrolidine, gelatin, cellulose, cellulose derivatives or the like.

Liquid pharmaceutically administrable compositions can, for example, be prepared by dissolving, dispersing, etc. an active compound as defined above and optional pharmaceutical adjuvants in a carrier (e.g., water, saline, aqueous dextrose, glycerol, glycols, ethanol or the like) to form a solution or suspension. Solutions to be aerosolized can be prepared in conventional forms, either as liquid solutions or suspensions, as emulsions, or in solid forms suitable for dissolution or suspension in liquid prior to aerosol production and inhalation. The percentage of active compound contained in such aerosol compositions is highly dependent on the specific nature thereof, as well as the activity of the compound and the needs of the subject. However, percentages of active ingredient of 0.01% to 90% in solution are employable, and will be higher if the composition is a solid, which will be subsequently diluted to the above percentages. In some embodiments, the composition will comprise 1.0%-50.0% of the active agent in solution.

Compositions described herein can be administered with a frequency of about 1, 2, 3, 4, or more times daily, 1, 2, 3, 4, 5, 6, 7 or more times weekly, 1, 2, 3, 4, 5, 6, 7, 8, 9, 10 or more times monthly. In particular embodiments, the compositions are administered twice daily.

Aerosol Delivery

For pulmonary administration, the upper airways are avoided in favor of the middle and lower airways. Pulmonary drug delivery may be accomplished by inhalation of an aerosol through the mouth and throat. Particles having a mass median aerodynamic diameter (MMAD) of greater than about 5 microns generally do not reach the lung; instead, they tend to impact the back of the throat and are swallowed and possibly orally absorbed. Particles having diameters of about 2 to about 5 microns are small enough to reach the upper- to mid-pulmonary region (conducting airways), but are too large to reach the alveoli. Smaller particles, i.e., about 0.5 to about 2 microns, are capable of reaching the alveolar region. Particles having diameters smaller than about 0.5 microns can also be deposited in the alveolar region by sedimentation, although very small particles may be exhaled.

In one embodiment, a nebulizer is selected on the basis of allowing the formation of an aerosol of a fluoroquinolone antimicrobial agent disclosed herein having an MMAD predominantly between about 2 to about 5 microns. In one embodiment, the delivered amount of fluoroquinolone antimicrobial agent provides a therapeutic effect for respiratory infections. The nebulizer can deliver an aerosol comprising a mass median aerodynamic diameter from about 2 microns to about 5 microns with a geometric standard deviation less than or equal to about 2.5 microns, a mass median aerodynamic diameter from about 2.5 microns to about 4.5 microns with a geometric standard deviation less than or equal to about 1.8 microns, and a mass median aerodynamic diameter from about 2.8 microns to about 4.3 microns with a geometric standard deviation less than or equal to about 2 microns. In some embodiments, the aerosol can be produced using a vibrating mesh nebulizer. An example of a vibrating mesh nebulizer includes the PARI E-FLOW® nebulizer or a nebulizer using PARI eFlow technology. More examples of nebulizers are provided in U.S. Pat. Nos. 4,268,460; 4,253,468; 4,046,146; 3,826,255; 4,649,911; 4,510,929; 4,624,251; 5,164,740; 5,586,550; 5,758,637; 6,644,304; 6,338,443; 5,906,202; 5,934,272; 5,960,792; 5,971,951; 6,070,575; 6,192,876; 6,230,706; 6,349,719; 6,367,470; 6,543,442; 6,584,971; 6,601,581; 4,263,907; 5,709,202; 5,823,179; 6,192,876; 6,644,304; 5,549,102; 6,083,922; 6,161,536; 6,264,922; 6,557,549; and 6,612,303 all of which are hereby incorporated by reference in their entireties. More commercial examples of nebulizers that can be used with the formulations described herein include Respirgard II®, Aeroneb®, Aeroneb® Pro, and Aeroneb® Go produced by Aerogen; AERx® and AERx Essence™ produced by Aradigm; Porta-Neb®, Freeway Freedom™, Sidestream, Ventstream and I-neb produced by Respironics, Inc.; and PARI LC-Plus®, PARI LC-Start, produced by PARI, GmbH. By further non-limiting example, U.S. Pat. No. 6,196,219, is hereby incorporated by reference in its entirety.

The amount of levofloxacin or ofloxacin that can be administered to the lungs with an aerosol dose, such as a respirable drug dose (RDD), that can include at least about 20 mg, about 30 mg, about 40 mg, about 50 mg, about 60 mg, about 70 mg, about 80 mg, about 90 mg, about 100 mg, about 110 mg, about 120 mg, about 125 mg, about 130 mg, about 140 mg, about 150 mg, about 160 mg, about 170 mg, about 180 mg, about 190 mg, about 200 mg, about 210 mg, about 220 mg, about 230 mg, about 240 mg, about 250 mg, about 260 mg, about 270 mg, about 280 mg, about 290 mg, about 300 mg, about 310 mg, about 320 mg, about 330 mg, about 340 mg, about 350 mg, about 460 mg, about 470 mg, about 480 mg, about 490 mg, about 500 mg, about 510 mg, about 520 mg, about 530 mg, about 540 mg, about 550 mg, about 560 mg, about 570 mg, about 580 mg, about 590 mg, about 600 mg, about 610 mg, about 620 mg, about 630 mg, about 640 mg, about 650 mg, about 660 mg, about 670 mg, about 680 mg, about 690 mg, about 700 mg, about 710 mg, about 720 mg, about 730 mg, about 740 mg, about 750 mg, about 760 mg, about 770 mg, about 780 mg, about 790 mg, and about 800 mg. In some embodiments, the amount of levofloxacin or ofloxacin that can be administered to the lungs with an aerosol dose, such as a respirable drug dose (RDD), that can include at least about 20 mg, 50 100 mg, 150 mg, 200 mg, 250 mg, 300 mg, 350 mg, 400 mg, 450 mg, 500 mg, 550 mg, 600 mg, 650 mg, 700 mg, 750 mg, 800 mg, 850 mg, 900 mg, 950 mg, 1000 mg, 1050 mg, 1100 mg, 1150 mg, 1200 mg, 1250 mg, 1300 mg, 1350 mg, 1400 mg, 1450 mg, and 1500 mg.

The aerosol can be administered to the lungs in less than about 10 minutes, about 5 minutes, about 4 minutes, about 3 minutes, about 2 minutes, and about 1 minute.

Indications

Methods and compositions described herein can be used to treat pulmonary infections and disorders. Examples of such disorders can include cystic fibrosis, pneumonia, and chronic obstructive pulmonary disease, including chronic bronchitis, and some asthmas. Some embodiments include treating an infection comprising one or more bacteria selected from the group consisting of *Pseudomonas aeruginosa, Pseudomonas fluorescens, Pseudomonas acidovorans, Pseudomonas alcaligenes, Pseudomonas putida, Stenotrophomonas maltophilia, Aeromonas hydrophilia, Escherichia coli, Citrobacter freundii, Salmonella typhimurium, Salmonella typhi, Salmonella paratyphi, Salmonella enteritidis, Shigella dysenteriae, Shigella flexneri, Shigella sonnei, Enterobacter cloacae, Enterobacter aerogenes, Klebsiella pneumoniae, Klebsiella oxytoca, Serratia marcescens, Morganella morganii, Proteus mirabilis, Proteus vulgaris, Providencia alcalifaciens, Providencia rettgeri, Providencia stuartii, Acinetobacter calcoaceticus, Acinetobacter haemolyticus, Yersinia enterocolitica, Yersinia pestis, Yersinia pseudotuberculosis, Yersinia intermedia, Bordetella pertussis, Bordetella parapertussis, Bordetella bronchiseptica, Haemophilus influenzae, Haemophilus parainfluenzae, Haemophilus haemolyticus, Haemophilus parahaemolyticus, Haemophilus ducreyi, Pasteurella multocida, Pasteurella haemolytica, Helicobacter pylori, Campylobacter fetus, Campylobacter jejuni, Campylobacter coli, Borrelia burgdorferi, Vibrio cholera, Vibrio parahaemolyticus, Legionella pneumophila, Listeria monocytogenes, Neisseria gonorrhoeae, Neisseria meningitidis, Burkholderia cepacia, Francisella tularensis, Kingella*, and *Moraxella*. In some embodiments, the lung infection is caused by a gram-negative anaerobic bacteria. In more embodiments, the lung infection comprises one or more of the bacteria selected from the group consisting of *Bacteroides fragilis, Bacteroides distasonis, Bacteroides* 3452A homology group, *Bacteroides vulgatus, Bacteroides ovalus, Bacteroides thetaiotaomicron, Bacteroides uniformis, Bacteroides eggerthii*, and *Bacteroides splanchnicus*. In some embodiments, the lung infection is caused by a gram-positive bacteria. In some embodiments, the lung infection comprises one or more of the bacteria selected from the group consisting of *Corynebacterium diphtheriae, Corynebacterium ulcerans, Streptococcus pneumoniae, Streptococcus agalactiae, Streptococcus pyogenes, Streptococcus milleri; Streptococcus* (Group G); *Streptococcus* (Group C/F); *Enterococcus faecalis, Enterococcus faecium, Staphylococcus aureus, Staphylococcus epidermidis, Staphylococcus saprophyticus, Staphylococcus intermedius, Staphylococcus hyicus* subsp. *hyicus, Staphylococcus haemolyticus, Staphylococcus hominis*, and *Staphylococcus saccharolyticus*. In some embodiments, the lung infection is caused by a gram-positive anaerobic bacteria. In some embodiments, the lung infection is caused by one or more bacteria selected from the group consisting of *Clostridium difficile, Clostridium perfringens, Clostridium tetini*, and *Clostridium botulinum*. In some embodiments, the lung infection is caused by an acid-fast bacteria. In some embodiments, the lung infection is caused by one or more bacteria selected from the group consisting of

*Mycobacterium tuberculosis, Mycobacterium avium, Mycobacterium intracellulare*, and *Mycobacterium leprae*. In some embodiments, the lung infection is caused by an atypical bacteria. In some embodiments, the lung infection is caused by one or more bacteria selected from the group consisting of *Chlamydia pneumoniae* and *Mycoplasma pneumoniae*.

EXAMPLES

Comparative Example 1

Administration of Fluoroquinolones in a Rat Pharmacokinetic Model

This example relates to aerosol and intravenous administration of fluoroquinolones in saline. A rat pharmacokinetic model was used to compare intravenous and pulmonary administration of fluoroquinolones. Male Sprague-Dawley rats (Charles Rivers) were administered 10 mg/kg doses of levofloxacin, ciprofloxacin, gatifloxacin, norfloxacin, or gemifloxacin. Doses were administered via the lateral tail vein, or to the lung just above the tracheal bifurcation using a micro-spray aerosol device (Penn Century, Philadelphia, Pa.). Levofloxacin was prepared in sterile 0.9% saline to concentrations of 5 mg/ml (IV) and 60 mg/ml (aerosol).

Approximately 0.3 ml blood samples were taken from 2-6 rats at each timepoint via an indwelling jugular vein cannula, and collected in lithium heparin tubes. Bronchial alveolar lavage (BAL) and lung tissue were collected following euthanasia. Levofloxacin concentrations in plasma, lung tissue and BAL were determined using a HPLC assay, and the data analyzed using WinNonlin (Pharsight Corporation, v 5.0). Sample concentrations were determined against a standard curve.

Serum $AUC_{(0\text{-}inf)}$ (area under the concentration time curve, for time zero to infinity), serum MRT (mean retention time), serum $t\frac{1}{2}$ (half-life), BAL AUC, MAT (mean absorption time), and F (bioavailability) were determined and are shown in Table 1.

TABLE 1

| Drug | Route | Serum AUC (0-inf) | Serum MRT | Serum t½ | BAL AUC | MAT (h) | F, % from Lung vs IV |
|---|---|---|---|---|---|---|---|
| Levofloxacin | IV | 3.8 | 0.7 | 0.5 | 1.6 | NA | NA |
| Levofloxacin | Aerosol | 3.7 | 0.7 | 0.5 | 3.0 | 0 | 97% |
| Ciprofloxacin | IV | 2.6 | 0.76 | 0.53 | 3.9 | NA | NA |
| Ciprofloxacin | Aerosol | 0.8 | 1.35 | 0.93 | 78.4 | 0.59 | 82% |
| Gatifloxacin | IV | 5.31 | 1.39 | 1.06 | 0.35 | NA | NA |
| Gatifloxacin | Aerosol | 5.83 | 1.34 | 1.13 | 3.12 | 0 | 100% |
| Norfloxacin | IV | 4.65 | 1.59 | 1.21 | 0.8 | NA | NA |
| Norfloxacin | Aerosol | 4.46 | 1.29 | 1.13 | 24.6 | 0 | 100% |
| Gemifloxacin | IV | 4.54 | 1.41 | 1.04 | 0.9 | NA | NA |
| Gemifloxacin | Aerosol | 5.86 | 2.06 | 1.68 | 140.4 | 0.65 | 86% |

Aerosol administration of ciprofloxacin, gatifloxacin, norfloxacin, or gemifloxacin resulted in a significant increase in BAL AUC, compared to intravenous administration. Aerosol administration of levofloxacin did not show such a significant increase in BAL AUC, compared to intravenous administration. In addition, levofloxacin showed rapid absorption from the lung into serum. Thus, aerosol administration of levofloxacin in saline did not result in significant increased availability of drug to the lung.

Comparative Example 2

Aerosol Administration of Levofloxacin with Divalent Cations in Rats

This example relates to a series of studies that included aerosol administration of levofloxacin with divalent cations and lactose and IV or aerosol administration of levofloxacin in saline. Rats were administered 10 mg/kg levofloxacin (LVX) in saline or LVX formulated with $CaCl_2$, $MgCl_2$, or $Zn^{+2}$. Table 2 shows the formulations of levofloxacin used in these studies.

TABLE 2

|  | Levofloxacin (IV) | Levofloxacin (Aerosol) | Levofloxacin ($MgCl_2$) | Levofloxacin ($CaCl_2$) | Levofloxacin ($ZnCl_2$) |
|---|---|---|---|---|---|
| Levofloxacin | 5 mg/ml | 60 mg/ml | 60 mg/ml | 60 mg/ml | 60 mg/ml |
| $MgCl_2$ | — | — | 120 mM | — | — |
| $CaCl_2$ | — | — | — | 120 mM | — |
| $ZnCl_2$ | — | — | — | — | 120 mM |
| Lactose | — | — | 150 mM | — | — |

Figure 1:
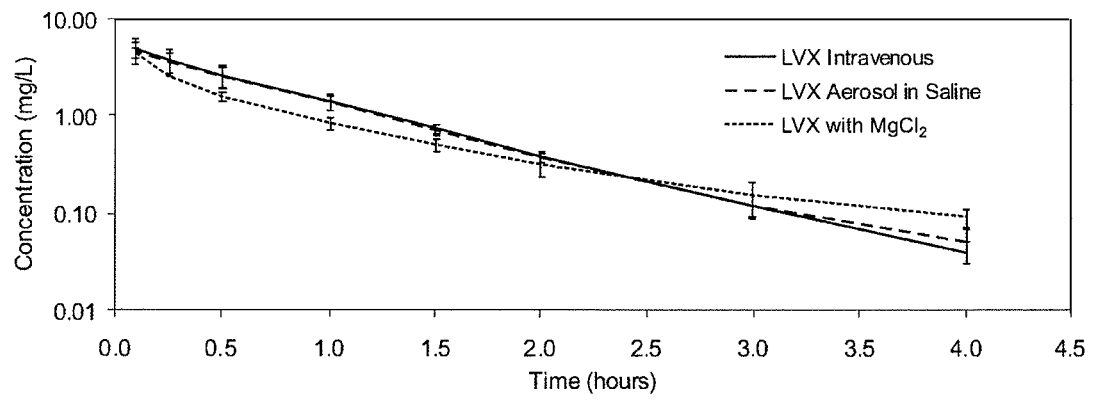

In one study, pharmacokinetic parameters including $C_{max}$ (maximum serum concentration), CL/F (total body clearance/bioavailability) were measured and are shown in Table 3. A graph of plasma concentration of levofloxacin with time is shown in FIG. 1, where levofloxacin was administered by aerosol, by intravenous injection, or by aerosol with $MgCl_2$.

TABLE 3

| Parameter | Unit | Mean (+/−SD) | | |
|---|---|---|---|---|
|  |  | LVX IV | LVX Aerosol | LVX $MgCl_2$ |
| Plasma AUC | hr · mg/L | 3.79 (±0.89) | 3.69 (±0.14) | 3.72 (±0.24) |
| Plasma Half-life | hr | 0.49 (±0.10) | 0.52 (±0.09) | 0.73 (±0.07) |
| Plasma $C_{max}$ | mg/L | 5.54 (±1.51) | 6.01 (±1.54) | 6.66 (±1.70) |
| Plasma CL/F | L/hr/kg | 2.81 (±0.54) | 2.83 (±0.11) | 2.68 (±0.17) |
| Plasma MRT | hr | 0.70 (±0.14) | 0.71 (±0.08) | 0.88 (±0.06) |
| Plasma MAT | hr | NA | 0.01 | 0.18 |
| Plasma F (Bioavailability) | % | NA | 97.4 | 98.2 |
| BAL $AUC_{(0-6\,h)}$ | hr · mg/L | 1.6 | 3.0 | 8.3 |

A two compartment pharmacokinetic model may be used describe the difference in graphs of plasma levofloxacin with time for intravenous and aerosol administration. Plasma AUC after intravenous administration was similar to plasma AUC after administration by aerosol with $Mg^{+2}$ (3.79 hr·mg/L vs. 3.72 hr·mg/L, respectively). This suggests near 100% bioavailability of the divalent-complex antibiotic from the lung.

The mean residence time (MRT) of levofloxacin was greater after aerosol administration compared to after intravenous administration (0.88 vs. 0.70 hours). This delay in absorption was associated with an increase in BAL levofloxacin $AUC_{(0-6h)}$ in BAL (1.6 hr·mg/L vs. 8.3 hr·mg/L for intravenous vs. aerosol dosing, respectively), and an 18-fold increase in the mean absorption time (MAT)

In another study, levofloxacin levels after aerosol administration for formulations containing saline, $Zn^{2+}$, $Ca^{+2}$ or $Mg^{+2}$ were measured and pharmacokinetic parameters were determined. Table 4 and FIG. 2 summarize the results.

TABLE 4

| Drug | Route | Serum AUC (0-inf) | Serum MRT | Serum t½ | BAL AUC | MAT (h) | F, % from Lung vs IV |
|---|---|---|---|---|---|---|---|
| Levofloxacin | IV | 3.8 | 0.7 | 0.5 | 1.6 | NA | NA |
| Levofloxacin | Aerosol | 3.7 | 0.7 | 0.5 | 3.0 | 0 | 97% |
| Levofloxacin ($MgCl_2$) | Aerosol | 4.4 | 1.35 | 1.2 | 29.6 | 0.7 | 116% |
| Levofloxacin ($CaCl_2$) | Aerosol | 4.3 | 1.17 | 0.8 | 8.3 | 0.5 | 116% |
| Levofloxacin ($ZnCl_2$) | Aerosol | 4.4 | 1.6 | 1.8 | 55.6 | 0.9 | 100% |

Aerosol administration of levofloxacin complexed with $Ca^{+2}$ and $Mg^{+2}$ resulted in a longer plasma half-life and longer MAT compared to levofloxacin formulated in saline, indicative of slower lung clearance to plasma (Table 4). Levofloxacin formulated with $Ca^{+2}$ or $Mg^{+2}$ produced a 2- to 5-fold higher levofloxacin $C_{max}$ and AUC in BAL and lung tissue compared to intravenous levofloxacin or aerosolized levofloxacin formulated in saline (Table 4, FIG. 2). These data suggest that aerosol levofloxacin complexed with divalent cation should result in higher efficacy in the treatment of pulmonary infections.

Example 3

Pharmacokinetic Modeling and Deconvolution Analysis

This example relates to modeling drug concentrations in lung. Pharmacokinetic deconvolution methods are useful to determine the amount of drug remaining in the lung after administration. Such methods are particularly useful where direct measurements are difficult and/or produce variable results, for example, measuring drug concentrations in lung using sputum samples.

Serum and urinary pharmacokinetic parameters can be determined using non-compartmental and compartmental methods, and drug concentrations in the lung over time can be calculated using deconvolution. This approach has been reported for aerosol delivery of tobramycin, where a dose of 5.6 mg/kg showed bioavailability of about 9% and absorption over a 3 hour period, consistent with empirically derived data (Cooney G. F., et al, "Absolute bioavailability and absorption characteristics of aerosolized tobramycin in adults with cystic fibrosis." J. Clinical Pharmacol. (1994), 34, 255-259, incorporated herein by reference in its entirety).

An example deconvolution method is summarized in FIG. 3. This analysis compares the appearance and elimination of drug following aerosol and intravenous doses to determine the amount of drug remaining in the lung (absorption compartment) over time. To estimate concentrations of drug in lung, amounts were divided by estimates of the epithelial lung fluid (ELF) volume (25 ml) for each subject. Non-compartmental pharmacokinetic analysis was subsequently applied to these projected concentrations of drug in the lung to determine AUCs.

Figure 4:
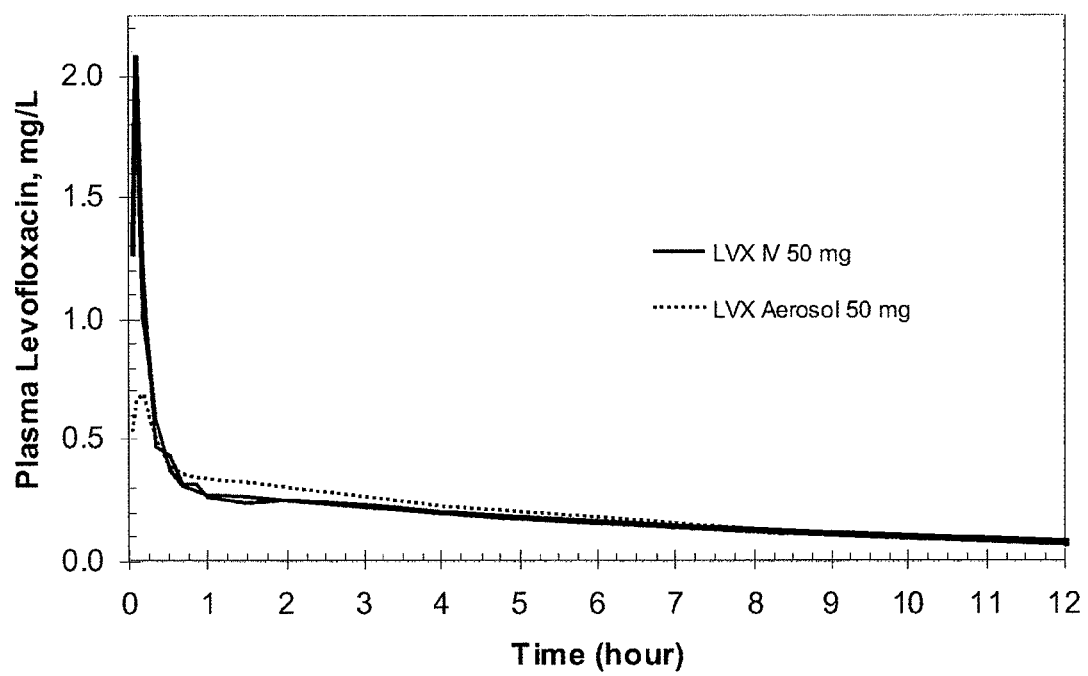
FIG. 4 shows a graph of plasma levofloxacin (LVX) concentrations after administration of 50 mg LVX in saline by aerosol or intravenous routes.

Application of the deconvolution methodology can be accomplished by human or animal aerosol dosing of 50 mg respirable drug dose of levofloxacin in saline or complexed with $Mg^{+2}$, delivered in a nebulizer or other respiratory delivery device, with resulting plasma drug concentrations profiles and calculated pharmacokinetic parameters as illustrated in FIG. 4 and Tables 5 and 6. Serum levofloxacin concentrations following a 5 minute IV infusion of levofloxacin to a single healthy volunteer were analyzed using WinNonlin and the pharmacokinetic parameters presented in Table 5. On a separate occasion, this volunteer received a single aerosol dose of levofloxacin (RDD=50 mg) by a PARI eFlow vibrating mesh nebulizer. FIG. 4 shows a comparison of the serum levofloxacin concentrations following an IV or aerosol dose. Using the PK model depicted in FIG. 3, serum concentrations of levofloxacin measured in serum following an aerosol dose were deconvoluted using the serum PK data for an IV dose of levofloxacin (PK parameters shown in Table 5). The results are shown in Table 6, which show the estimated amount of levofloxacin (in mg) remaining in the lung over time.

TABLE 5

| Parameter | Unit | Estimate |
|---|---|---|
| AUC | hr · mg/L | 3.14 |
| K10_HL | hr | 0.92 |
| Alpha | 1/hr | 6.85 |
| Beta | 1/hr | 0.11 |
| Alpha_HL | hr | 0.10 |
| Beta_HL | hr | 6.50 |
| A | mg/L | 2.05 |
| B | mg/L | 0.30 |
| $C_{max}$ | mg/L | 1.88 |
| CL | L/hr | 15.93 |
| AUMC | hr · hr · mg/L | 26.78 |
| MRT | hr | 8.49 |
| Vss | L | 135.29 |
| V2 | L | 114.03 |
| CLD2 | L/hr | 111.26 |

TABLE 6

| Hours | Input rate (mg/hr) | Cumulative input into serum compartment (mg) | Input fraction | Drug remaining in lung (mg) | Fraction remaining |
|---|---|---|---|---|---|
| 0.24 | 35.79 | 26.67 | 0.53 | 23.33 | 0.47 |
| 0.48 | 13.80 | 31.16 | 0.62 | 18.84 | 0.38 |
| 0.72 | 18.25 | 34.84 | 0.70 | 15.16 | 0.30 |
| 0.96 | 20.55 | 39.88 | 0.80 | 10.12 | 0.20 |
| 1.2 | 14.98 | 44.14 | 0.88 | 5.86 | 0.12 |
| 1.44 | 9.21 | 47.03 | 0.94 | 2.97 | 0.06 |
| 1.68 | 5.13 | 48.68 | 0.97 | 1.32 | 0.03 |
| 1.92 | 1.81 | 49.51 | 0.99 | 0.49 | 0.01 |
| 2.16 | 0.45 | 49.69 | 0.99 | 0.31 | 0.01 |
| 2.4 | 0.36 | 49.79 | 1.00 | 0.21 | 0.00 |
| 2.64 | 0.27 | 49.86 | 1.00 | 0.14 | 0.00 |
| 2.88 | 0.18 | 49.92 | 1.00 | 0.08 | 0.00 |
| 3.12 | 0.11 | 49.95 | 1.00 | 0.05 | 0.00 |
| 3.36 | 0.08 | 49.97 | 1.00 | 0.03 | 0.00 |
| 3.6 | 0.05 | 49.99 | 1.00 | 0.01 | 0.00 |
| 3.84 | 0.02 | 50.00 | 1.00 | 0.00 | 0.00 |

Figure 5:
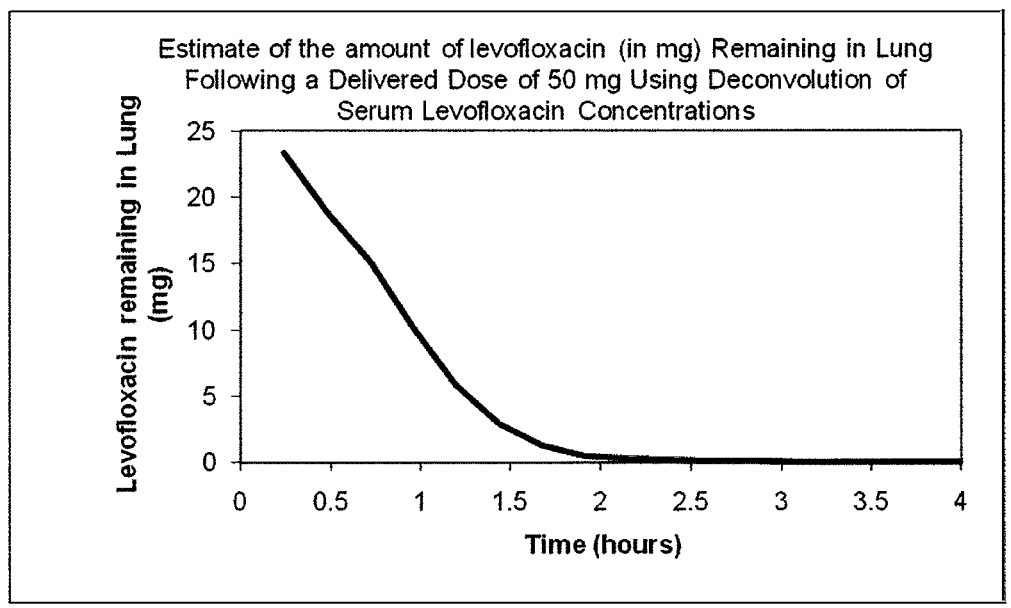
FIG. 5 shows a graph of the estimated amount of drug remaining in the lung compartment following aerosol administration of 50 mg respirable drug dose levofloxacin in saline, where amount of drug remaining is estimated using deconvolution of serum data.

These data can be used to calculate the amount (in mg) of levofloxacin remaining in the lung as a function of time. FIG. 5 and Table 6 shows an example for the estimated amount of drug remaining in the lung over time, whereas only 10% of the 50 mg respirable drug dose administered over a 5 minute period remains in the lung after 1.2 hours. This experiment demonstrates the utility of the deconvolution method.

Comparative Example 4

Aerosol and Systemic Administration of Levofloxacin with Saline

This example relates to aerosol and systemic administration of levofloxacin formulated in a saline solution using estimated respirable drug doses of 20 mg or 40 mg (nebulizer loaded doses of 43.3 and 86.6 mg, respectively) of levofloxacin. Single aerosol doses of two dose levels levofloxacin (using the IV formulation Levaquin®) were administered to normal healthy volunteers and stable CF subjects using the PARI eFlow high efficiency nebulizer.

Safety, tolerability, and pharmacokinetics (serum, sputum, and urinary excretion) data were collected after each dose. The nebulizer was loaded with 3.6 ml of a Levaquin® solution diluted in saline to isotonicity, at a concentration of 11.9 mg/ml for the 20 mg respirable drug dose group, and at a concentration of 23.8 mg/ml for the 40 mg respirable drug dose group. These volumes correspond to "load" doses of 43.3 mg and 86.6 mg levofloxacin for the 20 and 40 mg RDD, respectively. Table 7 summarizes nebulizer loaded doses with the corresponding estimated RDD for levofloxacin formulated in saline.

TABLE 7

| Levofloxacin Concentration in Saline (mg/L) | Nebulizer Loaded dose (mg) | RDD (based on particles <5 μm) (mg) |
|---|---|---|
| 12 | 43.3 | 20 |
| 23.8 | 86.6 | 40 |

Novaluzid® (AstraZeneca) was co-administered to minimize the oral absorption of any levofloxacin that was swallowed during inhalation. Each subject received an intravenous dose of levofloxacin and an aerosol saline dose at the first visit to generate pharmacokinetic data for comparison with aerosol levofloxacin doses, and to assess the tolerability of delivering solutions using the eFlow device.

Serum and urine levofloxacin concentrations were analyzed using a validated HPLC assay by Anapharm (Quebec City, Canada). Sputum levofloxacin assays were developed and cross validated using the serum assay.

Serum data: Serum levofloxacin concentrations following the intravenous infusion were fit to a two-compartment open pharmacokinetic model using iteratively reweighted least-squares regression (WinNonlin). A weight of 1/y-observed was applied in the regression. Goodness of fit was assessed by the minimized objective function and inspection of weighted residual plots. Serum levofloxacin concentrations resulting from aerosol administration were analyzed using deconvolution methods to estimate the residence time of the aerosol dose in the lung (Gibaldi M. and Perrier D. Pharmacokinetics, 2nd Edition. Marcel Dekker: New York, 1982, incorporated herein by reference in its entirety). The pharmacokinetic model and approach used for deconvolution analysis is described in Example 3. Briefly, this analysis compares the appearance and elimination of drug following aerosol and intravenous doses to determine the amount of drug remaining in the lung (absorption compartment) over time. To estimate concentrations of drug in lung, amounts were divided by estimates of the epithelial lung fluid (ELF) volume (25 ml) for each subject. Noncompartmental pharmacokinetic analysis was subsequently applied to these projected concentrations of drug in the lung to determine values for AUC.

Sputum data: Sputum concentration data were analyzed using noncompartmental pharmacokinetic methods (Gibaldi M. and Perrier D. Pharmacokinetics, $2^{nd}$ Edition. Marcel Dekker: New York, 1982, incorporated herein by reference in its entirety). The area under the sputum concentration vs. time curve was estimated using the linear trapezoidal rule. Since sputum was only collected from 0.5 to 8 hrs, forward and backward extrapolation from terminal and initial phases was conducted to generate estimates of secondary pharmacokinetic parameters ($C_{max}$, AUC).

PK-PD parameters such as AUC:MIC, and $C_{max}$:MIC, were generated for lung exposures estimated from deconvolution of serum levofloxacin concentration data. Examples of parameters were calculated at different values for levofloxacin MIC for *P. aeruginosa* at estimated respirable doses of levofloxacin ranging from 20-120 mg administered twice daily in CF subjects. Levofloxacin MIC distributions ($MIC_{50}$, $MIC_{90}$, and mode MIC) were measured for clinical isolates from CF isolates (Traczewski M M and Brown S D. In Vitro activity of doripenem against *P. aeruginosa* and *Burkholderia cepacia* isolates from both cystic fibrosis and non-cystic fibrosis patients. Antimicrob Agents Chemother 2006; 50:819-21, incorporated herein by reference in its entirety).

Dosing summary: A total of 7 normal healthy volunteers (NHV) and 9 subjects with CF were enrolled in the study. All subjects completed all phases of the protocol; the dose summary is provided in Table 8. Seven of 9 cystic fibrosis subjects received both the and 40 mg respirable drug dose levels, whereas 2 subjects were re-dosed with the 20 mg dose level with salbutamol pretreatment. Forced expiratory volume during 1 second ($FEV_1$)

TABLE 8

| Subject | Gender | Baseline $FEV_1$ (% Pred) | Levofloxacin Doses Studied | | |
|---|---|---|---|---|---|
| | | | 20 mg | 40 mg | 20 mg A* |
| Normal healthy volunteers | | | | | |
| 001 | M | 83% | X | X | |
| 002 | M | 100% | X | X | |
| 003 | M | 109% | X | X | |
| 004 | M | 130% | X | X | |
| 006 | M | 119% | X | X | |
| 008 | M | 82% | X | X | |
| 009 | F | 104% | X | X | |
| Cystic fibrosis patients | | | | | |
| 010 | F | 58% | X | X | |
| 012 | M | 67% | X | | X |
| 013 | F | 40% | X | X | |
| 014 | F | 40% | X | X | |
| 015 | M | 74% | X | X | |
| 016 | F | 66% | X | X | |

TABLE 8-continued

| Subject | Gender | Baseline FEV$_1$ (% Pred) | Levofloxacin Doses Studied | | |
|---|---|---|---|---|---|
| | | | 20 mg | 40 mg | 20 mg A* |
| 018 | M | 63% | X | X | |
| 019 | M | 42% | X | X | |
| 022 | M | 48% | X | | X |

*A = Repeat study using pretreatment with salbutamol

Figure 6:
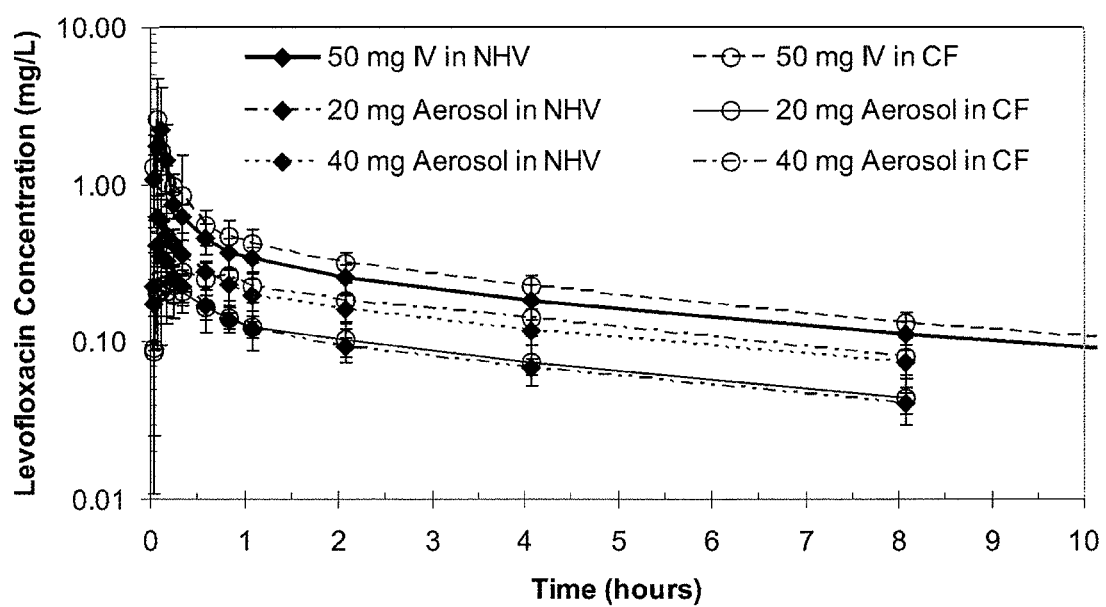
FIG. 6 shows a graph of serum levofloxacin concentrations in normal healthy volunteers and cystic fibrosis patients after a single intravenous or aerosol dose of levofloxacin administered in saline. Doses are shown as estimated RDD; the 20 mg and 40 mg RDDs represent nebulizer loaded doses of 43.3 and 86.6 mg, respectively.

Levofloxacin pharmacokinetics in serum: FIG. 6 shows mean serum levofloxacin concentrations in normal and CF subjects following IV and aerosol doses. Total levofloxacin clearance was 17.2 and 14.1 L/h in the NHV and CF subjects, respectively. Serum levofloxacin concentrations following aerosol administration generally paralleled those observed with the intravenous dose, particularly after 1 hour post-dosing. Comparison of the levofloxacin AUCs from IV or aerosol dosing using model-independent analysis showed that levofloxacin exposure from aerosol doses relative to the 50 mg IV dose was (mean+/−SD) 35.6+/−9.4% and 59.4+/−16.6% for the low and high aerosol doses, respectively for the normal volunteers, and 27.9+/−3.3% and 51.1+/−11.2% for CF subjects.

Figure 7:
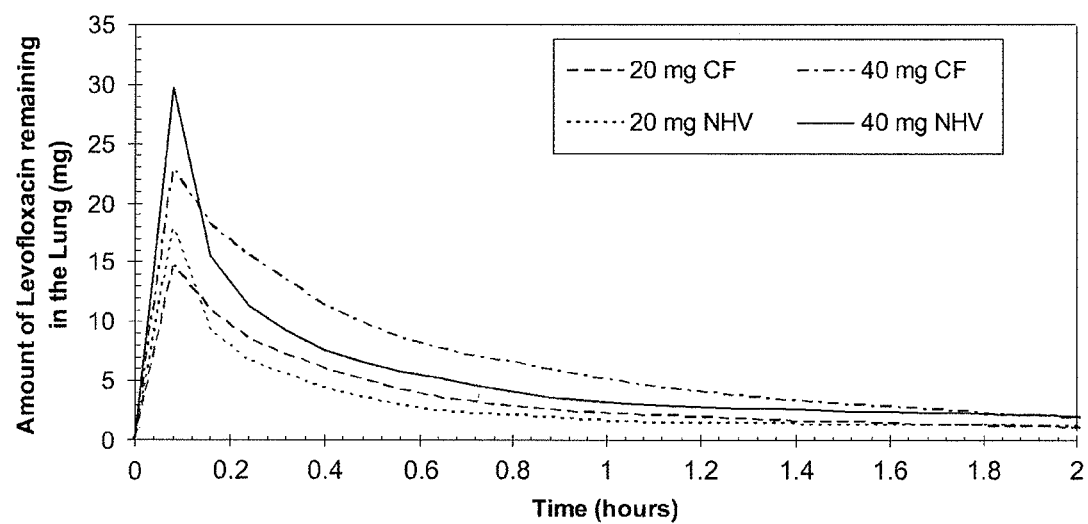
FIG. 7 shows a graph of deconvolution estimates of the average amount of levofloxacin remaining in the lung in 7 healthy volunteers and 9 CF patients following a single aerosol dose of 43.3 mg loaded into nebulizer (estimated respirable delivered dose (RDD) of 20 mg, and a 86.6 mg dose loaded into the nebulizer (estimated RDD of 40 mg) formulated in normal saline.
Figure 8A:
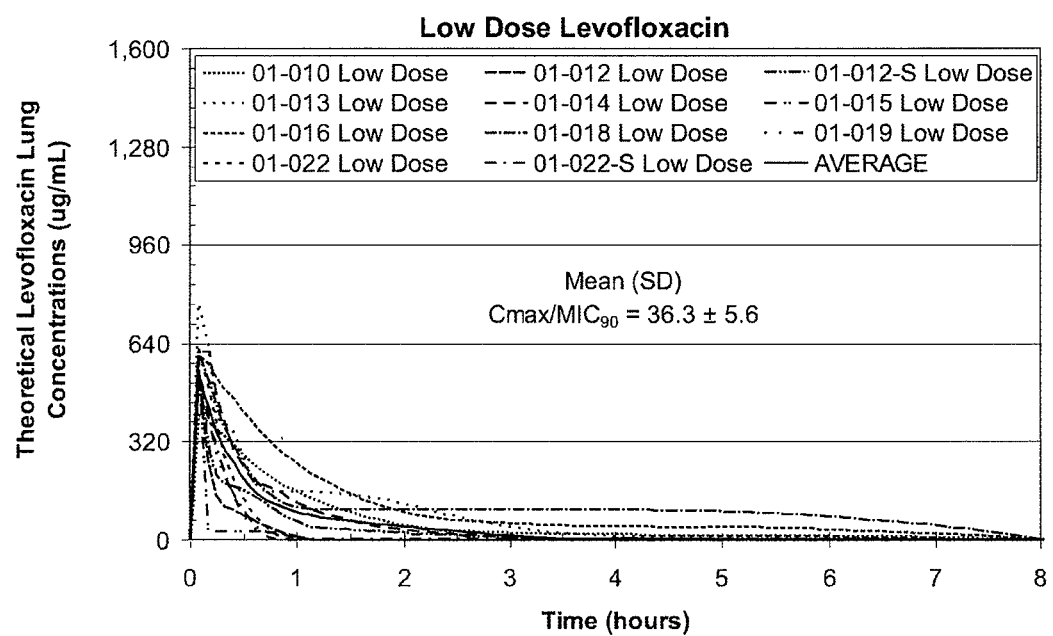
FIG. 8A shows a graph of the estimated levofloxacin concentrations in lung epithelial lining fluid following a single 20 mg respirable drug dose (43.3 mg of levofloxacin loaded into the nebulizer) formulated in normal saline in CF patients.
Figure 8B:
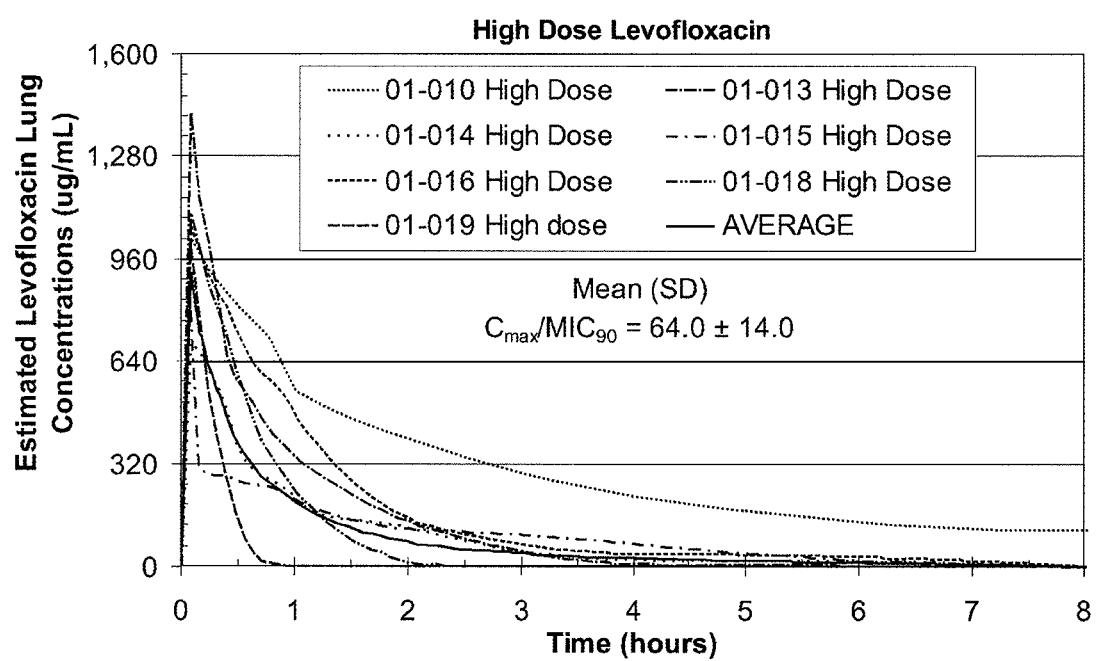
FIG. 8B shows a graph of the estimated levofloxacin concentrations in lung epithelial lining fluid following a single 40 mg respirable drug dose (86.6 mg loaded into the nebulizer) formulated in normal saline in CF patients.

Serum deconvolution analysis: Serum levofloxacin concentrations following aerosol administration were successfully deconvoluted in all subjects, permitting estimation of the amount of drug in the absorption (lung) compartment over time (FIG. 7). Absorption from the lung into serum occurred significantly more slowly in CF subjects than in healthy normal volunteers; 50% of the lung dose appeared to remain in the lung for at least 0.5 hours after the dose. Using a literature value for estimation of lung epithelial lining fluid (ELF) volume of 25 ml, the estimated concentrations of levofloxacin in ELF of CF patients following a single aerosol dose is shown in FIGS. 8A and 8B (Rennard, S, G. et al., Estimation of volume of epithelial lining fluid recovered by lavage using urea as a marker of dilution. J. Appl. Physio. 60: 532-8, incorporated by reference herein in its entirety). Mean projected $C_{max}$ concentrations in the ELF of CF patients at the conclusion of the low and high doses exceeded 500 μg/ml and 1000 μg/ml, respectively. When integrated over time, the projected mean+/−SD levofloxacin AUC in lung fluid was 365+/−338 and 710+/−471 for the low and high dose in healthy subjects, and 354+/−274 and 1,199+/−1,147 for low and high doses in CF patients.

Figure 9:
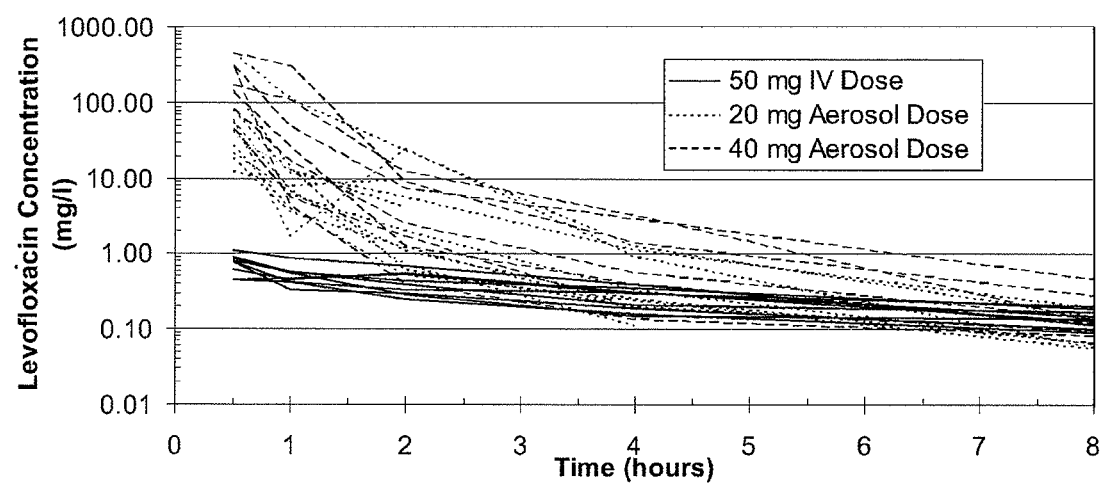
FIG. 9 shows a graph of sputum levofloxacin concentrations in CF subjects following a single IV infusion or aerosol dose of levofloxacin formulated in normal saline. Doses are shown as estimated RDD; the 20 mg and 40 mg RDDs represent nebulizer loaded doses of 43.3 and 86.6 mg, respectively.

Levofloxacin pharmacokinetics in sputum: FIG. 9 shows levofloxacin concentrations in sputum following administration of the low and high aerosol dose in CF subjects. Sputum levofloxacin concentrations following both aerosol dose levels were markedly higher for at least 1 hour post-dose with aerosol levofloxacin than those obtained with the 50 mg IV dose. Concentrations tended to fall rapidly during the first 2 hours of administration, consistent with drug absorption from the lung. Sputum levofloxacin concentrations were variable within and between patients, but generally the 86.6 mg loaded dose did provide higher concentrations over the period of observations.

Figure 10:
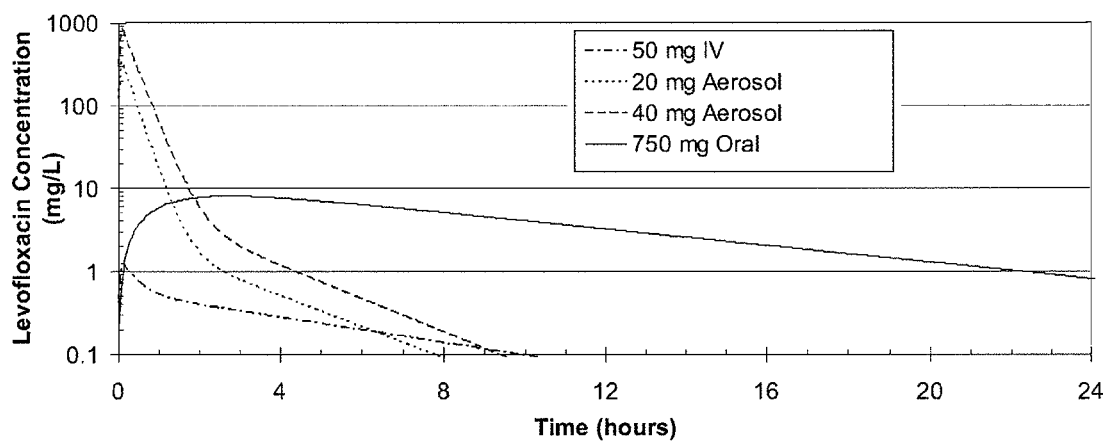
FIG. 10 shows a graph depicting modeled sputum levofloxacin concentrations in CF subjects following various doses and routes of administration (aerosol doses formulated in normal saline) of levofloxacin.

Levofloxacin concentrations in sputum from CF subjects following aerosol administration were averaged and compared with concentrations obtained by other routes of administration. FIG. 10 depicts modeled sputum concentrations in CF subjects for both aerosol dose levels, the 50 mg IV dose to the same subjects infused over 5 minutes, and a 750 mg oral dose (another study not described herein); Table 9 shows $C_{max}$, AUC, and half-life values for measured sputum levofloxacin concentrations.

TABLE 9

| Parameter | 50 mg IV | 20 mg Aerosol | 40 mg Aerosol | 750 mg Oral |
|---|---|---|---|---|
| $C_{max}$ (mg/L) | 0.8 | 86.2 | 211.5 | 8.7 |
| AUC (hr · mg/L) | 2.5 | 67.1 | 171.4 | 93.4 |
| $T_{1/2}$ (h) | 3.8 | 0.9 | 1.3 | 6.7 |

While a 750 mg oral levofloxacin dose results in more prolonged drug concentrations in sputum, aerosol doses as low as 20 mg produce peak concentrations 10-fold higher.

FIG. 6 shows serum levofloxacin concentrations following single RDDs of 20 or 40 mg of levofloxacin formulated in saline, and IV doses of Levaquin to normal healthy volunteers and CF patients. These data were used to perform pharmacokinetic deconvolution as previously described. FIG. 7 shows the results of deconvolution, showing the estimated amount of levofloxacin remaining in the lung over time. Levofloxacin remained in the lung for a longer period in CF patients compared to normal healthy volunteers (FIG. 7). Notably, the levofloxacin concentrations observed in sputum are consistent with ELF concentrations projected from the deconvolution analysis (FIGS. 8A and 8B vs. FIG. 9 and Table 9).

PK-PD analysis: Integration of pharmacokinetics with susceptibility data for *P. aeruginosa* allows for assessment of the expected pharmacodynamic effects in vivo. PK-PD parameters for fluoroquinolones include the 24 hr AUC:MIC and $C_{max}$:MIC ratios. Very high $C_{max}$:MIC ratios appear to be significant for rapid bacterial killing and suppression of drug resistance.

The results of PK-PD analysis with simulated ELF PK data (generated from the amount of levofloxacin in lung divided by the ELF volume) from the deconvolution analysis for twice daily dosing of levofloxacin along with MIC data for *P. aeruginosa* can be used to calculate levofloxacin PK-PD indices for *P. aeruginosa*. Table 10 shows predicted PK-PD indices ($C_{max}$:MIC; 24 h AUC:MIC) for particular dosage regimens of levofloxacin.

TABLE 10

| Levofloxacin MIC* (mg/L) | $C_{max}$:MIC (24 h AUC:MIC) values for Levofloxacin dosage regimens | | | |
|---|---|---|---|---|
| | 20 mg BID | 40 mg BID | 80 mg BID | 120 mg BID |
| 32 | 16 (22) | 31 (44) | 62 (88) | 94 (131) |
| 16 (MIC$_{90}$) | 31 (44) | 62 (88) | 124 (175) | 188 (263) |

TABLE 10-continued

| Levofloxacin MIC* | $C_{max}$:MIC (24 h AUC:MIC) values for Levofloxacin dosage regimens | | | |
|---|---|---|---|---|
| (mg/L) | 20 mg BID | 40 mg BID | 80 mg BID | 120 mg BID |
| 8 | 62 (88) | 124 (175) | 248 (350) | 375 (525) |
| 4 | 124 (175) | 248 (350) | 496 (700) | 750 (1,050) |
| 2 | 248 (350) | 496 (700) | 992 (1,400) | 1,500 (2,100) |
| 1 ($MIC_{50}$) | 496 (700) | 992 (1,400) | 1,884 (2,800) | 3,000 (4,200) |
| 0.5 (mode) | 992 (1,400) | 1,884 (2,800) | 3,768 (4,200) | 6,000 (8,400) |
| 24 h AUC (h · mg/L) | 700 | 1,400 | 2,800 | 4,200 |
| $C_{max}$ (mg/L) | 500 | 1,000 | 2,000 | 3,000 |

*, $MIC_{50}$, $MIC_{90}$, and mode values from Traczewski M M and Brown S D (2006)

For example, a daily dose of 20 mg BID levofloxacin, $C_{max}$:MIC=248; 24 h AUC:MIC=350; and a levofloxacin MIC=2 mg/L. The simulations show that the primary target value of $C_{max}$:MIC>20 would be obtained by all regimens for over 90% of CF isolates of P. aeruginosa. In addition, the secondary PK-PD target value of 24 hr AUC:MIC>300 would be obtained for a majority of strains at the lower doses, but could also cover over 90% of the isolates at the higher doses projected to be evaluated in upcoming clinical studies.

Comparative Example 5

Aerosol Administration of 30 mg/ml and 50 mg/ml Solutions of Levofloxacin Formulated with $MgCl_2$ This example relates to aerosol administration to CF patients of 30 mg/ml and 50 mg/ml solutions of levofloxacin formulated with $MgCl_2$. Table 11 shows the formulations of levofloxacin with $MgCl_2$ and lactose.

TABLE 11

| | 30 mg/ml | 50 mg/ml |
|---|---|---|
| Levofloxacin, mg/ml (mM) | 30 (81.6) | 50 (136) |
| Magnesium, mg/ml (mM) | 1.5 (60) | 2.4 (100) |
| Chloride, mg/ml (mM) | 4.3 (120) | 7.1 (200) |
| Lactose, mg/ml (mM) | 51.4 (150) | 51.4 (150) |
| pH | 6.3 | 6.3 |
| Osmolality, mOsm/kg | 314 | 400 |

Eight stable CF patients received loaded doses of 78 mg, 175 mg, and 260 mg (corresponding to RDD of 40 mg, 80 mg, and 120 mg, respectively) of levofloxacin formulated with $MgCl_2$ using an eFlow high efficiency nebulizer (PARI Pharma, Munich, Germany). Escalated doses were administered 1 week apart. A separate group of 7 CF patients were administered a single dose of 750 mg oral levofloxacin at weekly intervals for 4 consecutive weeks. Serum and sputum samples were assayed for levofloxacin by HPLC. Serum and sputum levofloxacin concentration data were analyzed using non-compartmental pharmacokinetic methods. Mean pharmacokinetic parameters are shown in Table 12.

TABLE 12

| | | Dose | | | | |
|---|---|---|---|---|---|---|
| | Parameter | Aerosol 78 mg RDD: 40 mg | Aerosol 175 mg RDD: 80 mg | Aerosol 260 mg RDD: 120 mg | Oral 750 mg | IV 50 mg |
| Sputum | $C_{max}$ (mg/L) | 388 | 714 | 1112 | 8.7 | 1.05 |
| | $C_{max}$:$MIC_{90}$* | 49 | 89 | 139 | 1.1 | 0.1 |
| | $AUC_{(0-inf)}$ (h · mg/L) | 851 | 656 | 1448 | 93.4 | 5.70 |
| | t½ (h) | 3.09 | 1.61 | 2.51 | 6.70 | 3.5 |
| Serum | $C_{max}$ (mg/L) | 0.48 | 0.95 | 1.30 | 7.30 | 2.55 |
| | $AUC_{(0-inf)}$ (h · mg/L) | 2.08 | 4.45 | 6.54 | 76.6 | 3.91 |
| | t½ (h) | 5.69 | 6.50 | 6.20 | 7.60 | 5.89 |
| | MAT** | 1.06 | 1.61 | 1.30 | ND | ND |

*P. aeruginosa $MIC_{90}$ for CF isolates is 8 µg/ml
MAT = Mean absorption time form the lung.

PK-PD data have previously shown that for fluoroquinolones, $C_{max}$:MIC ratio is a PK-PD parameter associated with optimal bacterial killing and prevention of resistance. Aerosol administration of levofloxacin with $MgCl_2$ provides concentrations in sputum that achieve $C_{max}$:MIC ratios for P. aeruginosa >40. In contrast, an oral levofloxacin dose of 750 mg produces a ratio of 1.1. These data show that aerosolized doses of levofloxacin with $MgCl_2$ provide high exposures in sputum that are greater than those achievable with oral levofloxacin.

Comparative Example 6

Figure 11:
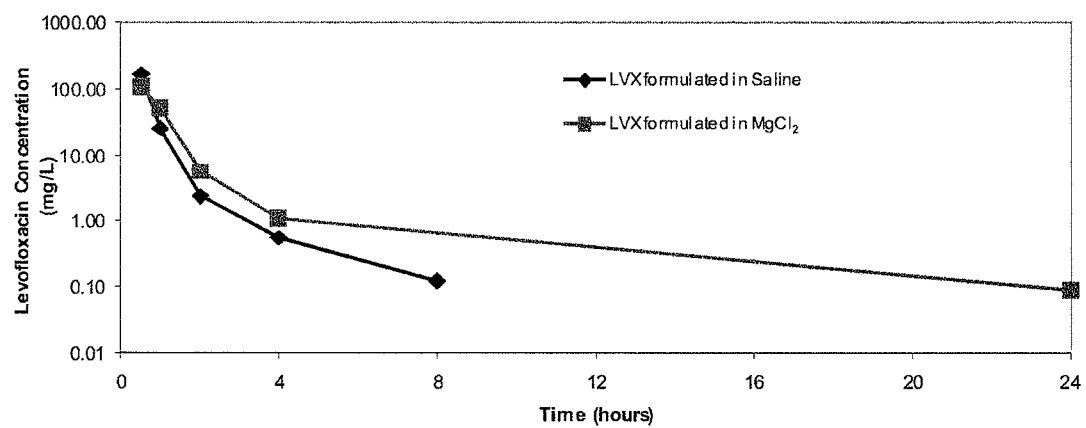
FIG. 11 shows a graph of sputum levofloxacin (LVX) concentration in cystic fibrosis patients, after aerosol administration of 50 mg/ml LVX formulated with $MgCl_2$ or with saline using an estimated 40 mg respirable drug dose (RDD) which corresponds to a 86.6 mg loaded drug dose.

Comparison of Aerosol Administration of a 40 mg RDD of Levofloxacin Formulated in Saline or MgCl$_2$, in CF Patients This example relates to aerosol administration of levofloxacin with MgCl$_2$ or in saline using estimated respirable drug doses (RDD) of 40 mg levofloxacin. The concentrations of levofloxacin in saline are 23.8 mg/ml and 30 mg/ml in a formulation containing MgCl$_2$/lactose (see Table 11). CF patients received 40 mg respirable drug doses of levofloxacin by aerosol delivery: 7 patients received levofloxacin formulated in saline; 10 patients received the same estimated RDD received levofloxacin formulated with MgCl$_2$. Sputum samples were taken at various times up to 24 hours and levofloxacin concentrations determined using a HPLC/fluorescence method. Mean levofloxacin concentrations measured in sputum over time are shown in FIG. 11. Levofloxacin delivered with MgCl$_2$ is retained in sputum for a longer period and at higher concentrations than the same dose of levofloxacin delivered in saline.

Further comparison of the PK parameters in CF sputum for aerosol administration of levofloxacin in saline (Example 4-Table 8) indicate that both a significantly higher sputum C$_{max}$ and AUC are achieved by complexation with magnesium (e.g., Cmax is 211.5 mg/L levofloxacin vs. 388 for levofloxacin:Mg and AUC is 171.4 h·mg/L levofloxacin/saline vs. 851 h·mg/L levofloxacin:Mg for 40 mg respirable dose).

Example 7

Pharmacokinetics of Levofloxacin in CF Patients Following Aerosol Administration of Formulations Containing MgCl$_2$ Plus Lactose for Up to 14 Days CF patients received respirable delivered doses of approximately 40 mg, 80 mg, or 120 mg per treatment (loaded doses of 78 mg, 175 mg, or 260 mg per treatment) on day 1 followed by twice daily dosing for 14 days. Formulations shown in Table 11 were used. Standard non-compartmental and compartmental PK methods were used to generate serum, sputum, and urinary PK parameters (Gibaldi M, Perrier B. Pharmacokinetics. 2nd ed. New York:Marcel-Dekker; 1982, incorporated by reference herein in its entirety). PK parameters were determined for serum and sputum and are shown in Tables 13 and 14, respectively. Comparison with the administration of levofloxacin in saline (Example 4) indicate that both a significantly higher sputum Cmax and AUC are achieved by complexation with magnesium (e.g., Cmax is 211.5 mg/L levofloxacin vs. 448.97 for levofloxacin:Mg and AUC is 171.4 h·mg/L levofloxacin vs. 420.54 h·mg/L levofloxacin:Mg (day 1) for 40 mg respirable dose).

TABLE 13

| | Parameter | Loaded Levofloxacin Dose (Mean ± SD) | | |
|---|---|---|---|---|
| | | 78 mg (n = 10) RDD: 40 mg | 175 mg (n = 10) RDD: 80 mg | 260 mg (n = 10) RDD: 120 mg |
| Day 1 | Serum C$_{max}$ (mg/L) | 0.36 ± 0.6 | 1.05 ± 0.29 | 1.34 ± 0.42 |
| | Serum T$_{max}$ (h) | 0.21 | 1.00 | 0.29 |
| | Serum AUC$_{(0-t)}$ (h·mg/L) | 2.2.61 ± 1.81 | 9.12 ± 1.89 | 10.24 ± 3.08 |
| | Serum AUC$_{(inf)}$ (h·mg/L) | 3.40 ± 1.69 | 9.94 ± 2.30 | 11.44 ± 2.86 |
| | Serum t½ (h) | 7.21 ± 1.89 | 6.60 ± 0.91 | 7.36 ± 2.42 |
| Day 15 | Serum C$_{max}$ (mg/L) | 0.58 ± 0.35 | 1.37 ± 0.56 | 2.39 ± 0.56 |
| | Serum T$_{max}$ (h) | 0.53 | 0.98 | 0.22 |
| | Serum AUC$_{(0-t)}$ (h·mg/L) | 5.16 ± 1.22 | 12.95 ± 5.75 | 18.12 ± 12.00 |
| | Serum t½ (h) | 8.48 ± 2.42 | 6.52 ± 0.87 | 6.62 ± 1.16 |

TABLE 14

| | Parameter | Loaded Levofloxacin Dose (Mean ± SD) | | |
|---|---|---|---|---|
| | | 78 mg (n = 10) RDD: 40 mg | 175 mg (n = 10) RDD: 80 mg | 260 mg (n = 10) RDD: 120 mg |
| Day 1 | Sputum C$_{max}$ (mg/L) | 448.97 ± 875.02 | 1333.96 ± 1146.55 | 1766.23 ± 1493.52 |
| | Sputum T$_{max}$ (h) | 0.52 | 0.53 | 0.54 |
| | Sputum AUC$_{(0-t)}$ (h·mg/L) | 420.54 ± 994.99 | 1468.60 ± 1420.04 | 1779.23 ± 1223.12 |
| | Sputum t½ (h) | 1.54 ± 0.56 | 2.56 ± 1.94 | 5.04 |
| Day 15 | Sputum C$_{max}$ (mg/L) | 612.06 ± 1440.13 | 1258.82 ± 1888.15 | 1721.51 ± 1511.15 |
| | Sputum T$_{max}$ (h) | 0.52 | 0.53 | 0.50 |
| | Sputum AUC$_{(0-t)}$ (h·mg/L) | 637.56 ± 1280.39 | 1642.81 ± 2849.76 | 1272.76 ± 795.19 |
| | Sputum t½ (h) | 9.96 ± 13.9 | 4.10 ± 1.93 | 2.73 ± 1.58 |

Example 8

Aerosol Administration of 50 mg/ml and 100 mg/ml Solutions of Levofloxacin Formulated with MgCl₂

This example relates to aerosol administration to CF patients of 50 mg/ml and 100 mg/ml solutions of levofloxacin formulated with MgCl₂ at doses of 180 mg and 240 mg. Table 15 shows the formulations of levofloxacin with MgCl₂.

TABLE 15

|  | 50 mg/ml | 100 mg/ml |
| --- | --- | --- |
| Levofloxacin, mg/ml | 50 | 100 |
| Magnesium, mg/ml (mM) | 2.4 (100) | 4.9 (200) |
| Chloride, mg/ml (mM) | 7.1 (200) | 14.2 (400) |
| Lactose, mg/ml (mM) | 51.4 (150) | 0 (0) |
| pH | 6-8 | 6-8 |
| Osmolality, mOsm/kg | 300-500 | 300-500 |

Levofloxacin with MgCl₂ was administered by inhalation using a PARI eFlow nebulizer using vibrating mesh technology with the 35 L head configuration. Subjects received, in an order specified by a randomization schedule, a single 180 mg dose of a particular formulation (50 mg/ml or 100 mg/ml) in Period 1 of the study, followed by a 7-day wash-out period and a single 180 mg dose of the other formulation (50 mg/ml or 100 mg/ml) in Period 2. This was followed by 7 consecutive days of a once-daily 240 mg dose during Period 3. Serum and sputum concentrations of levofloxacin were measured using an HPLC/fluorescence method.

Figure 12:
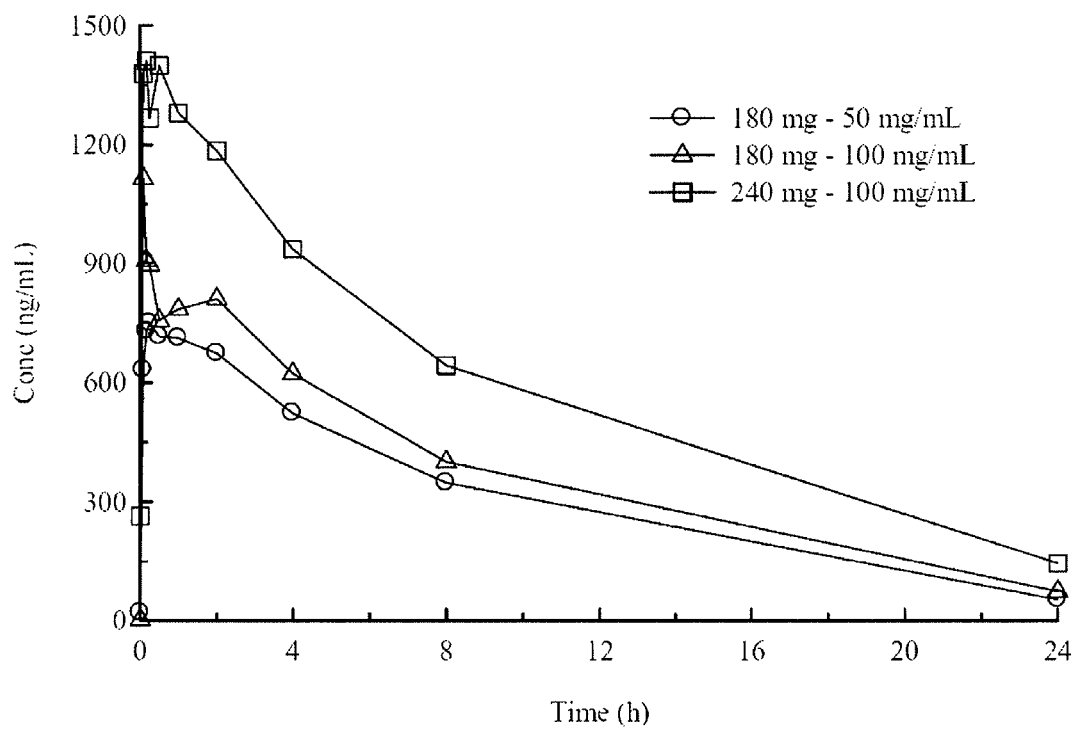
FIG. 12 shows a graph of the arithmetic mean serum concentrations of levofloxacin in cystic fibrosis patients, after aerosol administration of a 180 mg dose with 50 mg/ml or 100 mg/ml levofloxacin solution, or a 240 mg dose with a 100 mg/ml levofloxacin solution. Treatment was once daily for 7 days. The 50 mg/ml levofloxacin formulation contained 100 mM magnesium chloride and 150 mM lactose, and the 100 mg/ml levofloxacin contained 200 mM magnesium chloride and no lactose.

With respect to serum concentrations of levofloxacin, the arithmetic mean serum concentrations of levofloxacin after administration of 180 mg with the 100 mg/ml formulation were slightly higher than after administration with the 50 mg/ml formulation (FIG. 12). Table 16 summarizes pharmacokinetic parameters for levofloxacin after administration of single 180 mg doses as a 50 mg/ml or 100 mg/ml solution for inhalation, and after administration of 240 mg as a 100 mg/ml solution for inhalation once daily for 7 days to patients with CF. The mean $C_{max}$ and $AUC_{(inf)}$ for the 100 mg/ml formulation were 35% and 22% higher than the corresponding values for the 50 mg/ml formulation.

TABLE 16

| Parameter[1] | Dose: 180 mg | | Dose: 240 mg |
| --- | --- | --- | --- |
|  | 50 mg/ml | 100 mg/ml | 100 mg/ml |
| Serum $C_{max}$ (ng/ml) | 952 ± 617 (10) | 1,284 ± 642 (10) | 1,707 ± 624 (10) |
| Serum $T_{max}$ (h) | 0.25 (10) | 0.17 (10) | 0.3 (10) |
| Serum $C_{min}$ (ng/ml) | 58.5 ± 60.4 (10) | 73.5 ± 45.8 (10) | 145 ± 172 (10) |
| Serum $AUC_{(0-t)}$ (h · ng/ml) | 7,074 ± 3,625 (10) | 9,054 ± 3,411 (10) | 14,771 ± 9,969 (10) |
| Serum $AUC_{(inf)}$ (h · ng/ml) | 8,058 ± 3,704 (9) | 9,848 ± 3,813 (10) | 16,930 ± 13,631 (10) |
| Serum $t^{1/2}$ (h) | 6.40 ± 1.27 (9) | 6.78 ± 1.61 (10) | 7.49 ± 2.89 (10) |

[1]Arithmetic mean ± standard deviation (N) except for $T_{max}$ for which the median (N) is reported.

Based on a mean $t^{1/2}$ of 6.78 h after administration of 180 mg with the 100 mg/ml formulation, the accumulation with once-daily dosing should be about 9%. There was a 1.33-fold increase in the mean $C_{max}$ after administration of 240 mg with the 100 mg/ml formulation, similar to the increase in level of dose. $AUC_{(0-t)}$ on Day 7 after administration of 240 mg QD×7 days is $AUC_{(0-24)}$, or the AUC over the dosing interval, which should be equivalent to $AUC_{(inf)}$ after a single dose. Correcting the 14,771 h·ng/ml mean $AUC_{(0-t)}$ of the 240 mg dose level to the 180 mg dose level, results in an estimate of 11,078 h·ng/ml, comparable to the observed $AUC_{(inf)}$ of 9,848±3,813 h·ng/ml after administration of a single 180 mg dose of the same formulation. This demonstrates the linearity of the pharmacokinetics of levofloxacin after single and multiple aerosol doses of levofloxacin with the 100 mg/ml formulation. The arithmetic mean $t^{1/2}$ was comparable for all three treatments, ranging from 6.40 h to 7.49 h.

Figure 13:
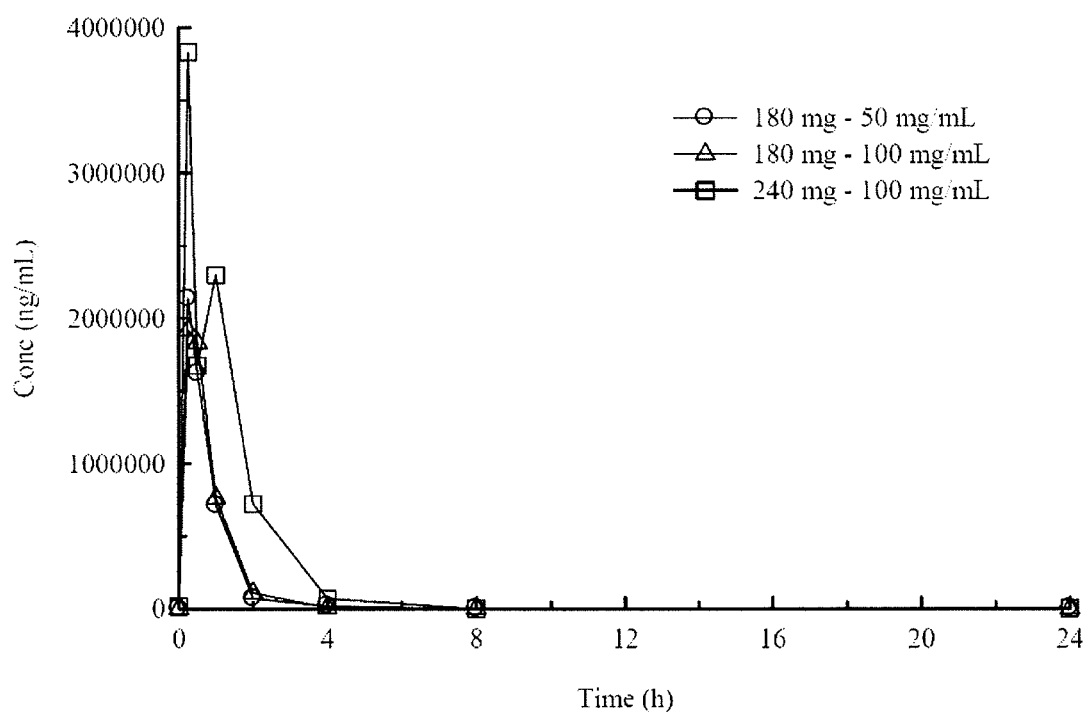
FIG. 13 shows a graph of the arithmetic mean sputum concentrations of levofloxacin in cystic fibrosis patients, after aerosol administration of a 180 mg dose with 50 mg/ml or 100 mg/ml levofloxacin solution, or a 240 mg dose with a 100 mg/ml levofloxacin solution. Treatment was once daily for 7 days. The 50 mg/ml levofloxacin formulation contained 100 mM magnesium chloride and 150 mM lactose, and the 100 mg/ml levofloxacin contained 200 mM magnesium chloride and no lactose.

With respect to sputum concentrations of levofloxacin, mean values for arithmetic sputum concentration, $C_{max}$, and AUC were similar after administration of 180 mg with either the 50 mg/ml or 100 mg/ml formulation (FIG. 13). Table 17 summarizes sputum pharmacokinetic parameters for levofloxacin after administration of single 180 mg doses as a 50 mg/ml or 100 mg/ml solution for inhalation, and after administration of 240 mg as a 100 mg/ml solution for inhalation once daily for 7 days to patients with CF.

TABLE 17

| Parameter[1] | Loaded Dose: 180 mg | | Loaded Dose: 240 mg |
|---|---|---|---|
| | 50 mg/ml | 100 mg/ml | 100 mg/ml |
| Sputum $C_{max}$ (ng/ml) | 2,563,119 ± 1,411,715 (10) | 2,932,121 ± 2,559,422 (10) | 4,690,808 ± 4,515,727 (10) |
| Sputum $T_{max}$ (h) | 0.27 (10) | 0.28 (10) | 0.29 (10) |
| Sputum $C_{min}$ (ng/ml) | 398 ± 482 (10) | 278 ± 192 (10) | 697 ± 939 (10) |
| Sputum $AUC_{(0-t)}$ (h · ng/ml) | 1,889,669 ± 1,252,341 (10) | 1,958,819 ± 2,109,909 (10) | 4,507,180 ± 6,593,884 (10) |
| Sputum $AUC_{(inf)}$ (h · ng/ml) | 1,890,699 ± 1,252,486 (10) | 1,960,771 ± 2,110,392 (10) | 4,517,439 ± 6,611,353 (10) |
| Sputum $t^{1/2}$ (h) | 3.55 ± 2.69 (10) | 4.34 ± 1.80 (10) | 4.58 ± 2.54 (10) |

[1]Arithmetic mean ± standard deviation (N) except for $T_{max}$ for which the median (N) is reported.

There was a 1.6-fold increase in $C_{max}$ between the 180 mg and 240 mg doses of the 100 mg/ml formulation, of 2,932,121 ng/ml to 4,690,808 ng/ml (Table 17). In view of the small number of patients and variability between subjects, this increase is reasonably consistent with a predicted increase of about 1.33-fold. In contrast, there was a 2.3-fold increase in AUC, from 1,960,771 h·ng/ml [$AUC_{(inf)}$] to 4,507,180 h·ng/ml [$AUC_{(0-24)}$]. The arithmetic mean t'/2 was comparable for all three treatments, ranging from 3.55 h to 4.58 h (Table 16).

These results show that levofloxacin exposure in sputum was orders of magnitude higher than that in serum (Tables 16 and 17). However, the ratio of levofloxacin exposure in sputum to that in serum was relatively independent of the formulation and the dose, and averaged approximately 260,000% for $C_{max}$, and 25,000% for AUC (Table 18).

TABLE 18

| | Sputum/Serum Ratio | | |
|---|---|---|---|
| | Dose: 180 mg | | Dose: 240 mg |
| Parameter | 50 mg/ml | 100 mg/ml | 100 mg/ml |
| $C_{max}$ (ng/ml) | 269,336 | 228,271 | 274,796 |
| AUC (h · ng/ml)[1] | 23,462 | 19,911 | 30,514 |

[1]$AUC_{(inf)}$ for the single 180 mg doses and $AUC_{(0-t)}$ for the multiple 240 mg dose.

Sputum exposure is similar for both formulations. Taking into account potential accumulation from the 240 mg QD×7-day regimen, the systemic and sputum exposure after administration of 180 mg and 240 mg as the 100 mg/ml formulation appear to be proportional to dose and consistent between single and multiple doses.

Table 19 compares levofloxacin AUC and $C_{max}$ results following nebulization of formulations shown in Examples 4 and 8 as the raw results or normalized to the RDD or nebulizer loaded dose for each formulation tested.

TABLE 19

Dose-normalized Sputum Levofloxacin PK Parameters in CF Patients

| | Example | | | | |
|---|---|---|---|---|---|
| | Example 4 formulations | | Example 8 formulations | | |
| | | | Formulation/Dose | | |
| | Dose Level A Levofloxacin (12 mg/ml) | Dose Level B Levofloxacin (23.8 mg/ml) | Dose Level C Levofloxacin (50 mg/ml) with MgCl$_2$ and Lactose | Dose Level C Levofloxacin (100 mg/ml) with MgCl$_2$ | Dose Level D Levofloxacin (100 mg/ml) with MgCl$_2$ |
| Loaded Dose | 43.3 | 86.6 | 180 | 180 | 240 |
| Estimated RDD | 20 | 40 | 92 | 98 | 131 |
| $C_{max}$ (ng/ml) | 86,200 | 211,500 | 2,563,119 | 2,932,121 | 4,690,808 |
| AUC (hr · ng/ml) | 67,100 | 171,400 | 1,890,699 | 1,960,771 | 4,517,439 |
| Loaded Dose-normalized $C_{max}$ (ng/ml per mg dose) | 1,991 | 2,442 | 14,240 | 16,290 | 19,545 |
| Loaded Dose-normalized AUC (hr · ng/ml per mg dose) | 1,550 | 1,979 | 10,504 | 10,893 | 18,823 |
| RDD - normalized $C_{max}$ (ng/ml per mg dose) | 4,310 | 5,288 | 27,866 | 29,862 | 35,830 |
| RDD - normalized AUC (hr · ng/ml per mg dose) | 3,355 | 4,285 | 20,556 | 19,969 | 34,505 |

Figure 14:
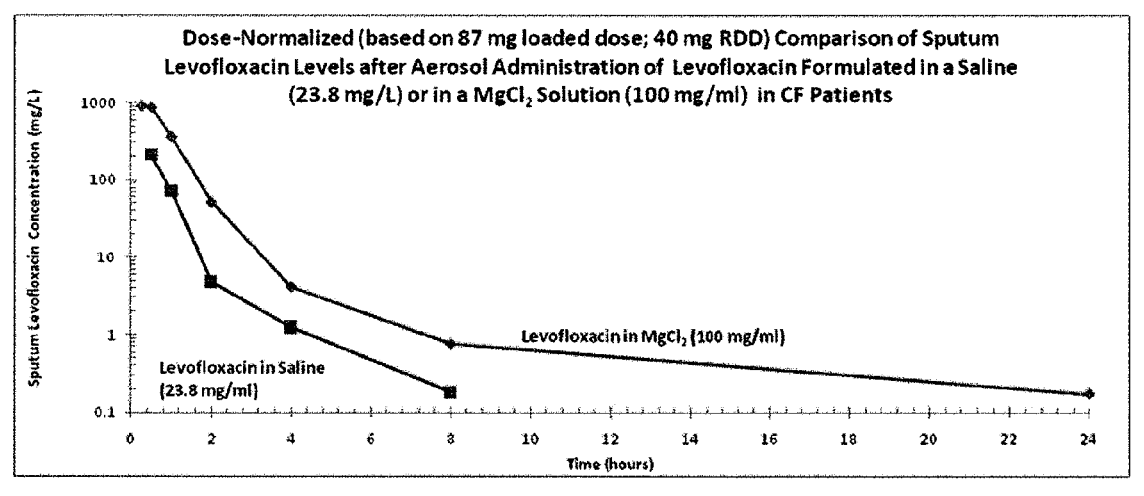

The dose-normalized AUC and $C_{max}$ PK parameters show the significantly increased exposures of levofloxacin in sputum using the formulations of Example 8 that include levofloxacin formulated with $Mg^{2+}$ over the formulations of Example 4 that lack $Mg^{2+}$. The differences in sputum concentrations of levofloxacin between Example 4 and Example 8 formulations are further shown in FIG. 14.

Example 9

Mouse Lung Infection Model

A mouse lung infection model was used to compare the efficacy of intravenous administration with pulmonary administration of fluoroquinolones. Eight mice per group were infected with *Klebsiella pneumoniae* ATCC 43816 by intra-tracheal instillation. Twenty-four hours after infection, mice were administered aerosol doses of 10 or 20 mg/kg twice daily (BID) using a microspray aerosol generation device (PennCentury, Philadelphia, Pa.). Twenty-four hours after beginning treatment, animals were sacrificed and their lungs were removed, homogenized, and plated to determine colony counts. Table 20 shows the formulations used in this study.

TABLE 20

|  | Levofloxacin in saline | | Levofloxacin with MgCl$_2$ | |
|---|---|---|---|---|
| Dose (mg/kg) | 10 | 20 | 10 | 20 |
| Levofloxacin (mg/mL) | 4 | 8 | 4 | 8 |
| MgCl$_2$ (mM) | 0 | 0 | 8 | 16 |
| Saline (%) | 0.9 | 0.9 | 0 | 0 |
| Lactose (mM) | 0 | 0 | 12 | 24 |

Figure 15:
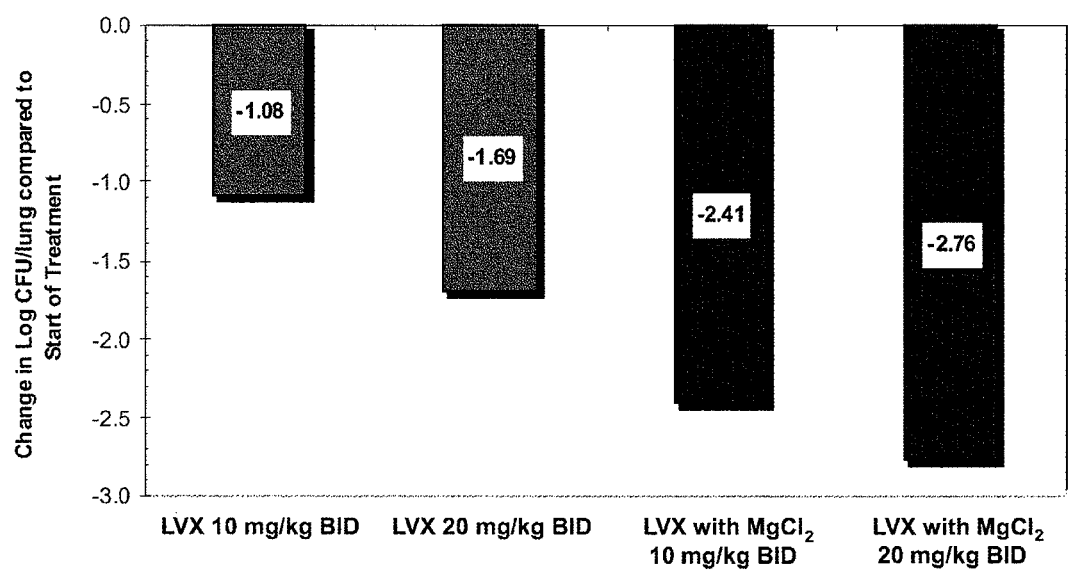
FIG. 15 shows a graph of the change in log colony forming units (CFU) of *K. pneumoniae* ATCC 43816/lung in mice, after aerosol administration of 10 mg/kg or 20 mg/kg doses of levofloxacin (LVX) formulated with and without $MgCl_2$.

Levofloxacin formulated with MgCl$_2$ produced 1 log greater bacterial killing than levofloxacin formulated in saline at each dose tested (FIG. 15). This result is consistent with the increased lung concentrations determined in the rat in Example 2.

Example 10

Efficacy of Aerosol Levofloxacin Formulated with MgCl$_2$ in Mouse Lung Infection Models This example relates to aerosol administration of levofloxacin with MgCl$_2$, and intraperiteneal administration of levofloxacin in saline. The purpose of the following studies was to determine the efficacy of these therapies in acute and chronic lung infection models due to *P. aeruginosa*.

Antimicrobial agents: Levofloxacin (LKT Laboratories, St. Paul, Minn.), tobramycin (Sicor pharmaceuticals, Irvine, Calif.), and aztreonam (MP Biomedicals, Solon, Ohio) were purchased from independent vendors. Prior to the initiation of each experiment, fresh stock solutions of each antibiotic were prepared. Levofloxacin formulated with MgCl$_2$ was diluted in water; levofloxacin and tobramycin were diluted in 0.9% saline, aztreonam was diluted in 7% sodium bicarbonate in water. Table 21 shows formulations used in this study.

TABLE 21

|  | Levofloxacin in Saline | | | Levofloxacin with MgCl$_2$ | | |
|---|---|---|---|---|---|---|
| Dose (mg/kg) | 32 | 63 | 125 | 32 | 63 | 125 |
| Levofloxacin (mg/mL) | 1.5 | 3 | 6 | 6 | 12 | 24 |
| MgCl$_2$ (mM) | 0 | 0 | 0 | 12 | 24 | 48 |
| Saline (%) | 0.9 | 0.9 | 0.9 | 0 | 0 | 0 |

Bacterial strains MIC testing: *P. aeruginosa* ATCC 27853 and NH57388A were used in these studies. MICs were determined by a broth microdilution assay according to CLSI reference methods (Methods for dilution of antimicrobial susceptibility test for bacteria that grow aerobically. Seventh Edition: Clinical and Laboratory Standards Institute (2006) M&-A7, incorporated by reference in its entirety). Assays were performed in a final volume of 100 µl. The bacterial suspensions were adjusted to yield a cell density of $5 \times 10^5$ CFU/ml. Antibiotics were prepared at a concentration equivalent to twofold the highest desired final concentration in culture medium and were then diluted directly into 96-well microtiter plates. Microtiter plates were incubated for 24 h at 35° C. and were read by using a microtiter plate reader (Molecular Devices) at 600 nm as well as by visual observation by using a microtiter plate reading mirror. The MIC was defined as the lowest concentration of antibiotic at which the visible growth of the organism is completely inhibited.

Mice: Female Swiss mice (5-6 wk of age) were obtained from Harlan West Coast (Germantown, Calif.). All studies were performed under protocols approved by an Institutional Animal Care and Use Committee.

Preparation of pseudomonal alginate: *P. aeruginosa* NH57388A was cultured in 50 ml Mueller-hinton broth (MHB) for 24-28 h at 37° C. with shaking (170 rpm). Bacterial cells were harvested by centrifugation (23,000×g, 30 min, at 4° C.) and resuspended in 3-6 ml of MHB. The supernatant was collected and placed in 80° C. water-bath for 30 min. Alginate was precipitated by adding the supernatant to 150 ml of ice-cold 99% ethanol. The precipitated alginate was collected with a sterile bacterial loop and washed several times in sterile saline. The purified alginate was then resuspended in 10 ml of sterile saline and stirred vigorously to form a homogeneous suspension. The alginate concentration was measured and adjusted to a concentration of 2-3 mg/ml.

Aerosol Administration of antibiotics: Antibiotics were aerosolized using a microspray aerosol device (MicroSprayer Model IA-C, PennCentury, Philadelphia, Pa.) attached to a FMJ-250 High-Pressure Syringe (PennCentury, Philadelphia, Pa.). This device produces a 16-22 µM Mass Medium Diameter spray. For administration, each mouse was anesthetized (5% isoflurane in oxygen running at 4 L/min) and positioned securely at a 45-50° angle by the upper teeth, the microspray aerosol tip was inserted to the bifurcation and a 50 µl volume was administered.

Pharmacokinetics: Mice (n=3/timepoint) were administered single 60 mg/kg aerosol dose of levofloxacin formulated with MgCl$_2$ or a 20 mg/kg IP dose of levofloxacin. Mice were sacrificed at 0.08, 0.16, 0.25, 0.5, 0.75, 1.0, 2.0, 3.0, and 4.0 h after dosing and their lungs collected. Levofloxacin lung homogenate concentrations administered as levofloxacin or levofloxacin formulated with MgCl$_2$ were measured using an HPLC method. Analytical standards (0.05 to 100 mg/L) were prepared in fresh mouse lung homogenate collected from untreated animals. Lung homogenate or standards for both compounds were mixed with double the volume of 4% trichloroacetic acid, vortexed and then centrifuged at 12,000 rpm for 10 min using a refrigerated Eppendorf 5415c centrifuge set at 4-10° C. Aliquots of the supernatant (25 µl) were injected directly onto the HPLC using a temperature-controlled autoinjector set at 10° C. Standard curves were constructed of the peak area versus standard concentration, and the data were fit using weighted linear regression (Microsoft Excel, Seattle, Wash.). The concentrations of levofloxacin in the lung homogenate were calculated from these standard curves. The lung pharmacokinetic parameters were determined using WinNonlin (Pharsight, Mountain View, Calif.).

Acute Mouse Lung Infection Model: $P.$ aeruginosa ATCC 27853 was grown overnight in MHB at 35° C. The bacterial suspensions were adjusted to approximately $1-6\times10^5$ CFU/ml by correlation of the absorbance at 600 nm with predetermined plate counts. Female Swiss mice were made neutropenic by the intraperitoneal (IP) injection of 150 mg/kg cyclophosphamide (Baxter, Deerfield) on days 1 and 3. On day 4, mice were infected by intratracheal (IT) instillation of 0.05 ml of inoculum using a curved oral gavage tip attached to a 1 ml syringe. Antibiotic treatments started 24 h post-infection and were administered once or twice daily for 24 or 48 h. Antibiotics were aerosolized using a microspray aerosol device. All infections and aerosol treatments were performed under isoflurane anesthesia (5% isoflurane in oxygen running at 4 L/min). An untreated group of mice (n=8) was sacrificed prior to the initiation of treatment to determine baseline bacterial counts. The treated animals (n=8) were sacrificed 12-16 h following the last antibiotic dose by carbon dioxide asphyxiation. The lungs were removed aseptically and homogenized (Pro200 homogenizer, Pro Scientific, Monroe, Conn.) in 1 ml of sterile saline. Serial 10-fold dilutions of the homogenized lung were plated on Mueller-hinton agar (MHA), and colonies counted. For survival studies, mice (n=10) were observed for 7 days after the end of treatment or a total of 9 days post-infection.

Chronic Mouse Lung Infection Model: $P.$ aeruginosa NH57388A was cultured in 50 ml MHB for 24-28 h at 37° C. with shaking (170 rpm). Bacterial cells were harvested by centrifugation (23,000×g, 30 min, at 4° C.) and resuspended in 3-6 ml of MHB (Hoffmann, N. T. B. et al. 2005. Novel mouse model of chronic Pseudomonas aeruginosa lung infection mimicking cystic fibrosis. Infect Immun 73:2504-14, incorporated herein by reference in its entirety). The bacterial suspension was diluted (1:10) in the alginate suspension to yield about $10^8$ CFU/ml. Initial establishment of infection was achieved by a transient neutropenia using a single 150 mg/kg IP dose of cyclophosphamide 4 days prior to infection. On day 4, the mice were infected using a curved bead-tipped oral gavage attached to a 1 ml syringe while under isoflurane anesthesia. Antibiotic treatments started 24 h post-infection and were administered twice daily for three consecutive days with various concentrations of antibiotics either by the IP route or by aerosol using a microspray device. 12-16 h following the last treatment, mice were sacrificed and colony counts in the lung determined as described herein.

Statistical Analysis: Survival and lung bacterial counts were analyzed by log-rank and the Mann-Whitney U test (GraphPad Prism version of 4.03), respectively. A P value of <0.05 was considered statistically significant.

Minimal Inhibitory Concentration of Antibiotics

The minimal inhibitory concentration (MIC) of the $P.$ aeruginosa strains used in animal studies are shown in Table 22. Tobramycin was the most potent antibiotic in vitro, with MICs of <1 µg/ml, levofloxacin formulated with $MgCl_2$ and levofloxacin had MICs of 1 and 2 µg/ml, and aztreonam had MICs of 4 µg/ml against both strains

TABLE 22

| | MIC (µg/ml) | | | |
| --- | --- | --- | --- | --- |
| $P.$ aeruginosa strain | Levofloxacin formulated with $MgCl_2$ | Levo-floxacin | Tobramycin | Aztreonam |
| ATCC27853 | 1 | 1 | 0.25 | 4 |
| NIH57388A CF | 2 | 2 | 0.5 | 4 |

Mouse Pharmacokinetics

Normalized lung pharmacokinetic parameters for levofloxacin formulated with $MgCl_2$ and levofloxacin are shown in Table 23. Aerosol administration of 60 mg/kg levofloxacin formulated with $MgCl_2$ produced values for levofloxacin AUC and $C_{max}$ that were 9 and 30-fold higher than those achieved with dose normalized intraperitoneal administration of levofloxacin.

TABLE 23

| Parameter | Levofloxacin formulated with $MgCl_2$ | Levofloxacin formulated in Saline |
| --- | --- | --- |
| Route of Administration | Aerosol | IP |
| Dose (mg/kg) | 60 | 20 |
| $C_{max}$ (mg/kg) (Normalized to 60 mg/kg) | 550 | 6.2 (18.6) |
| AUC (hr · mg/kg) (Normalized to 60 mg/kg) | 106 | 4.1 (12.3) |

Figure 16:
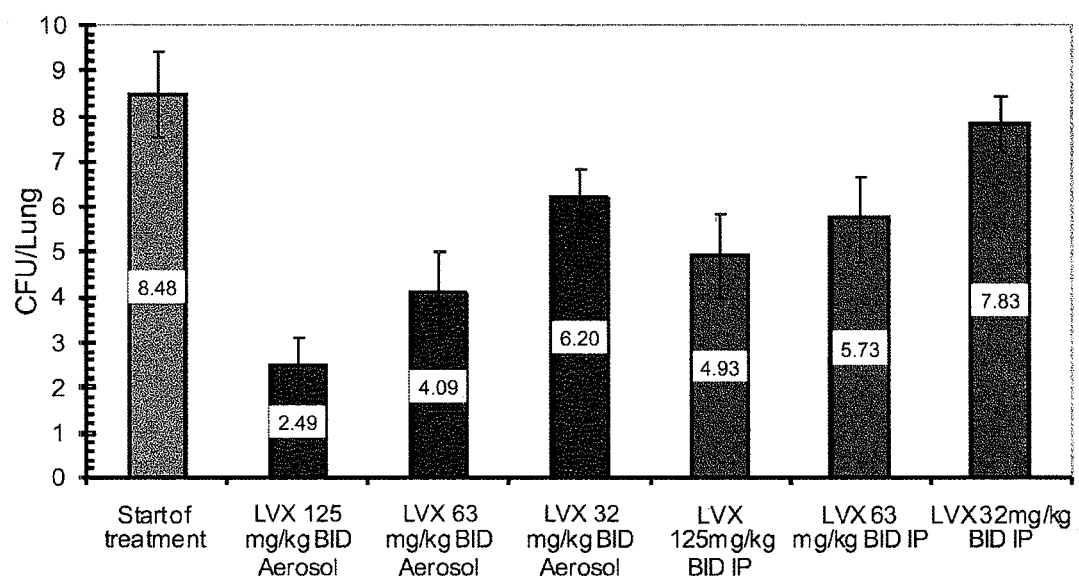
FIG. 16 shows a graph of the log colony forming units (CFU) of *P. aeruginosa* ATCC 27853/lung in a mouse acute lung infection model, after aerosol administration of 125 mg/kg, 63 mg/kg, or 32 mg/kg levofloxacin (LVX) with $MgCl_2$, or intraperitoneal administration (IP) of 125 mg/kg, 63 mg/kg, or 32 mg/kg levofloxacin. Values shown are mean±SD log CFU/lung. Treatment groups (n=8) received 2 doses of antibiotics over 24 h. ($p<0.05$ for comparisons of aerosol vs. IP administration for each dose).
Figure 17:
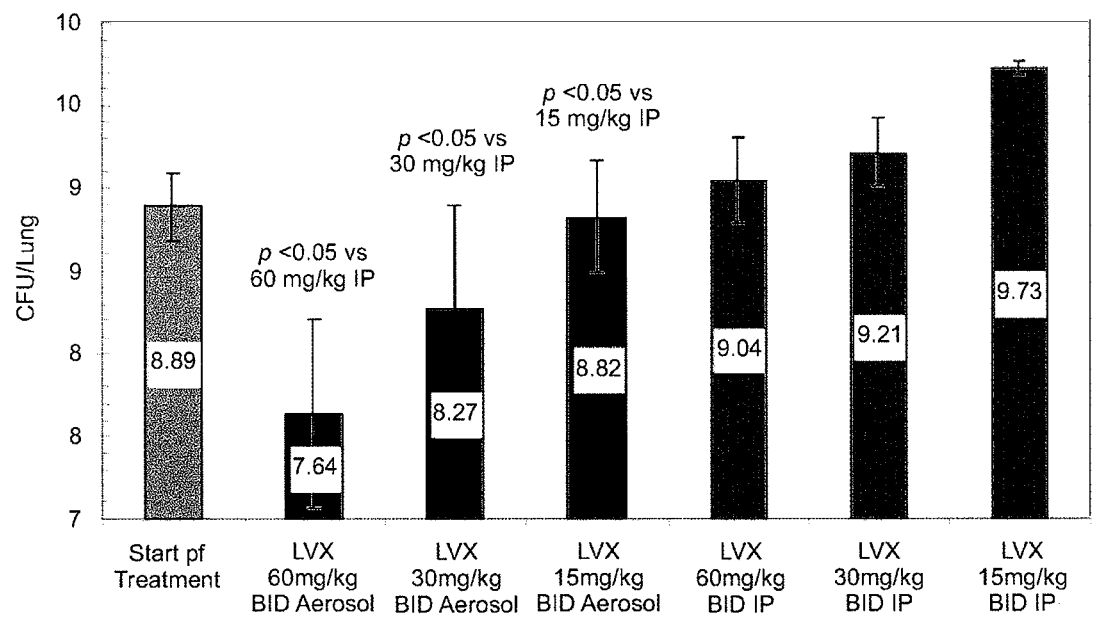
FIG. 17 shows a graph of log colony forming units (CFU) of *P. aeruginosa* NH57388A/lung in a murine chronic lung infection model, after twice daily aerosol administration of 60 mg/kg, 30 mg/kg, or 15 mg/kg levofloxacin (LVX) with $MgCl_2$, or twice daily intraperitoneal administration of 60 mg/kg, 30 mg/kg, or 15 mg/kg levofloxacin. Aerosol doses of levofloxacin were formulated in magnesium chloride. Values shown are mean±SD log CFU/lung. Treatment groups (n=8) received 2 doses of antibiotics per day for 72 h. ($p<0.05$ for comparison of aerosol vs intraperitoneal for the same dose).

Aerosol Levofloxacin Formulated with $MgCl_2$ Vs. Systemic Levofloxacin in Acute and Chronic Lung Infection Models In the acute lung infection model, aerosol treatment with 125, 62.5, and 32 mg/kg of levofloxacin formulated with $MgCl_2$ produced 5.9, 4.3, and 2.3 log CFU reductions in lung bacterial counts, respectively (FIG. 16). Systemic treatment with 125, 62.5, and 32 mg/kg of levofloxacin produced 3.5, 2.7, and 0.65 log CFU reductions, respectively. The reduction in bacterial counts with aerosol levofloxacin formulated with $MgCl_2$ was greater than that observed with IP levofloxacin on a per dose basis (p<0.05).

In the chronic lung infection model, intraperitoneal treatment with 60, 30, and 15 mg/kg of levofloxacin in saline produced a 0.15, 0.32, and 0.83 log increase in bacterial counts, respectively (FIG. 17). In contrast, aerosol dosing with 60, 30, and 15 mg/kg of levofloxacin formulated with $MgCl_2$ produced 1.26, 0.62, and 0.07 log decreases in bacterial counts, respectively. Overall, bacterial load in the lung was significantly lower in mice treated with aerosolized levofloxacin formulated with $MgCl_2$ compared to systemic levofloxacin on a dose per dose basis in both infection models (p<0.05 for levofloxacin formulated with MgCl₂ vs. systemic levofloxacin).

Aerosol Levofloxacin, Tobramycin, and Aztreonam in an Acute Lethal Lung Infection Model To compare the effects of levofloxacin formulated with MgCl₂, tobramycin, and aztreonam in the acute lung infection model, mice were infected with *P. aeruginosa* ATCC 27853 and treated by the aerosol route twice a day for 2 consecutive days. Due to toxicity, tobramycin was limited to a 60 mg/kg maximum dose and aztreonam was limited to 400 mg/kg maximum dose. In addition, due to the need for anesthesia for treatment, the maximum number of daily doses was limited to two.

Figure 18:
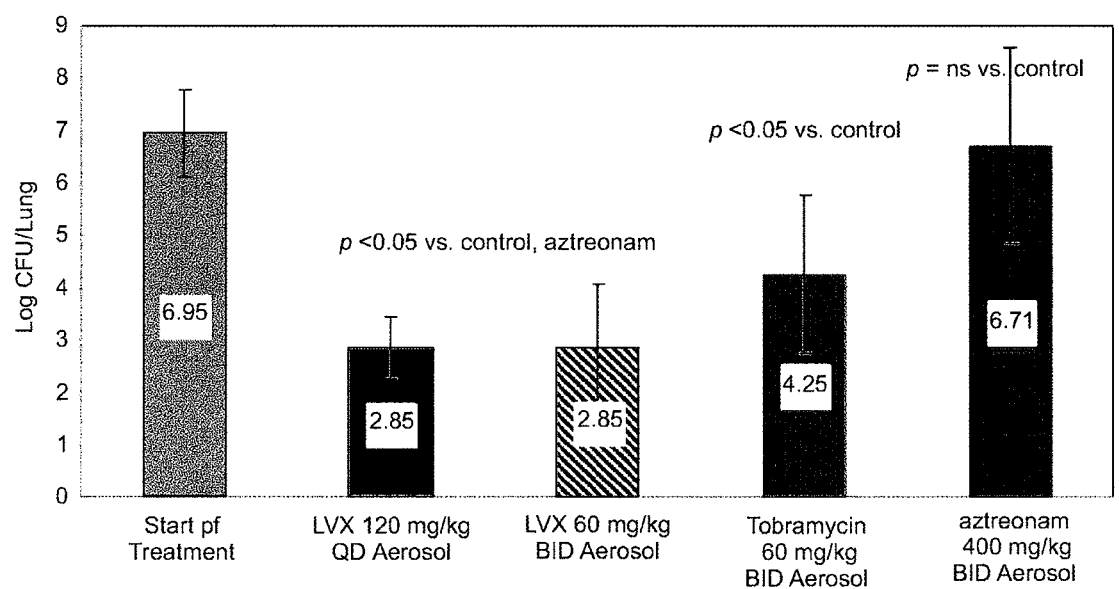
FIG. 18 shows a graph of log colony forming units (CFU) of *P. aeruginosa* ATCC 27853/lung in a murine acute lethal lung infection model, after twice daily aerosol administration of 60 mg/kg of levofloxacin, 60 mg/kg tobramycin, or 400 mg/kg aztreonam, or once daily aerosol administration of 120 mg/kg levofloxacin. Aerosol doses of levofloxacin were formulated in magnesium chloride. Treatment groups (n=8) received drug for 48 h. Values shown are mean±SD log CFU/lung. ($p<0.05$).

As shown in FIG. 18, aerosol dosing with levofloxacin formulated with MgCl₂, tobramycin, and aztreonam produced mean reductions of 4.10, 2.70, and 0.24 log CFU per lung, respectively ($p<0.05$ for comparisons of levofloxacin formulated with MgCl₂ with aztreonam). Notably, administration of the same total daily dose of levofloxacin formulated with MgCl₂ as single or twice daily doses resulted in similar reductions in *P. aeruginosa* counts in the lung.

Figure 19:
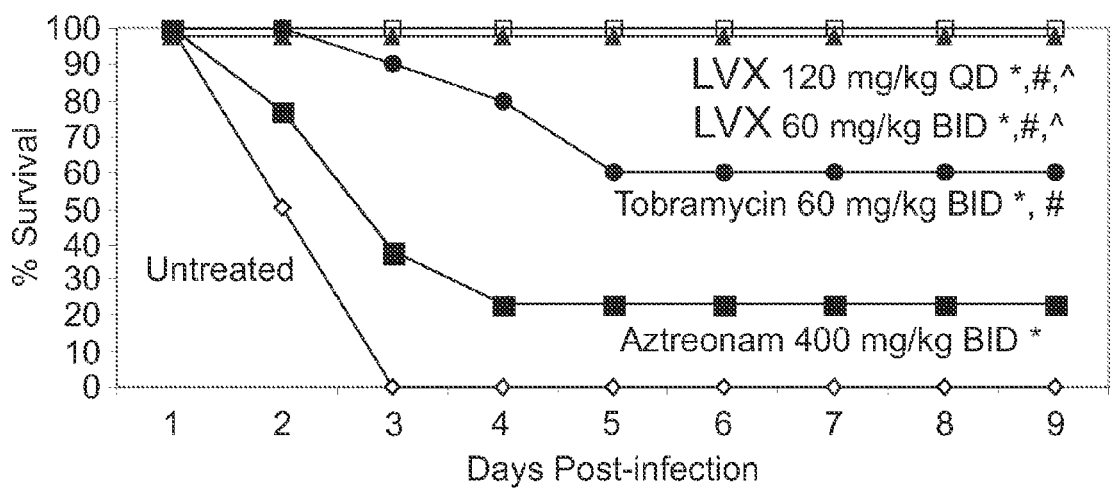
FIG. 19 shows a graph of the percent survival over time of mice infected with *P. aeruginosa* ATCC 27853 in a murine lethal lung infection model, and treated with twice daily aerosol administration of 60 mg/kg of levofloxacin, 60 mg/kg tobramycin, or 400 mg/kg aztreonam, or once daily aerosol administration of 120 mg/kg levofloxacin. Aerosol doses of levofloxacin were formulated in magnesium chloride. Treatment groups of mice (n=10) received drug for 48 h. Survival was monitored through day 9 following infection.

Survival was monitored over 9 days. As shown in FIG. 19, all untreated mice succumbed to the infection after 3 days. Treatment with 800 mg/kg/day (400 mg/kg BID) aerosolized aztreonam had the lowest survival rate among the antibiotics used in this study (20%) and was not significantly different from untreated mice (p>0.05). Treatment with 120 mg/kg/day (60 mg/kg BID) tobramycin produced a 60% survival rate which was statistically different than controls (p<0.05). Treatment with 120 mg/kg/day levofloxacin formulated with MgCl₂ as either 120 mg/kg QD or 60 mg/kg BID produced 100% survival which was significantly different from untreated controls or aztreonam (p<0.05), but not significantly different from tobramycin (p=0.056).

Figure 20:
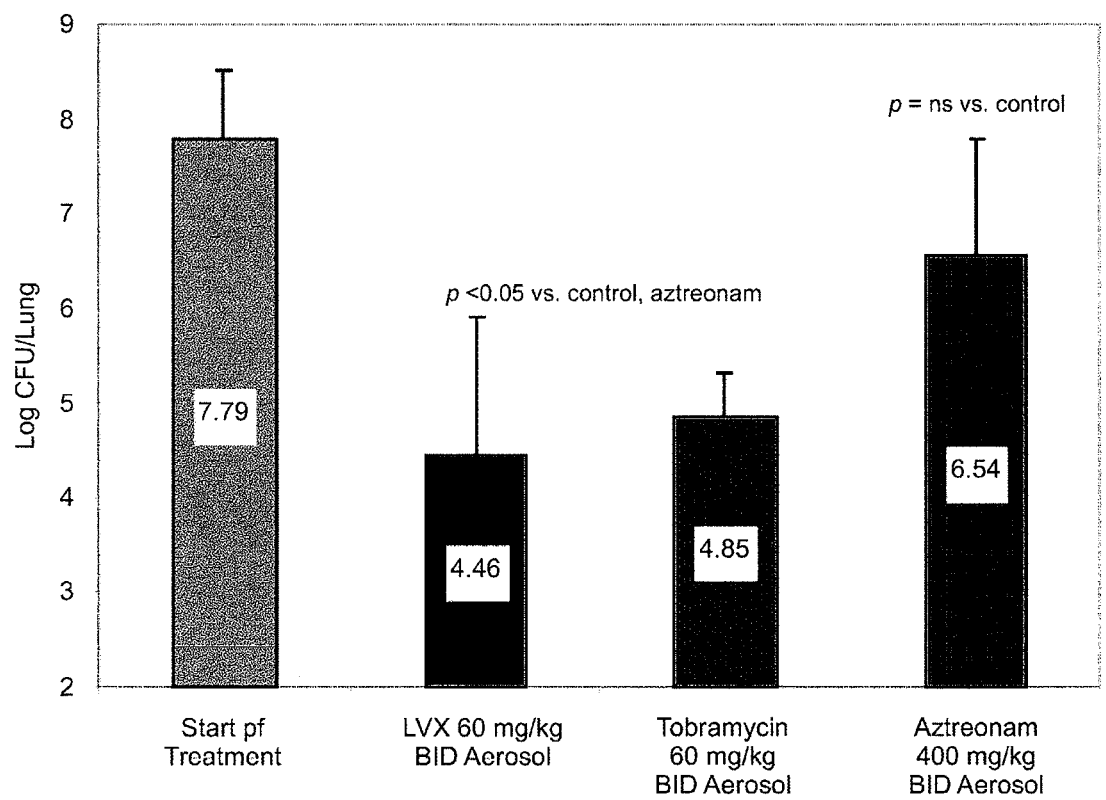
FIG. 20 shows a graph of the log colony forming units (CFU) of *P. aeruginosa* NH57388A/lung in a murine chronic lung infection model, after twice daily aerosol administration of 60 mg/kg of levofloxacin, 60 mg/kg tobramycin, or 400 mg/kg aztreonam. Treatment groups were treated twice a day for three consecutive days. Aerosol doses of levofloxacin were formulated in magnesium chloride. Values shown are mean±SD log CFU/lung. Aerosol levofloxacin resulted in lower bacterial counts than aztreonam or untreated control mice ($p<0.05$).

Aerosol Levofloxacin, Tobramycin, and Aztreonam in a Chronic Lung Infection Model Aerosolized levofloxacin formulated with MgCl₂, tobramycin and aztreonam produced mean log CFU reductions of 3.3, 2.9, and 1.25, respectively (FIG. 20). Aerosolized doses of either tobramycin or levofloxacin formulated with MgCl₂ produced significantly lower bacterial counts compared to aztreonam, or untreated control groups (p<0.05).

These in vivo studies show that aerosol dosing of levofloxacin formulated with MgCl₂ produces greater antibacterial killing than systemic dosing in both acute and chronic *P. aeruginosa* lung infection models. Notably, twice daily dosing with levofloxacin formulated with MgCl₂ reduced the lung bacterial load by an extent similar to or greater than that observed with aerosolized tobramycin and aztreonam (FIG. 18). This reduction in bacterial load in the lungs translated to improved survival (FIG. 19).

In addition, comparisons of single- versus twice-daily dosing of levofloxacin formulated with MgCl₂ showed comparable bacterial killing and survival, suggesting that once-daily treatment with levofloxacin formulated with MgCl₂ may be possible in patients. Once daily administration of a medicament is particularly advantageous over multiple administrations, where multiple administrations are inconvenient to patients and can result in poor adherence to treatment.

While preferred embodiments of the present invention have been shown and described herein, it will be obvious to those skilled in the art that such embodiments are provided by way of example only. Numerous variations, changes, and substitutions will occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

All publications, patents, and patent applications mentioned in this specification are herein incorporated by reference to the same extent as if each individual publication, patent, or patent application was specifically and individually indicated to be incorporated by reference.

What is claimed:

1. A method for treating a pulmonary infection, comprising administering to a human having said pulmonary infection an aerosol of a solution comprising levofloxacin or ofloxacin and a divalent or trivalent cation to achieve a maximum lung sputum concentration ($C_{max}$) of at least 1200 mg/L and a lung sputum area under the curve (AUC) of at least 1500 h·mg/L, wherein the solution comprises a divalent or trivalent cation concentration from about 50 mM to about 400 mM, and a levofloxacin or ofloxacin concentration from between about 50 mg/ml to about 200 mg/ml.

2. The method of claim 1, wherein the solution consists essentially of levofloxacin or ofloxacin and the divalent or trivalent cation.

3. The method of claim 1, wherein the solution comprises no lactose.

4. The method of claim 1, comprising achieving a maximum lung sputum concentration ($C_{max}$) of at least 1700 mg/L.

5. The method of claim 1, comprising achieving a maximum lung sputum concentration ($C_{max}$) of at least 2000 mg/L.

6. The method of claim 1, comprising achieving a maximum lung sputum concentration ($C_{max}$) of at least 3000 mg/L.

7. The method of claim 1, comprising achieving a maximum lung sputum concentration ($C_{max}$) of at least 4000 mg/L.

8. The method of claim 1, comprising achieving a lung sputum area under the curve (AUC) of at least 1700 h·mg/L.

9. The method of claim 1, comprising achieving a lung sputum area under the curve (AUC) of at least 2000 h·mg/L.

10. The method of claim 1, comprising achieving a lung sputum area under the curve (AUC) of at least 3000 h·mg/L.

11. The method of claim 1, comprising achieving a lung sputum area under the curve (AUC) of at least 4000 h·mg/L.

12. The method of claim 1, wherein the solution comprises a divalent or trivalent cation concentration from about 100 mM to about 300 mM, and a levofloxacin or ofloxacin concentration from about 75 mg/ml to about 150 mg/ml.

13. The method of claim 1, wherein the solution comprises a divalent or trivalent cation concentration from about 150 mM to about 250 mM, and a levofloxacin or ofloxacin concentration from about 90 mg/ml to about 125 mg/ml.

14. The method of claim 1, wherein the solution comprises an osmolality from about 300 mOsmol/kg to about 600 mOsmol/kg, and a pH from about 5 to about 8.

15. The method of claim 1, wherein the solution comprises an osmolality from about 350 mOsmol/kg to about 425 mOsmol/kg, and a pH from about 5 to about 6.5.

16. The method of claim 1, wherein the solution comprises a pH from about 5.5 to about 6.5.

17. The method of claim 1, wherein the divalent or trivalent cation is selected from magnesium, calcium, zinc, copper, aluminum, and iron.

18. The method of claim 1, wherein the solution comprises magnesium chloride.

19. The method of claim 1, wherein the solution comprises a levofloxacin or ofloxacin concentration from about 90 mg/ml to about 110 mg/ml, a magnesium chloride concentration from about 175 mM to about 225 mM, a pH from about 5 to about 7; an osmolarity from about 300 mOsmol/kg to about 500 mOsmol/kg, and lacks lactose.

20. The method of claim 1, wherein the human has a pulmonary disorder selected from the group consisting of cystic fibrosis, chronic obstructive pulmonary disease, chronic bronchitis, bronchiectasis, and asthma.

21. The method of claim 1, wherein the pulmonary infection comprises one or more bacteria selected from the group consisting of *Pseudomonas aeruginosa, Pseudomonas fluorescens, Pseudomonas acidovorans, Pseudomonas alcaligenes, Pseudomonas putida, Stenotrophomonas maltophilia, Aeromonas hydrophila, Escherichia coli, Citrobacter freundii, Salmonella typhimurium, Salmonella typhi, Salmonella paratyphi, Salmonella enteritidis, Shigella dysenteriae, Shigella flexneri, Shigella sonnei, Enterobacter cloacae, Enterobacter aerogenes, Klebsiella pneumoniae, Klebsiella oxytoca, Serratia marcescens, Morganella morganii, Proteus mirabilis, Proteus vulgaris, Providencia alcalifaciens, Providencia rettgeri, Providencia stuartii, Acinetobacter calcoaceticus, Acinetobacter haemolyticus, Yersinia enterocolitica, Yersinia pestis, Yersinia pseudotuberculosis, Yersinia intermedia, Bordetella pertussis, Bordetella parapertussis, Bordetella bronchiseptica, Haemophilus influenzae, Haemophilus parainfluenzae, Haemophilus haemolyticus, Haemophilus parahaemolyticus, Haemophilus ducreyi, Pasteurella multocida, Pasteurella haemolytica, Helicobacter pylori, Campylobacter fetus, Campylobacter jejuni, Campylobacter coli, Borrelia burgdorferi, Vibrio cholera, Vibrio parahaemolyticus, Legionella pneumophila, Listeria monocytogenes, Neisseria gonorrhoeae, Neisseria meningitidis, Burkholderia cepacia, Francisella tularensis, Kingella*, and *Moraxella*.

22. The method of claim 1, wherein the pulmonary infection is caused by a gram-negative anaerobic bacteria.

23. The method of claim 1, wherein the pulmonary infection is caused by one or more of the bacteria selected from the group consisting of *Bacteroides fragilis, Bacteroides distasonis, Bacteroides* 3452A homology group, *Bacteroides vulgatus, Bacteroides ovalus, Bacteroides thetaiotaomicron, Bacteroides uniformis, Bacteroides eggerthii*, and *Bacteroides splanchnicus*.

24. The method of claim 1, wherein the pulmonary infection is caused by a gram-positive bacteria.

25. The method of claim 1, wherein the pulmonary infection is caused by one or more of the bacteria selected from the group consisting of *Corynebacterium diphtherias, Corynebacterium ulcerans, Streptococcus pneumoniae, Streptococcus agalactiae, Streptococcus pyogenes, Streptococcus milleri; Streptococcus* (Group G); *Streptococcus* (Group C/F); *Enterococcus faecalis, Enterococcus faecium, Staphylococcus aureus, Staphylococcus epidermidis, Staphylococcus saprophyticus, Staphylococcus intermedius, Staphylococcus hyicus* subsp. *hyicus, Staphylococcus haemolyticus, Staphylococcus hominis*, and *Staphylococcus saccharolyticus*.

26. The method of claim 1, wherein the pulmonary infection is caused by a gram-positive anaerobic bacteria.

27. The method of claim 1, wherein the pulmonary infection is caused by one or more bacteria selected from the group consisting of *Clostridium difficile, Clostridium perfringens, Clostridium tetini*, and *Clostridium botulinum*.

28. The method of claim 1, wherein the pulmonary infection is caused by an acid-fast bacteria.

29. The method of claim 1, wherein the pulmonary infection is caused by one or more bacteria selected from the group consisting of *Mycobacterium tuberculosis, Mycobacterium avium, Mycobacterium intracellulare*, and *Mycobacterium leprae*.

30. The method of claim 1, wherein the pulmonary infection is caused by an atypical bacteria.

31. The method of claim 1, wherein the pulmonary infection is caused by one or more bacteria selected from the group consisting of *Chlamydia pneumoniae* and *Mycoplasma pneumoniae*.

32. The method of claim 1, wherein the aerosol comprises a mass median aerodynamic diameter from about 2 microns to about 5 microns with a geometric standard deviation less than or equal to about 2.5 microns.

33. The method of claim 1, wherein the aerosol comprises a mass median aerodynamic diameter from about 2.5 microns to about 4.5 microns with a geometric standard deviation less than or equal to about 1.8 microns.

34. The method of claim 1, wherein the aerosol comprises a mass median aerodynamic diameter from about 2.8 microns to about 4.3 microns with a geometric standard deviation less than or equal to about 2 microns.

35. The method of claim 1, comprising producing the aerosol with a vibrating mesh nebulizer.

36. The method of claim 35, wherein the vibrating mesh nebulizer is a PARI E-FLOW® nebulizer.

37. The method of claim 1, wherein a respirable drug dose (RDD) of at least about 20 mg of levofloxacin or ofloxacin is administered to the lung.

38. The method of claim 1, wherein a respirable drug dose (RDD) of at least about 100 mg of levofloxacin or ofloxacin is administered to the lung.

39. The method of claim 1, wherein a respirable drug dose (RDD) of at least about 125 mg of levofloxacin or ofloxacin is administered to the lung.

40. The method of claim 1, wherein a respirable drug dose (RDD) of at least about 150 mg of levofloxacin or ofloxacin is administered to the lung.

41. The method of claim 1, wherein a loaded dose of at least about 100 mg is aerosolized.

42. The method of claim 1, wherein a loaded dose of at least about 200 mg is aerosolized.

43. The method of claim 1, wherein a loaded dose of at least about 300 mg is aerosolized.

44. The method of claim 1, wherein the aerosol is administered to the lung in less than about 10 minutes.

45. The method of claim 1, wherein the aerosol is administered to the lung in less than about 5 minutes.

46. The method of claim 1, wherein the aerosol is administered to the lung in less than about 3 minutes.

47. The method of claim 1, wherein the aerosol is administered to the lung in less than about 2 minutes.

48. The method of claim 1, further comprising co-administering an additional active agent selected from the group consisting of antibiotics, bronchodilators, anticholinergics, glucocorticoids, eicosanoid inhibitors, CFTR modulators, agents to restore airway surface liquid, anti-inflammatory agents, and combinations thereof.

49. The method of claim 48, wherein co-administering comprises inhaling the additional active agent.

50. The method of claim 48, wherein the antibiotic is selected from the group consisting of tobramycin, aztreonam, ciprofloxacin, azithromycin, tetracycline, quinupristin, linezolid, vancomycin, and chloramphenicol, colisitin and combinations thereof.

51. The method of claim 48, wherein the bronchodilator is selected from the group consisting of salbutamol, levosalbuterol, terbutaline, fenoterol, terbutlaine, pirbuterol, procaterol, bitolterol, rimiterol, carbuterol, tulobuterol, reproterol, salmeterol, formoterol, arformoterol, bambuterol, clenbuterol, indacterol, theophylline, roflumilast, cilomilast, and combinations thereof.

52. The method of claim 48, wherein the anticholinergic is selected from the group consisting of ipratropium, tiotropium, and combinations thereof.

53. The method of claim 48, wherein the glucocorticoid is selected from the group consisting of prednisone, fluticasone, budesonide, mometasone, ciclesonide, beclomethasone, and combinations thereof.

54. The method of claim 48, wherein the CFTR modulator is selected from the group consisting of VX-770, atluren, VX-809, and combinations thereof.

55. The method of claim 48, wherein the agents to restore airway surface liquid is selected from the group consisting of denufosol, mannitol, GS-9411, SPI-8811, and combinations thereof.

56. The method of claim 48, wherein the anti-inflammatory agent is selected from the group consisting of ibuprofen, sildenafil, simavastatin, and combinations thereof.

57. The method of claim 48, wherein the eicosanoid inhibitor is selected from the group consisting of montelukast, pranlukast, zafirlukast, zileuton, ramatroban, seratrodast, and combinations thereof.

58. The method of claim 1, comprising administering the aerosol once daily.

59. The method of claim 1, comprising administering the aerosol twice daily.

60. A method of treating a chronic lung infection, comprising administering to a subject having a chronic lung infection an aerosol of a solution comprising levofloxacin or ofloxacin and a divalent or trivalent cation to achieve a maximum lung sputum concentration ($C_{max}$) of at least 1200 mg/L and a lung sputum area under the curve (AUC) of at least 1500 h·mg/L, wherein the solution comprises a divalent or trivalent cation concentration from about 50 mM to about 400 mM, and a levofloxacin or ofloxacin concentration from between about 50 mg/ml to about 200 mg/ml.

61. The method of claim 60, wherein the solution consists essentially of levofloxacin or ofloxacin and the divalent or trivalent cation.

62. The method of claim 60, wherein the solution comprises no lactose.

63. The method of claim 60, wherein the human has a pulmonary disorder selected from the group consisting of cystic fibrosis, chronic obstructive pulmonary disease, chronic bronchitis, bronchiectasis, pneumonia, and asthma.

64. The method of claim 60, wherein the solution comprises a divalent or trivalent cation concentration from about 100 mM to about 300 mM, and a levofloxacin or ofloxacin concentration from about 75 mg/ml to about 150 mg/ml.

65. The method of claim 60, wherein the solution comprises a divalent or trivalent cation concentration from about 150 mM to about 250 mM, and a levofloxacin or ofloxacin concentration from about 90 mg/ml to about 125 mg/ml.

66. The method of claim 60, wherein the solution comprises an osmolality from about 300 mOsmol/kg to about 600 mOsmol/kg, and a pH from about 5 to about 8.

67. The method of claim 60, wherein the solution comprises an osmolality from about 350 mOsmol/kg to about 425 mOsmol/kg, and a pH from about 5 to about 6.5.

68. The method of claim 60, wherein the solution comprises a pH from about 5.5 to about 6.5.

69. The method of claim 60, wherein the divalent or trivalent cation is selected from magnesium, calcium, zinc, copper, aluminum, and iron.

70. The method of claim 60, wherein the solution comprises magnesium chloride.

71. The method of claim 60, further comprising co-administering an additional active agent selected from the group consisting of antibiotics, bronchodilators, anticholinergics, glucocorticoids, eicosanoid inhibitors, and combinations thereof.

72. The method of claim 71, wherein co-administering comprises inhaling the additional active agent.

73. The method of claim 71, wherein the antibiotic is selected from the group consisting of tobramycin, aztreonam, ciprofloxacin, azithromycin, tetracycline, quinupristin, linezolid, vancomycin, and chloramphenicol, colisitin and combinations thereof.

74. The method of claim 71, wherein the bronchodilator is selected from the group consisting of salbutamol, levosalbuterol, terbutaline, fenoterol, terbutlaine, pirbuterol, procaterol, bitolterol, rimiterol, carbuterol, tulobuterol, reproterol, salmeterol, formoterol, arformoterol, bambuterol, clenbuterol, indacterol, theophylline, roflumilast, cilomilast, and combinations thereof.

75. The method of claim 71, wherein the anticholinergic is selected from the group consisting of ipratropium, tiotropium, and combinations thereof.

76. The method of claim 71, wherein the glucocorticoid is selected from the group consisting of prednisone, fluticasone, budesonide, mometasone, ciclesonide, beclomethasone, and combinations thereof.

77. The method of claim 71, wherein the eicosanoid inhibitor is selected from the group consisting of montelukast, pranlukast, zafirlukast, zileuton, ramatroban, seratrodast, and combinations thereof.

78. The method of claim 60, comprising administering the aerosol once daily.

79. The method of claim 60, comprising administering the aerosol twice daily.

80. The method of claim 1, wherein the solution comprises a levofloxacin or ofloxacin concentration from about 90 mg/ml to about 110 mg/ml, a magnesium chloride concentration from about 175 mM to about 225 mM, a pH from about 5 to about 7; an osmolarity from about 300 mOsmol/kg to about 500 mOsmol/kg, and lacks lactose.

* * * * *

UNITED STATES PATENT AND TRADEMARK OFFICE
CERTIFICATE OF CORRECTION

| | | |
|---|---|---|
| PATENT NO. | : 8,815,838 B2 | Page 1 of 1 |
| APPLICATION NO. | : 12/574680 | |
| DATED | : August 26, 2014 | |
| INVENTOR(S) | : Griffith et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 580 days.

Signed and Sealed this
Twenty-third Day of February, 2016

Michelle K. Lee
*Director of the United States Patent and Trademark Office*